United States Patent
Cook et al.

[11] Patent Number: 5,886,177
[45] Date of Patent: Mar. 23, 1999

[54] PHOSPHATE LINKED OLIGOMERS

[75] Inventors: Phillip Dan Cook, Vista; Oscar L. Acevedo, San Diego; Peter W. Davis, Carlsbad; David J. Ecker, Encinitas; Normand Hebert, Cardiff, all of Calif.

[73] Assignee: ISIS Pharmaceuticals, Inc., Carlsbad, Calif.

[21] Appl. No.: 669,506

[22] PCT Filed: Jan. 11, 1995

[86] PCT No.: PCT/US95/00449

§ 371 Date: Aug. 8, 1996

§ 102(e) Date: Aug. 8, 1996

[87] PCT Pub. No.: WO95/18820

PCT Pub. Date: Jul. 13, 1995

Related U.S. Application Data

[63] Continuation-in-part of Ser. No. 179,970, Jan. 11, 1994.

[51] Int. Cl.⁶ .................................................. C07D 237/00
[52] U.S. Cl. .......................... 544/224; 435/6; 436/501; 530/300; 530/350; 536/22.1; 536/23.1; 536/24.1; 536/24.3; 536/24.31; 536/24.32; 536/24.33; 544/1; 544/232; 544/233; 544/235; 544/236; 544/238; 544/239
[58] Field of Search ...................... 435/5, 6, 810; 436/501; 530/300, 350; 536/22.1, 23.1, 24.1, 24.3–33; 935/77, 78; 544/1, 224, 232, 233, 235, 236, 238, 239

[56] References Cited

U.S. PATENT DOCUMENTS

| | | | |
|---|---|---|---|
| 3,687,808 | 8/1972 | Merigan et al. | 195/28 N |
| 3,856,835 | 12/1974 | Guillot | 260/429.9 |
| 4,958,013 | 9/1990 | Letsinger | 536/27 |
| 5,144,045 | 9/1992 | Wissner et al. | 549/219 |
| 5,210,264 | 5/1993 | Yau | 558/167 |
| 5,212,295 | 5/1993 | Cook | 536/26.7 |
| 5,218,105 | 6/1993 | Cook et al. | 536/25.31 |
| 5,419,966 | 5/1995 | Reed et al. | 428/406 |
| 5,578,718 | 11/1996 | Cook et al. | 536/27.21 |
| 5,587,471 | 12/1996 | Cook et al. | 536/25.3 |

FOREIGN PATENT DOCUMENTS

| | | |
|---|---|---|
| 0 313 219 A2 | 4/1989 | European Pat. Off. |
| WO 92/02532 | 2/1992 | WIPO |
| WO 92/02534 | 2/1992 | WIPO |
| WO 92/03568 | 3/1992 | WIPO |
| WO 92/05186 | 4/1992 | WIPO |
| WO 93/04204 | 3/1993 | WIPO |
| WO 93/07883 | 4/1993 | WIPO |
| WO 93/15221 | 8/1993 | WIPO |

OTHER PUBLICATIONS

Fontanel, M.L. et al., "End Attachment of Phenol–Oligonucleotide Conjugates to Diazotized Cellulose", *Bioconj. Chem.*, 1993, 4, 380–385.

Grzybowski, J. et al., "Synthesis and antibody–mediated detection of oligonucleotides containing multiple 2,4–dinitrophenyl reporter groups", *Nucl. Acids Res.*, 1993, 21(8), 1705–1712.

Korshun, V.A. et al., "Reagent for Introducing Pyrene Residues in Oligonucleotides", *Bioconj. Chem.*, 1992, 3(6), 559–562.

(List continued on next page.)

*Primary Examiner*—Ardin H. Marschel
*Attorney, Agent, or Firm*—Woodcock Washburn Kurtz Mackiewicz & Norris, LLP

[57] ABSTRACT

Novel ethylene glycol compounds bearing various functional groups are used to prepare oligomeric structures. The ethylene glycol monomers can be joined via standard phosphate linkages including phosphorothioate, phosphodiester, and phosphoramidate linkages. Useful functional groups include nucleobases as well as polar groups, hydrophobic groups, ionic groups, aromatic groups and/or groups that participate in hydrogen-bonding.

22 Claims, 2 Drawing Sheets

OTHER PUBLICATIONS

MacKellar, C. et al., "Synthesis and physical properties of anti–HIV antisense oligonucleotides bearing terminal lipophilic groups", *Nucl. Acids Res.*, 1992, 20(13), 3411–3417.

Nelson, P.S. et al., "A new and versatile reagent for incorporating multiple primary aliphatic amines into synthetic oligonucleotides", *Nucl. Acids Res.*, 1989, 17(18), 7179–7186.

Dennis, "Phospholipases," *The Enzymes*, Boyer, P.D., ed., New York: Academic Press, 1983, vol. 16, Chapter 9, 307–353.

Glaser, et al., "Phospholipase $A_2$ enzymes: regulation and inhibition," *TIPS Review*, 1993, 14, 92–98.

Pruzanski, et al., "Enzymatic Activity and Immunoreactivity of Extracellular Phospolipase $A_2$ in Inflammatory Synovial Fluids," *Inflammation*, 1992, 16, 451–457.

Vishwanath, et al., "Edema–Inducing Activity of Phospholipase $A_2$ Purified from Human Synovial Fluid and Inhibition by Aristolochic Acid," *Inflammation*, 1988, 12, 549–561.

Bomalaski, et al., "Human Extracellular Recombinant Phospholipase $A_2$ Induces an Inflammatory Response in Rabbit Joints," *J. Immunol.*, 1991, 146, 3904–3910.

Scott, et al., "Interfacial Catalysis: The Mechanism of Phospholipase $A_2$," *Science*, 1990, 250, 1541–1546.

Wery, et al., "Structure of recombinant human rheumatoid arthritic synovial fluid phospholipase $A_2$ at 2.2 Å resolution," *Nature*, 1991, 352, 79–82.

Achari, et al., "Facing up to Membranes: Structure/Function Relationships in Phospholipases," *Cold Spring Harbor Symp. Quant. Biol.*, 1987, 52, 441–452.

Cho, et al., "The Chemical Basis for Interfacial Activation of Monomeric Phospholipases $A_2$," *J. Biol. Chem.*, 1988, 263, 11237–11241.

Yang, et al., "Studies on the status of lysine residues in phospholiapse $A_2$ from Naja naja atra (Taiwan cobra) snake venom," *Biochem. J.*, 1989, 262, 855–860.

Noel, et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition," *J. Am. Chem. Soc.*, 1990, 112, 3704–3706.

Burack, et al., "Role of Lateral Phase Separation in the Modulation of Phospholipase $A_2$ Activity," *Biochemistry*, 1993, 32, 583–589.

Grainger, et al., "An enzyme caught in action: direct imaging of hydrolytic function and domain formation of phospholipase $A_2$ in phosphatidylcholine monolayers," *FEBS Lett.*, 1989, 252, 73–82.

Yuan, et al., "Synthesis and Evaluation of Phospholipid Analogues as Inhibitors of Cobra Venom Phospholipase $A_2$," *J. Am. Chem. Soc.*, 1987, 109, 8071–8081.

Lombardo, et al., "Cobra Venom Phospholipase $A_2$ Inhibition by Manoalide," *J. Biol. Chem.*, 1985, 260, 7234–7240.

Washburn, et al., "Suicide–inhibitory Bifunctionally Linked Substrates (SIBLINKS) as Phospholipase $A_2$ Inhibitors," *J. Biol. Chem.*, 1991, 266, 5042–5048.

Campbell, et al., "Inhibition of Phospholipase $A_2$; a Molecular Recognition Study," *J. Chem. Soc., Chem. Commun.*, 1988, 1560–1562.

Davidson, et al., "1–Stearyl,2–Stearoylaminodeoxy Phosphatidylcholine, A Potent Reversible Inhibitor of Phospholipase $A_2$," *Biochem. Biophyis. Res. Commun.*, 1986, 137, 587–592.

Miyake, et al., "The Novel Natural Product YM–26567–1 [(+)–trans–4–(3–dodecanoyl–2,4,6–trihydroxyphenyl) –7–hydroxy–2–(4–hydroxyphenyl)chroman]: A Competitive Inhibitor of Group II Phospholipase $A_2$," *J. Pharmacol. Exp. Ther.*, 1992, 263, 1302–1307.

Geysen, et al., "Strategies for epitope analysis using peptide synthesis," *J. Immun. Meth.*, 1987, 102, 259–274.

Houghton, et al., "Generation and use of synthetic peptide combinatorial libraries for basic research and drug discovery," *Nature*, 1991, 354, 84–86.

Owens, et al., "The Rapid Identification of HIV Protease Inhibitors Through the Synthesis and Screening of Defined Peptides Mixtures," *Biochem. Biophys. Res. Commun.*, 1991, 181, 402–408.

Wyatt, et al., "Combinatorially Selected Guanosine–Quartet Structure is a Potent Inhibitor of Human Immunodeficiency Virus Envelope–Mediated Cell Fusion", *Proc. Natl. Acad. Sci. USA*, 1994, 91, 1356–1360.

Ecker, et al., "Rational screening of oligonucleotide combinatorial libraries for drug discovery," *Nucleic Acids Res.*, 1993, 21, 1853–1856.

Ko, et al., "p–Nitrobenzoate Esters of Eposy Alcohols: Convenient Synthons for Water–Soluble Epoxy Alcohols", *J. Org. Chem.*, 1987, 52, 667–671.

Ko, et al., "In Situ Opening of epoxy Alcohols: A Convenient Alternative to the Isolation of Unstable Epoxy Alcohols", *J. Org. Chem.*, 1986, 51, 5413–5415.

Klunder, et al., "Asymmetric Epoxidation of Allyl Alcohol: Efficient Routes to Homochiral β–Adrenergic Blocking Agents", *J. Org. Chem.*, 1986, 51, 3710–3712.

Green and Wuts, "Protective Groups in Organic Synthesis", 2nd Ed., *John Wiley & Sons*, New York, 1991.

Concise Encyclopedia of Polymer Science and Engineering, J.I. Kroschwitz, Ed., *John Wiley & Sons*, 1990, 858–859.

"Oligonucleotide Synthesis, A Practical Approach", M.J. Gait, Ed., Oxford University Press, New York, N.Y., 1990.

Alul, et al., "Oxalyl–CPG: a labile support for synthesis of sensitive oligonucleotide derivatives," *Nucleic Acids Research*, 1991, 19, 1527–1532.

Beaucage, et al., "Advances in the Synthesis Oligonucleotides by the Phosphoramidite Approach," *Tetrahedron*, 1992, 48, 2223–2311.

Franson, et al., "Phospholipid metabolism by phagocytic cells. Phospholipases $A_2$ associated with rabbit polymorphonuclear leukocyte granules," *J. Lipid Res.*, 1974, 15, 380–388.

Englisch, et al., "Chemically Modified Oligonucleotides as Probes and Inhibitors," *Angewandte Chemie, International Edition*, 1991, 30, 613–629.

Davidson, et al., "Inhibition of Phosphilipase $A_2$ by Lipocortins and Calpactins," *J. Biol. Chem.*, 1987, 262, 1698–1705.

Hanson, "The Synthetic Methodology of Nonracemic Glycidol and Related 2,3–Epoxy Alcohols", *Chemical Reviews*, 1991, 91, 437–475.

Mellor, D.P., "Chemistry of Chelation and Chelating Agents in International Encyclopedia of Pharmacology and Therapeutics", The Chelation of Heavy Metals, Levine, W.G., Ed., Pergamon Press, Elmford, N.Y., Section 70, 1979.

Tanaka, et al., "A Novel Type of Phospholipase $A_2$ Inhibitor, Thielocin A1β, and Mechanism of Action," *J. Antibiotics*, 1992, 45, 1071–1078.

Oinuma, et al., "Synthesis and Biological Evaluation of Substituted Benzenesulfonamides as Novel Potent Membrane–Bound Phospholipase $A_2$ Inhibitors," *J. Med. Chem.*, 1991, 34, 2260–2267.

Marki, et al., "Differential inhibition of human secretory and cytosolic phospholipase $A_2$," *Agents Actions*, 1993, 38, 202–211.

Wright, et al., "Large Scale Synthesis Oligonuclotides via Phosphoramidite Nucleosides and a High–loaded Polystyrene Support," *Tetrahedron Letters*, 1993, 34, 3373–3376.

Klunder, et al., "Arenesulfonate Derivatives of Homochiral Glycidol: Versatile Chiral Building blocks for organic Synthesis", *J. Org. Chem.*, 1989, 54, 1295–1304.

Misiura, et al., "Biotinyl and phosphotyrosinyl phosphoramidite derivatives useful in the incorporation of multiple reporter groups on synthetic oligonucleotides", *Nucleic Acids Research*, 1990, 18, 4345–4354.

Pon, R.T., Protocols For Oligonucleotides And Analogs, S. Agrawal, (ed.), Humana Press, Totowa, N.J., 1993, 465–496.

Ramirez, et al., "Nucleotidophospholipids: Oligonucleotide Derivatives with Membrane–Recognition Groups", *J. Am. Chem. Soc.*, 1982, 104, 5483–5486.

Telser, et al., "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements", *J. Am. Chem. Soc.*, 1989, 111, 6966–6976.

Buckheit et al., "Thiazolobenzimidazole: biological and biochemical anti–retroviral of a new nonnucleoside reverse transcriptase inhibitor", *Antiviral Res.*, 1993, 21, 247–265.

Farooqui, F. et al., "Effect of Structural Variations in Cholesteryl–Conjugated Oligonucleotides on Inhibitory Activity toward HIV–1", *Bioconjugate Chem.*, 1991, 2, 422–426.

Froehler, B.C. et al., "Nucleoside H–Phosphonates: Valuable Intermediates in the Synthesis of Deoxyoligonucleotides", *Tetra. Lett.*, 1986, 27, 469–472.

Froehler, B.C., "Deoxynucleoside H–Phosphonate Diester Intermediates in the Synthesis of Internucleotide Phosphate Analogues", *Tetra. Lett.*, 1986, 27, 5575–5578.

Froehler, B.C. et al., "Protocols for Olgonucleotides and Analogs –Synthesis and Properties", *Methods in Molecular Biology*, Agrawal, S. (Ed.), Humana Press, Totowa, 1993, vol. 20, 63–80.

Garegg et al., "Nucleoside Hydrogenphosphonates in Oligonucleotide Synthesis", *Chem. Scripta*, 1986, 26, 159–162.

Gryaznov, S.M. et al.,"A New Method for the Synthesis of Oligodeoxyribonucleotides Containing Internucleotide Phosphoramidate Bonds", *Tetra. Lett.*, 1990, 31 (22) , 3205–3208.

Gryaznov, S.M. et al., "A New Approach to the Synthesis of Oligodeoxyribonucleotides with Alkylamino Groups Linked to Internucleotide Phosphate Groups", *Tetra. Lett.*, 1991, 32 (30) , 3715–3718.

Iso, Y. et al., "Synthesis of Viologen–Tagged Oligodeoxynucleotides", *Tetra. Lett.*, 1992, 33 (4) , 503–506.

Jung, P.M. et al., "Hybridization of Alternating Cationic/Anionic Oligonucleotides to RNA Segments", *Nucleosides & Nucleotides*, 1994, 13, 1597–1605.

Letsinger, R.L. et al., "Cationic Oligonucleotides", *J. Am. Chem. Soc.*, 1988, 110, 4470–4471.

Hebert et al, "Synthesis of N–Substituted Hydroxyprolinol Phpsphoramidites for the Preparation of Combinatorial Libraries", *Tetra. Lett.*, 1994, 35 (51) , 9509–9512.

Peterson et al., "Synthesis and Biological Evaluation of 4–Purinylpyrrolidine Nucleosides", *J. Med. Chem.*, 1991, 34, 2787–2797.

Takahashi et al., "Preparation of New chiral Pyrrolidine–e–bisphosphines as Highly Effective Ligands for Catalytic Assymetic Synthesis of R–(–)–Pantolactone[1)]", *Tetra. Lett.*, 1986, 27 (37) , 4477–4480.

Takeda, et al., "Practical Asymmetric Synthesis of (R) –(–) –Phenylephrine Hydrochloride Catalyzed by (2R,4R) –MCCPM–Rhodium Complex[1,2)]", *Tetra. Lett.*, 1989, 30 (3), 367–370.

Augustyns et al. (1991) Nucleic Acids Research, vol. 19, No. 1, pp. 2587–2593.

PHOSPHATE LINKED OLIGOMERS

CROSS REFERENCE TO RELATED APPLICATION

This application is a 371 filing of PCT/US95/00449, filed Jan. 11, 1995, and a continuation in part of U.S. Ser. No. 08/179,970 filed Jan. 11, 1994, the contents of which are incorporated by reference herein in their entirety.

FIELD OF THE INVENTION

This invention is directed to alkylene glycol monomeric units and to oligomers constructed from these units. The oligomers can be synthesized to have either random or predefined sequences of monomeric units and can be joined via phosphate linkages, including phosphorothioate, phosphodiester, and phosphoramidate linkages. Each of the monomeric units can include a chemical moiety thereon for binding of the oligomeric structures to proteins, nucleic acid, and other biological targets. In preferred embodiments, the compounds of the invention act as inhibitors of enzymes such as phospholipase $A_2$ and are used for the treatment of inflammatory diseases including atopic dermatitis and inflammatory bowel disease.

BACKGROUND OF THE INVENTION

Phospholipases $A_2$ ($PLA_2$) are a family of enzymes that hydrolyze the sn-2 ester linkage of membrane phospholipids resulting in release of a free fatty acid and a lysophospholipid (see, Dennis, E. A., The Enzymes, Vol. 16, pp. 307–353, Boyer, P. D., ed., Academic Press, New York, 1983). Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (see, e.g., Dennis, ibid.; Glaser, et al., TiPs Reviews 1992, 14, 92; and Pruzanski, et al., Inflammation 1992, 16, 451).

All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath, et al., Inflammation 1988, 12, 549) or into the articular space of rabbits (Bomalaski, et al., J. Immunol. 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g., pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott, et al., Science 1990, 250, 1541). Recently, the crystal structure of $PLA_2$ from human synovial fluid has been solved (Wery, et al., Nature 1991, 352, 79). The structures clarify the role of calcium and amino acid residues in catalysis. The calcium acts as a Lewis acid to activate the scissile ester carbonyl and bind the lipid, and a His-Asp side chain dyad acts as general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site. (see, e.g., Achari, et al., Cold Spring Harbor Symp. Quant. Biol. 1987, 52, 441; Cho, et al., J. Biol. Chem. 1988, 263, 11237; Yang, et al., Biochem. J. 1989, 262, 855; and Noel, et al., J. Am. Chem. Soc. 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. The evidence favoring this hypothesis comes from studies revealing that rapid changes in $PLA_2$ activity occur concurrently with changes in the fluorescence of a membrane probe (Burack, et al., Biochemistry 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of PLA2 activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger, et al., FEBS Lett. 1989, 252, 73). These studies clearly show that $PLA_2$ binds exclusively at the boundary region between liquid and solid phase lipid.

While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e., phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (see, e.g., Yuan, et al., J. Am. Chem. Soc. 1987, 109, 8071; Lombardo, et al., J. Biol. Chem. 1985, 260, 7234; Washburn, et al., *J. Biol. Chem.* 30 1991, 266, 5042; Campbell, et al., *J. Chem. Soc., Chem. Commun.* 1988, 1560; and Davidson, et al., *Biochem. Biophys. Res. Commun.* 1986, 137, 587), reports describing in vivo activity are limited (see, e.g., Miyake, et al., *J. Pharmacol. Exp. Ther.* 1992, 263, 1302).

Traditional structure activity relationship type drug discovery gives unambiguous products but yet requires the preparation of numerous individual test candidates. The preparation of each structure requires significant amounts of time and resources. Another drug discovery approach, de novo design of active compounds based on high resolution enzyme structures, generally has not been successful. Yet another approach involves screening complex fermentation broths and plant extracts for a desired biological activity. The advantage of screening mixtures from biological sources is that a large number of compounds can be screened simultaneously, in some cases leading to the discovery of novel and complex natural products with activity that could not have been predicted otherwise. One disadvantage is that many different samples must be screened and numerous purifications must be carried out to identify the active component, which often is present only in trace amounts.

In order to maximize the advantages of each classical approach, new strategies for combinatorial unrandomization have been developed by several groups. Selection techniques have been used with libraries of peptides (see, e.g., Geysen, et al., *J. Immun. Meth.* 1987, 102, 259; Houghten, et al., *Nature* 1991, 354, 84; and Owens, et al., *Biochem. Biophys. Res. Commun.* 1991, 181, 402) and nucleic acids (see, e.g., Wyatt, et al., (in press) *Proc. Natl. Acad. Sci. USA;* and Ecker, et al., *Nucleic Acids Res.* 1993, 21, 1853). These selection techniques involve iterative synthesis and screening of increasingly simplified subsets of oligomers. In using these selection techniques, subsets are assayed for activity in either cell-based assays, or for binding or inhibition of purified protein targets.

One technique, called SURF (Synthetic Unrandomization of Randomized Fragments; see, e.g., Ecker, et al., ibid., involves the synthesis of subsets of oligomers containing a known residue at one fixed monomer position and equimolar mixtures of residues at all other positions. For a library of oligomers four residues long containing three monomers (A, B, C), three subsets would be synthesized (NNAN, NNBN, NNCN, where N represents equal incorporation of each of the three monomers). Each subset is then screened in a functional assay and the best subset is identified (e.g., NNAN) A second set of libraries is synthesized and screened, each containing the fixed residue from the previous round, and a second fixed residue (e.g. ANAN, BNAN, CNAN). Through successive rounds of screening and synthesis, a unique sequence with activity in the assay can be identified.

OBJECTS OF THE INVENTION

It is an object of this invention to provide novel alkane glycol monomeric units.

It is another object of the invention to provide novel alkane glycol monomeric units that can be incorporated into novel oligomeric structures.

It is a further object to provide novel alkane glycol monomeric units that can be linked together via phosphorus-containing backbones.

It is still another object to provide novel alkane glycol based oligomers that include a diversity of functional moieties thereon for binding to biological sites of interest.

BRIEF DESCRIPTION OF THE INVENTION

Compounds of the invention include monomeric compounds of structure I:

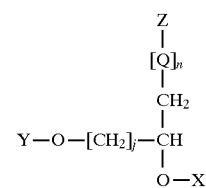

wherein:

X is H, a phosphate group, an activated phosphate group, an activated phosphite group, or a solid support;

Y is H or a hydroxyl protecting group;

Z is $L_1$, $L_1$-$G_1$, $L_2$, $L_2$-$G_2$, $NR_3R_4$, a nitrogen-containing heterocycle, a purine, a pyrimidine, a phosphate group, a polyether group, or a polyethylene glycol group;

$L_1$ is alkyl having 1 to about 20 carbon atoms, alkenyl having 2 to about 20 carbon atoms, or alkynyl having 2 to about 20 carbon atoms;

$L_2$ is aryl having 6 to about 14 carbon atoms or aralkyl having 7 to about 15 carbon atoms;

$G_1$ is halogen, $OR_1$, $SR_2$, $NR_3R_4$, $C(=NH)NR_3R_4$, $NHC(=NH)NR_3R_4$, $CH=O$, $C(=O)OR_5$, $CH(NR_3R_4)(C(=O)OR_5)$, $C(=O)NR_3R_4$, a metal coordination group, or a phosphate group;

$G_2$ is halogen, OH, SH, $SCH_3$, or $NR_3R_4$;

$R_1$ is H, alkyl having 1 to about 6 carbon atoms, or a hydroxyl protecting group;

$R_2$ is H, alkyl having 1 to about 6 carbon atoms, or a thiol protecting group;

$R_3$ and $R_4$ are, independently, H, alkyl having 1 to about 6 carbon atoms, or an amine protecting group;

$R_5$ is H, alkyl having 1 to about 6 carbon atoms, or an acid protecting group;

Q is $L_1$, $G_3$, $L_1$-$G_3$ or $G_3$-$L_1$-$G_3$;

$G_3$ is $NR_3$, $C(=O)$, $C(=S)$, $C(O)$—O, $C(O)$—NH, $C(S)$—O, $C(S)$—NH or $S(O)_2$, $NR_3C(=O)$, $NR_3C(=S)$, $NR_3C(O)$—O, $NR_3C(O)$—NH, $NR_3C(S)$—O, $NR_3C(S)$—NH or $NR_3S(O)_2$;

n is 0 or 1; and j is 1 to 6;

provided that:

if n=0 AND Z is $NH_2$, adenine, guanine, cytosine, uracil or thymine and if one of X or Y is 5 H then the other of X or Y is not H; and if n=0 and Q is alkyl-NH, then Z is not biotin or phosphotyrosinyl.

In preferred embodiments, Y is an acid labile hydroxyl protecting group such as a trityl, methoxytrityl, dimethoxytrityl or trimethoxytrityl group. X preferably is H, an activated phosphite such as a phosphoramidite, an activated phosphate, or a solid support. In certain preferred embodiments, n is 1 and Q is an acyl linking group, an alkyl linking group, an amino linking group or a bifunctional linking group. Preferred acyl group include carbonyl, thiocarbonyl, carboxy, acetyl, amido, succinyl, carbamoyl, thiocarbamoyl, ureido, thioureido, and sulfonamido groups.

In one preferred group of compounds, Z includes a nitrogen-containing heterocycle such as an imidazole or carbazole ring. In a further preferred group, Z includes a purine or a pyrimidine nucleobase. Particularly preferred are compounds wherein X is an activated phosphite, Y is an acid labile hydroxyl protecting group, and Z is adenine, guanine, cytosine, uridine or thymine.

In a further preferred group of compounds, Z includes Z includes an unsubstituted or amine-substituted alkyl group having 2 to about 20 atoms, an aryl group having 6 to about 20 carbon atoms, or an aralkyl group having 7 to about 15 carbon atoms. In yet another preferred group of compounds, Z includes fluorenylmethyl, phenyl, benzyl, polyethylene glycol, glutamyl, or $NR_1R_2$ groups.

Further compounds of the invention include oligomeric compounds of structure II:

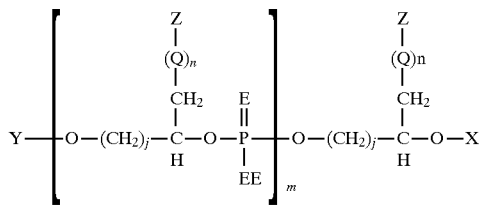

wherein:

X is H, a phosphate group, an activated phosphate group, an activated phosphite group, a solid support, a conjugate group, or an oligonucleotide;

Y is H, a hydroxyl protecting group, a conjugate group or an oligonucleotide;

E is O or S;

EE is $O^-$, or $N(Y_0)T_0$;

$Y_0$ is H, or $[Q_2]_{jj}$-$Z_2$;

$T_0$ is $[Q_1]_{kk}$-$Z_1$, or together $Y_0$ and $T_0$ are joined in a nitrogen heterocycle;

$Q_1$ and $Q_2$ independently, are $C_2$–$C_{10}$ alkyl, $C_2$–$C_{10}$ alkenyl, $C_2$–$C_{10}$ alkynyl, $C_4$–$C_7$ carbocylo alkyl or alkenyl, a heterocycle, an ether having 2 to 10 carbon atoms and 1 to 4 oxygen or sulfur atoms, a polyalkyl glycol, or $C7$–$C_4$ aralkyl;

jj and kk independently, are 0 or 1;

$Z_1$ and $Z_2$, independently, are H, $C_1$–$C_2$ alkyl, $C_2$–$C_{20}$ alkenyl, $C_2$–$C_{20}$ alkynyl, $C_6$–$C_{14}$ aryl, $C_7$–$C_{15}$ aralkyl, a halogen, CH=O, $OR_1$, $SR_2$, $NR_3R_4$, C(=NH)$NR_3R_4$), CH(NR_3R_4), NHC(=NH)NR_3R_4, CH(NH_2)C(=O)OH, C(=O)NR_3R_4, C(=O)OR_5, a metal coordination group, a reporter group, a nitrogen-containing heterocycle, a purine, a pyrimidine, a phosphate group, a polyether group, or a polyethylene glycol group;

Z is $L_1$, $L_1$-$G_1$, $L_2$, $L_2$-$G_2$, $NR_3R_4$, a nitrogen-containing heterocycle, a purine, a pyrimidine, a phosphate group, a polyether group, or a polyethylene glycol group;

$L_1$ is alkyl having 1 to about 20 carbon atoms, alkenyl having 2 to about 20 carbon atoms, or alkynyl having 2 to about 20 carbon atoms;

$L_2$ is aryl having 6 to about 14 carbon atoms or aralkyl having 7 to about 15 carbon atoms;

$G_1$ is halogen, $OR_1$, $SR_2$, $NR_3R_4$, C(=NH)$NR_3R_4$, NHC(=NH)$NR_3R_4$, CH=O, C(=O)$OR_5$, CH(NR_3R_4)(C(=O)$OR_5$), C(=O)$NR_3R_4$, a metal coordination group, or a phosphate group;

$G_2$ is halogen, OH, SH, $SCH_3$, or $NR_3R_4$;

$R_1$ is H, alkyl having 1 to about 6 carbon atoms, or a hydroxyl protecting group;

$R_2$ is H, alkyl having 1 to about 6 carbon atoms, or a thiol protecting group;

$R_3$ and $R_4$ are, independently, H, alkyl having 1 to about 6 carbon atoms, or an amine protecting group;

$R_5$ is H, alkyl having 1 to about 6 carbon atoms, or an acid protecting group;

Q is $L_1$, $G_3$, $L_1$-$G_3$ or $G_3$-$L_1$-$G_3$;

$G_3$ is $NR_3$, C(=O), C(=S), C(O)—O, C(O)—NH, C(S)—O, C(S)—NH or $S(O)_2$, $NR_3C(=O)$, $NR_3C(=S)$, $NR_3C(O)$—O, $NR_3C(O)$—NH, $NR_3C(S)$—O, $NR_3C(S)$—NH or $NR_3S(O)_2$;

n is 0 or 1;

j is 1 to 6; and m is 1 to 50.

In oligomeric compounds, X, Y, Z, Q, $R_1$, $R_2$, j and n are as defined above and m is from 1 to about 25.

Further compounds of the invention include chimeric oligomeric compounds having a central region comprising a phosphodiester or a phosphorothioate oligodeoxynucleotide interspaced between flanking regions comprising the above-described monomeric or oligomeric structures.

The invention further includes processes for preparing randomized oligomeric compounds including the steps of selecting a group of monomers as described above and covalently bonding at least two of the monomers of said group. In preferred processes, the Z moiety of at least one monomer of said group is different from the Z moiety of another monomer of said group. Compounds prepared by this process preferably are randomized oligomeric compounds having from 2 to 50 monomers, more preferably 2 to about 25 monomers.

The compounds of the invention can be used as inhibitors of various enzymes including phospholipase $A_2$ enzyme. As inhibitors of phospholipase $A_2$, the compounds are useful for the treatment of inflammatory diseases including atopic dermatitis and inflammatory bowel disease. The oligomeric compounds of the invention can be used in diagnostics since they are capable of specifically hybridizing to nucleic acids of interest in the etiology of diseases. The compounds of the invention also can be used as research probes and primers, especially for the study of enzyme biochemistry and protein-nucleic acid interactions.

BRIEF DESCRIPTION OF THE DRAWINGS

The numerous objects and advantages of the present invention may be better understood by those skilled in the art by reference to the accompanying figures, in which.

DETAILED DESCRIPTION OF THE INVENTION

Figure 1:
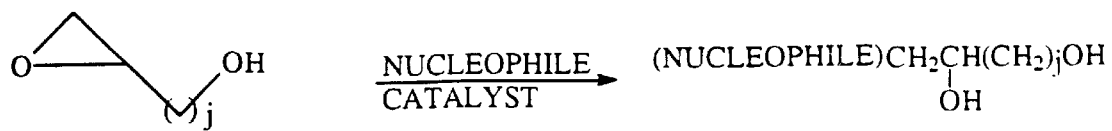
FIGS. 1–4 describe synthetic processes for activated phosphite monomers according to the invention.
Figure 1:
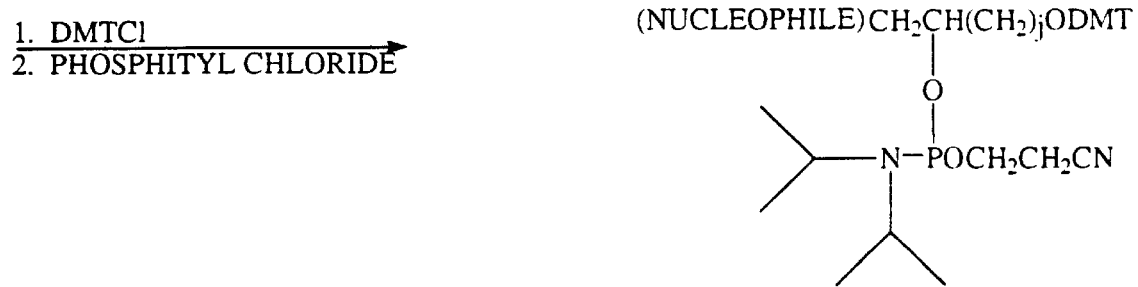

The monomeric compounds of the invention can be considered for identification purposes as substituted alkane glycols, i.e., substituted alkane diols, wherein the alkane portion has from 2 to 7 carbon atoms. In preferred embodiments, the hydroxyl groups of the alkane glycols are used to link adjacent monomers and form oligomeric structures. During oligomer synthesis, one of the glycol hydroxyl groups typically is blocked with a protecting group and the other hydroxyl group is reacted with an activated phosphate group such as a β-cyanoethyl phosphoramidate group. As used herein, the term activated phosphate group is intended to denote a phosphate group that bears a chemical modification thereon to enhance its reactivity with nucleophiles. Similarly, the term activated phosphite group denotes a phosphite group that bears a chemical modification to enhance its reactivity with nucleophiles. Numerous such modifications are known in the art.

The monomeric compounds of the invention preferably are covalently bound using phosphate linkages. This permits coupling via either solution phase or solid phase chemistries. Representative solution phase techniques are described in U.S. Pat. No. 5,210,264, issued May 11, 1993 and commonly assigned with this invention. Representative solid phase techniques are those typically employed for DNA and RNA synthesis utilizing standard phosphoramidite chemistry. (see, e.g., Protocols For Oligonucleotides And Analogs, Agrawal, S., ed., Humana Press, Totowa, N.J., 1993.) A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods. This allows for synthesis of the preferred phosphodiester or phosphorothioate phosphate linkages depending upon oxidation conditions selected. Other phosphate linkages can also be generated. These include phosphorodithioates, phosphotriesters, alkyl phosphonates, phosphoroselenates and phosphoamidates.

The alkane glycol moieties can be substituted with various functional groups. When the monomeric compounds are linked together, these functional groups provide diverse properties ("diversity") to the resulting oligomeric compounds. The functional groups include hydrogen-bond donors and acceptors, ionic moieties, polar moieties, hydrophobic moieties, aromatic centers, and electron-donors and acceptors. Together, the properties of the individual monomers contribute to the uniqueness of the oligomers in which they are found. Thus, a library of such oligomers would have a myriad of properties, i.e., "diversity." Collectively, the properties of the individual monomers that together form an oligomer contribute to the uniqueness of such oligomer and impart certain characteristics thereto for interaction with cellular, enzymatic or nucleic acid target sites. The functional groups can be directly linked to the alkane glycol "core" or "back-bone" portion of the monomeric units or they can be connected thereto via a suitable tether. As will be recognized, the core portion of the monomeric units is formed from an alkane glycol moiety such as an ethylene glycol moiety. Hence, the oligomeric compounds of the invention are formed from a plurality of alkane glycol units, e.g., ethylene glycol units, that bear functional groups and are linked together via phosphate linkages.

In a preferred process for preparing compounds of the invention, the alkane glycol cores are generated by ring-opening an epoxide compound. Preferred compounds are those where the variable j in structure I, above, is 1. This preference stems from the fact that stereospecific monomeric compounds wherein j=1 can be prepared and, when incorporated into oligomeric structures, maintain their stereospecificity. Other members of this series, e.g., j=2 to 6, are prepared by methods analogous to those used to prepare compounds wherein j=1. Since larger homologs are generally less stable, they preferably are prepared and used in situ. Such preparation and use can be effected generally in accordance with the methods of Ko, et al., *J. Org. Chem.* 1986, 51, 5413; Ko, et. al., *J. Org. Chem.* 1987, 52, 667; and Klunder, et. al., *J. Org. Chem.* 1989, 54, 1295. Thus, 3,4-epoxy-1-butanol, 4,5-epoxy-1-pentanol, 5,6-epoxy-1-hexanol, 6,7-epoxy-1-heptanol, and 7,8-epoxy-1-octanol can be prepared and used in situ to provide compounds of structure I wherein j=2, 3, 4, 5, and 6, respectively. Glycidol (2,3-epoxy-1-propanol or oxiranemethanol) is particularly suitable for the preparation of compounds wherein j=1 since upon ring opening it can supply both a primary hydroxyl group and a secondary hydroxyl group that can be included in a phosphate linkage in an oligomeric compound of the invention. The primary hydroxy group derives from the alkanol, i.e., —$CH_2OH$, portion of glycidol, whereas the secondary hydroxyl group is generated upon ring opening of glycidol's epoxide ring.

Monomeric compounds of the invention can be prepared by nucleophilic addition of a functional group (or a tether for such functional group) to an epoxide ring-containing starting material. Generally, this addition is effected in a suitable solvent in the presence of a catalyst, as depicted in FIG. 1. Where necessary, transient protecting groups are used to protect reactive functional groups.

Nucleophilic addition to the epoxide ring is an $S_n2$ reaction that occurs exclusively at the C-1 carbon. In compounds of structure I wherein j=1, racemic or nonracemic glycidol can be used as a starting material. When nonracemic (i.e., chiral) glycidol is used, the product is also nonracemic (see, Hanson, *Chemical Reviews* 1991, 91, 437). This affords a simple way to acquire optically active monomers as well as oligomers incorporating such monomers.

For purposes of assigning names, compounds of the invention having structure I can be considered as substituted alkane compounds. For example, when j=1, the resulting compound can be considered a substituted propane compound. Opening of an epoxide ring by nucleophilic addition of a functional group or a tether group yields a substituted diol compound, for example, a 1-substituted 2,3-diol propane having the functional group or the tether linked to the C1 carbon of the alkane moiety. The 1-substituted propane 2,3-diol has both a primary hydroxyl group (i.e., the hydroxyl linked to the C3 carbon, the hydroxy methyl group of the glycidol moiety) and a secondary hydroxyl group (i.e., the hydroxyl group linked to the C2 carbon resulting from the opening of the epoxide ring of glycidol).

Although compounds of the invention having structure II wherein j=1 are considered as propane compounds on a monomeric level, they are considered as substituted ethylene glycol compounds on an oligomeric level since only two of the three carbon atoms of the monomeric propane unit are included in the oligomeric backbone. By extension, butanol monomeric compounds (j=2) become substituted propylene glycol oligomeric compounds, and so on for higher analogs. Thus, when a propane diol monomer is incorporated into oligomeric compounds of the invention, the C2 and C3 carbons of the propane diol moiety become part of the oligomeric ethylene glycol core whereas the C1 carbon of the propane moiety becomes an integral part of either a tether or a functional group extending from the core.

To facilitate inclusion into phosphate-linked oligomeric compounds of the invention, alkane diol-containing monomers that bear functional groups are activated with either an activated phosphite or an active phosphate moiety. Prior to phosphitylation of a secondary hydroxyl group (e.g., when j=1, the C2 propane diol hydroxyl group), the primary hydroxyl group (e.g., when j=1, the C3 propane diol hydroxyl group) is protected. Protection of the primary hydroxyl is effected either before or after ring opening of the epoxide ring. Since addition of a protecting group to the methylhydroxyl group of glycidol renders its epoxide ring less reactive to unassisted nucleophilic addition, protection of the primary hydroxyl group normally will be effected after opening unless other considerations override such post-ring opening protection. When using nucleophiles that can react with the primary hydroxyl group, protection of the hydroxyl group before ring opening ("pre-ring opening") is effected. Such pre-ring opening protection is utilized, for example, for the addition of Grignard reagents and other like reagents.

An acid labile protecting group such as a member of the trityl family preferably can be used for protection of the primary hydroxyl group, whether such protection is effected before or after ring opening. The trityl family includes at least trityl, monomethoxytrityl, dimethoxytrityl and trimethoxytrityl. The dimethoxytrityl group is preferred and can be added by reacting the primary hydroxyl group with 4,4'-dimethoxytrityl chloride. Other hydroxyl protecting groups can be used, such as those described by Beaucage, et al., *Tetrahedron* 1992, 48, 2223.

In other aspects of the present invention the use of acid labile groups which are stable to the trichloroacetic acid treatment used for DMT removal such as BOC-type protecting groups are used. They are stable to extended TCA treatment, but are removed by trifluoroacetic acid solutions (e.g. 5% in $CH_2Cl_2$). Another protecting group class which is compatible to this methodology is the Allyl class. These groups are cleaved using transition metal catalysts. This type of protecting group is particularly valuable in cases where the selective deprotection of a particular functional group is desired while the oligomer is still attached to the solid support, allowing a new reactive site to be uncovered. Additional protecting group tactics are possible: e.g. photolabile protecting groups are also compatible with this methodology.

Following protection of the primary hydroxyl group and ring opening, in either order, the secondary hydroxyl group is converted to an activated phosphorus moiety, preferably an activated phosphite moiety. Phosphitylation can be effected with a suitable reagent such as chloro-β-cyanoethoxy-N,N-diisopropylaminophosphine. Phosphitylation yields a protected monomer that bears either an activated phosphite moiety or an activated phosphate moiety and is suitable for incorporation in to phosphate linked oligomeric compounds of the invention.

Oligomeric compounds of the invention can be synthesized by the methods illustrated in FIGS. 1–4. The depicted synthetic strategy places an emphasis on the ease with which widely different functional groups can be incorporated onto a rigid intermediate. The monomers, as activated phosphates or activated phosphites, are oligomerized either in predetermined sequences using, for example, standard oligonucleotide-type synthetic procedures on a DNA synthesizer or in random sequences using, for example, a combinatorial technique such as the above-described SURF technique.

Monomer units bearing protected or unprotected functional groups can be prepared as described in the examples below. If the functional group is such that it will react with other moieties or reagents during phosphitylation or oligomerization, the functional group can be protected with a protecting group, preferably a base labile protecting group that is removed upon completion of oligomer synthesis.

A first group of preferred monomeric compounds of the invention are prepared by nucleophilic addition of an active nitrogen-containing heterocycle to glycidol. For the purposes of this patent application, nitrogen-containing heterocycles are single or multi-cyclic compounds containing at least one nitrogen atom. The heterocycle can contain heteroatoms other than nitrogen atoms. Such other heteroatoms include but are not limited to oxygen and sulfur. A particularly preferred group of heterocycles are synthetic and natural purine and pyrimidine nucleobases, e.g., adenine, guanine, cytosine, uridine, thymine, xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-aza uracil, cytosine and thymine, 5-uracil (pseudo uracil), 4-thiouracil, 8-halo, amino, thiol, thiolalkyl, hydroxyl and other 8 substituted adenines and guanines, 5-trifluoromethyl and other 5 substituted uracils and cytosines and 7-methylguanine. Other purines and pyrimidines include those disclosed in U.S. Pat. No. 3,687,808, those disclosed in the *Concise Encyclopedia Of Polymer Science And Engineering*, J. I. Kroschwitz, Ed. John Wiley & Sons, 1990 at pages 858–859 and those disclosed by Englisch, et al., *Angewandte Chemie, International Edition* 1991, 30, 613.

Figure 2:
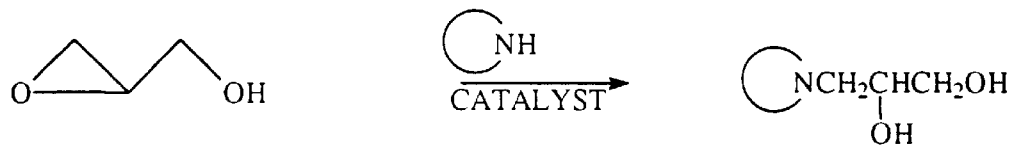
Figure 2:
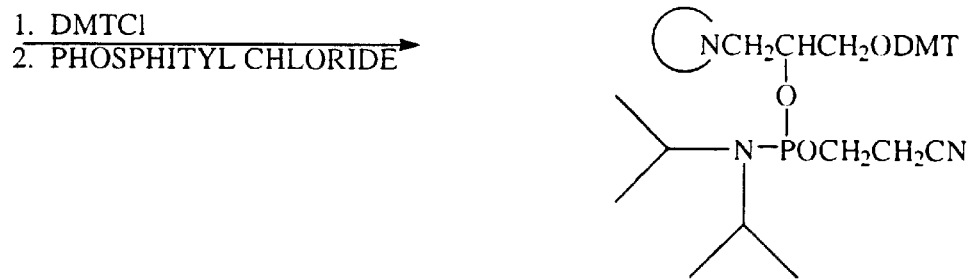

Such nitrogen-containing heterocycles can be added to either glycidol or R-(+)-glycidol in a suitable solvent in the presence of the catalyst such as potassium carbonate, as illustrated in FIG. 2. Where necessary, exocyclic functional groups on the nitrogen heterocycles are protected via transient protection. Particularly useful transient protecting groups for nucleobase exocyclic functional groups are chlorotrimethylsilane, benzoyl chloride, and isobutyryl chloride. The protected compound is then tritylated with 4,4'-dimethoxytrityl chloride in pyridine to protect its primary hydroxyl group. Phosphitylation with chloro-β-cyanoethoxy-N,N-diisopropylaminophosphine and diisopropylethylamine in tetrahdrofuran (THF) yields the corresponding phosphoramidite monomer, which can be incorporated into an oligomeric compound of the invention.

Other nitrogen-containing heterocycles that can be used as functional groups include imidazole, pyrrole, imidazolyl, pyrazole, indole, 1H-indazole, β-carboline, carbazole, phenothiazine, and phenoxazine. A more preferred groups of the nitrogen heterocycle includes imidazole, pyrrole or carbazole. Imidazole is especially preferred.

In preparing monomeric compounds including such heterocycles, protection of exocyclic functional groups with base labile protecting groups is effected as with the nucleobases noted above, the resulting compound is tritylated with 4,4'-dimethoxytrityl chloride, and phosphitylated with chloro-β-cyanoethoxy-N,N-diisopropylaminophosphine to give the desired monomeric compound.

Figure 3:
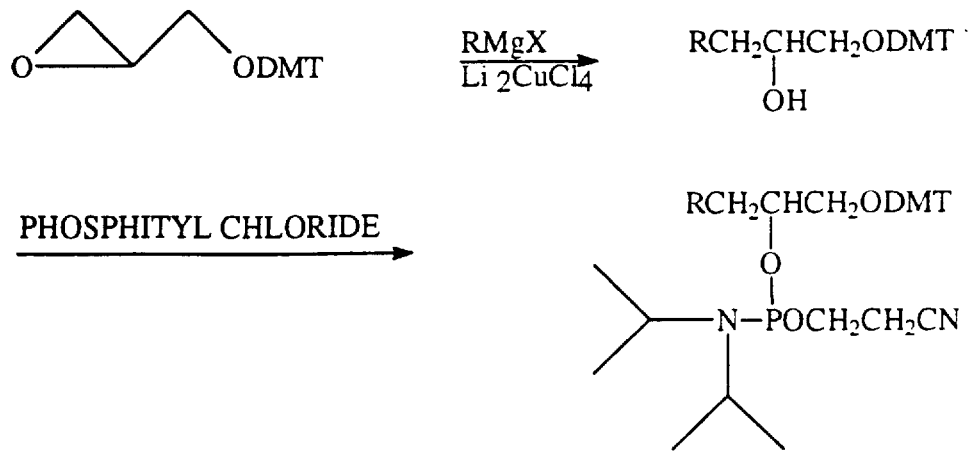

Further preferred monomeric compounds of the invention can be prepared by addition of alkyl, alkenyl, or aryl organometallic reagents to an epoxide ring-containing starting material, e.g., to the 2,3-epoxy ring of glycidol. This is illustrated in FIG. 3. For preparation of such compounds, the primary hydroxy group of the starting material (e.g., the methylhydroxyl group of glycidol) is protected with an acid labile protecting group prior to opening the epoxide ring. As above, suitable as a protecting group is one of the trityl family of protecting groups. Thus, for example, addition of an organomagnesium reagent to 1-O-dimethoxytrityl glycidol can be effected in the presence of dilithium tetrachlorocuprate in a suitable solvent. Phosphitylation using chloro-β-cyanoethoxy-N,N-diisopropylaminophosphine then yields the monomeric compound as the phosphoramidite.

Figure 4:
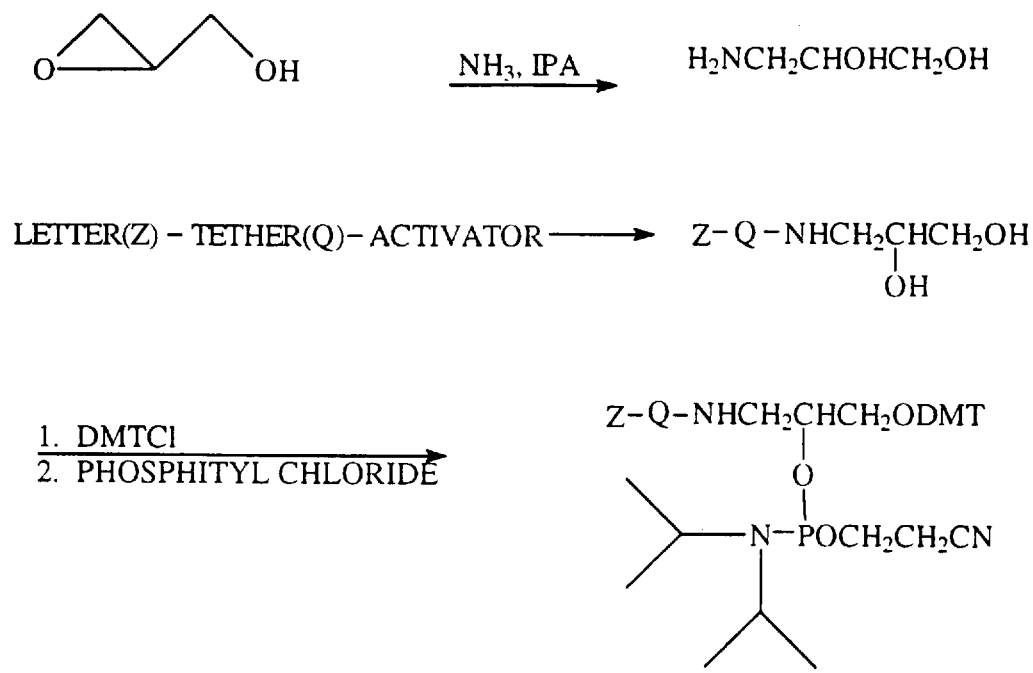

Still further preferred monomeric compounds of the invention can be prepared by nucleophilic addition of ammonia to glycidol. This is illustrated in FIG. 4. The product of this reaction, 1-amino-2,3-propandiol, can be protected with benzoylchloride and the protected compound converted to the DMT-phosphoramidite for incorporation into an oligomer. Alternatively, the amino group of 1-amino-2,3-propandiol can be further functionalized. Functional groups can be attached to the nitrogen directly or via a tether, either by alkylation or acylation. Following functionalization, protection with 4,4'-dimethoxytrityl chloride and phosphitylation with chloro-β-cyanoethoxy-N,N-diisopropylaminophosphine is effected to give the phosphoramidite monomer for inclusion into an oligomeric compound of the invention.

In using the amino group of the above noted 1-amino alkane diol compound as a point for connecting a tether to the alkane diol, the amino group can be reacted either by acylation or alkylation. In one such reaction, the amino group is reacted with a bifunctional linking group, that is, a compound having a first reactive group for linking to the alkane glycol monomeric compound and a second reactive group for linking to the functional group that is being attached to the alkane glycol monomeric compound. One group of bifunctional linking groups or tethers that are particularly preferred are the cyclic anhydrides, including succinic anhydride, maleic anhydride, glutaric anhydride. Thus, for example, the above-noted 1-amino-2,3-propandiol can be reacted with succinic anhydride to form an amide linkage between the propane diol and the succinyl tether group. The other end of the succinyl tether then can be functionalized by, for example, the formation of an ester or amide link with a moiety bearing the desired functional group. This is followed by reaction with 4,4'-dimethoxytrityl chloride and then chloro-β-cyanoethoxy-N,N-diisopropylaminophosphine to give the phosphoramidite monomer for inclusion into oligomeric compounds of the invention.

Other acyl groups can be used in addition to an amide acyl group to link a tether to the above-described 1-amino-2,3-propandiol. Upon acylation of the 1-amino group, such other groups form carbamoyl, thiocarbamoyl, ureido, thioureido, and sulfonamido linkages. Carbamates and thiocarbamates are formed by the reaction of an appropriate chloroformate or thiochloroformate compound with the amino group of the 1-amino-2,3-propandiol. Ureas are formed by reaction of amino-2,3-propandiol with isocynates or thioisocyanates, and sulfonamides are formed by reaction of 1-amino-2,3-propandiol with a sulfonyl chloride. The other end of the tether (i.e., the one not used in linking the tether to amine) is selected so as to be reactive with the functional group that is being attached to the monomeric unit. Acyl linkages, including esters, amides, carbamates, ureas and the like, are also useful for this attachment.

Another group of particularly useful bifunctional linking moieties or tethers are certain heterobifunctional or homobifunctional linkers available from Pierce, Rockford Ill. These include various di-imidates, N-hydroxysuccinimide esters and sulfo-N-hydroxysuccinimide esters. Representative di-imidates include dimethyl adipimidate, dimethyl pimelimidate, dimethyl suberimidate and the like. Representative N-hydroxy-succinimide esters and sulfo-N-hydroxysuccinimide esters include disuccinimidyl suberate, bis(sulfosuccinimidyl) suberate and the like.

A further preferred group of tether compounds include alkyl, alkenyl and aryl compounds. These can be used to alkylate the amino group of 1-amino alkane diol compounds. Alternatively, they can be added to alkane diol compounds directly, e.g, by addition of alkyl, alkenyl or aryl organometallic reagents to the epoxide ring of a suitable starting material. The tether, in turn, can be further functionalized with a functional group.

Preferred functional groups are: alkyl, alkenyl, and alkynyl groups that are optionally substituted with one or more halogens, $OR_1$, $SR_1$, $NR_1R_2$, $C(=NH)NR_1R_2$, $NHC(=NH)NR_1R_2$, $CH=O$, $C(=O)OH$, $C(=O)NR_1R_2$, $CH(NH_2)(C(=O)OH)$; aryl and aralkyl groups that are optionally substituted with one or more halogens, OH, SH, $SCH_3$, $NR_1R_2$; adamantyl; $NR_1R_2$; heterocycle; purine; pyrimidine; phosphate; polyether; polyethylene glycol or metal coordination groups.

Alkyl, alkenyl, and alkynyl groups according to the invention include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups.

Aryl groups according to the invention include but are not limited to substituted and unsubstituted aromatic hydrocarbyl groups such as phenyl and naphthyl groups. Aralkyl groups include but are not limited to groups having both aryl and alkyl functionality, such as benzyl and xylyl groups.

Metal coordination groups according to the invention include but are not limited to hydroxamic acids, catecholamide, acetylacetone, 2,2'-bipyridine, 1,10-phenanthroline, diacetic acid, pyridine-2-carboxamide, isoalkyldiamine, thiocarbamato, oxalate, glycl, histidyl and terpyridyl. Other metal coordination groups are known, as for example see Mellor, D. P., *Chemistry of Chelation and Chelating Agents in International Encyclopedia of Pharmacology and Therapeutics,* Section 70, The Chelation of Heavy Metals, Levine, W. G. Ed., Pergamon Press, Elmford, N.Y., 1979.

Solid supports according to the invention include controlled pore glass (CPG), oxalyl-controlled pore glass (see, e.g., Alul, et al., *Nucleic Acids Research* 1991, 19, 1527), TentaGel Support—an aminopolyethyleneglycol derivatized support (see, e.g., Wright, et al., *Tetrahedron Letters* 1993, 34, 3373) or Poros—a copolymer of polystyrene/divinylbenzene.

A number of substituent groups can be introduced into compounds of the invention in a protected (blocked) form and subsequently de-protected to form a final, desired compound. In general, protecting groups render chemical functionality inert to specific reaction conditions and can be appended to and removed from such functionality in a molecule without substantially damaging the remainder of the molecule. See, e.g., Green and Wuts, Protective Groups in Organic Synthesis, 2d edition, John Wiley & Sons, New York, 1991. For example, amino groups can be protected as phthalimido groups or as 9-fluorenylmethoxycarbonyl (FMOC) groups and carboxyl groups can be protected as fluorenylmethyl groups. Representative hydroxyl protecting groups are described by Beaucage, et al., *Tetrahedron* 1992, 48, 2223.

Substituent groups according to the invention include but are not limited to halogen (Cl, Br, F), hydroxyl (OH), thiol (SH), keto (C=O), carboxyl (COOH), ethers, thioethers, amidine (C(=NH)$NR_3R_4$), guanidine (NHC(=NH)$NR_3R_4$, glutamyl CH($NR_3R_4$)(C(=O)$OR_5$), nitrate ($ONO_2$), nitro ($NO_2$), nitrile (CN), trifluoromethyl ($CF_3$), trifluoromethoxy ($OCF_3$), O-alkyl, S-alkyl, NH-alkyl, N-dialkyl, O-aralkyl, S-aralkyl, NH-aralkyl, amino ($NH_2$), azido ($N_3$), hydrazino ($NHNH_2$), hydroxylamino ($ONH_2$), sulfoxide (SO), sulfone ($SO_2$), sulfide (S—), disulfide (S—S), silyl, heterocyclic, alicyclic and carbocyclic. Preferred substituents include halogens, alcohols and ethers (OR$_1$), thiols and thioethers (SR$_2$), amines (NR$_3$R$_4$), amidines [C(=NH)NR$_3$R$_4$], guanidines [NHC(=NH)NR$_3$R$_4$], aldehydes (CH=O), acids [C(=O)OH], esters [C(=O)OR$_5$], amides [C(=O)NR$_3$R$_4$] and glycine [CH(NH$_2$)(C(=O)OH)].

Particularly preferred functional groups according to the invention include monomeric units of at least the following specific functional moieties: thymine, uracil, adenine, guanine, cytosine imidazole, carbazole, aminoethyl, carboxyethyl, phenyl, short and long chain alkyls, and glycine. Other preferred functional groups include amino, benzyl, and tetraethylene glycol groups.

The compounds of the invention can include conjugate groups covalently bound to primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, phospholipids, biotin, phenanthroline, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992, U.S. patent application Ser. No. 116,801, filed Sep. 3, 1993, and U.S. Pat. No. 5,218,105. Each of the foregoing is commonly assigned with this application. The entire disclosure of each is incorporated herein by reference.

Monomeric compounds of the invention can be used to prepare oligomeric compounds having either preselected sequences or sequences determined via combinatorial strategies. One useful combinatorial strategy is the above-noted SURF strategy, which is disclosed and claimed in U.S. patent application Ser. No. 749,000, filed Aug. 23, 1991, PCT Application US92/07121, filed Aug. 21, 1992, and U.S. patent application Ser. No. 357,396, filed Dec. 16, 1994, all of which are commonly assigned with this application. The entire disclosure of these applications are herein incorporated by reference.

To synthesize a combinatorial library having a large degree of chemical diversity is an important aspect of the present invention. Chemical diversity is introduced at one level by varying the nature of the phosphorus likage. Phosphorus linkages amenable to the present invention include phosphodiester (OPO), phosphorothioate (OPS), phosphoramidate (OPN), phosphorothioamidate (SPN), and alkylphosphonate (OPC). The combinatorial library can be prepared with a single type of phosphorus linkage, or with different linkages at each position of the oligomer. For example, a single OPS linkage can be selectively introduced at any position in a OPO oligomer. In fact, all possible combinations of OPO, OPS, OPN, SPN and OPC linkages can be introduced selectively into the oligomers. The presence or absence of a type of linkage at a particular position in an oligomer may have a profound effect on the properties of the molecule.

In the case of phosphoramidate linked libraries, a further level of diversity is possible due to the ability to have substituents on the nitrogen atom of the OPN linkage. Thus it is possible to introduce a wide variety of amines each time a OPN linkage is present in an oligomer. It is possible to have the same amine substituents at each OPN linkage or a different amine at each position.

As was discussed earlier, chemical diversity can be generated at several levels in SURF libraries. We have described above the preparation of a large number of monomers. These monomers have been prepared to explore two aspects of chemical diversity: first a wide number of functional groups are available, covering a range of chemical properties. Second, these functional groups are attached to different linker portions designed to display, or present them in space in different ways, allowing variable flexibility. The following section describes a third level of diversity, the inter-residue linkage itself. It is to be understood that the methods used to introduce any of the linkage types are compatible. Specifically, by using the proper conditions, it is possible to introduce phosphate linkages including OPO, OPS, OPN, SPN and OPC linkages at will at any position in an oligomer, independently of the sequence of the oligomer. This is possible because the chemical reaction which defines the nature of the linkage is separate from the attachment of the monomer to the reactive group on the solid support (whether linker or the previous monomer) . Specifically, when a phosphoramidite monomer is treated with tetrazole and added to the solid support which has a free hydroxyl group, a phosphite triester is obtained. This phosphite triester can then be treated with Iodine (formulated in the same way as for DNA synthesis on an automated synthesizer), giving a phosphodiester after ammonia deprotection. Alternatively, the phosphite triester can be treated with benzodithiole-3-one-1,1-dioxide to give the corresponding phosphorothioate.

Hydrogen phosphonate chemistry has the advantage of allowing additional chemical modifications to be introduced into oligomers. Oligonucleotide phosphodiesters and phosphorothioates have been prepared using this approach, (see Froehler, B. C., Matteucci, M. D. *Tetrahedron Lett.* 1986, 27, 469–472), as well as oligonucleotide phosphoramidates (see Froehler, B. C. *Tetrahedron Lett.* 1986, 27, 5575–5579. Letsinger, R. L., Singman, C. N., Histand, G., Salunkhe, M. *J. Am. Chem. Soc.* 1988, 110, 4470–4471. The synthesis of oligomers containing both phosphodiesters and phosphoramidates was reported, as well as the use of phosphoramidite chemistry in conjunction with the synthesis of phosphoramidates (see Jung, P. M., Histand, G., Letsinger, R. L. *Nucleosides & Nucleotides,* 1994, 13, 1597–1605). In this latter work, alternating phosphodiester and phosphoramidate oligomers were prepared by coupling phosphoramidites and H-phosphonates to the growing oligomer, followed by the appropriate oxidation step. In general, however, all the examples described thus far have incorporated the same amine substitution at all phosphoramidate linkages in the oligomer. These studies have shown the feasibility of using the phosphoramidate bond as an additional site for the incorporation of diverse functional groups. A wide variety of amines can be used in the oxidative step, and the monomers of the present invention support the necessary chemistry. Thus, for the preparation of combinatorial libraries incorporating phosphoramidate linkages, the monomers of the present invention are converted to the corresponding H-phosphonate monoesters. In one aspect of the present invention this is accomplished using PCl$_3$ and imidazole as the phosphitylating reagent (see Garegg, P. J., Regberg, T., Stawinski, J., Strömberg, R. *Chem. Scr.* 1986, 26, 59–62). These H-phosphonates monomers are oligomerized on solid support by activation with pivaloyl chloride, adamantoyl chloride or other appropriate activating agent. The intermediate H-phosphonate diesters are oxidized to the phosphate diesters in high yields using iodine in aqueous pyridine. This allowed for the comparison of the coupling efficiency of the H-phosphonate and phosphoramidite methods. Essentially the same coupling efficiency is achieved with both methodologies. The H-phosphonate diesters are converted to phosphoramidates by the use of a 10% solution of the appropriate amine in pyridine/$CCl_4$ (1:1). Under these conditions, a H-phosphonate diester is oxidized to a phosphoryl chloride via an Arbuzov reaction, followed by displacement of the chloride by a primary or secondary amine. The second step has proven to be quite general, with a wide variety of amines giving satisfactory yields. Moreover, the yield of phosphoramidate is comparable to the yield of phosphodiester.

Several types of libraries are available through this methodology. The simplest kind is a library made from a set of monomers of the present invention (a set of 4 to 16 or more monomers is typically used) of 2 to 10 or more monomer units in length, which is substituted at phosphorus with a single amine. These libraries are prepared by split bead synthesis, following the H-phosphonate synthesis protocol rather than phosphoramidite chemistry. The intermediate H-phosphonate diesters are left intact until the final step. At that point the oligomer library pools are oxidized with $CCl_4$/Pyridine containing 10% of the appropriate primary or secondary amine. This has the result of converting all the interresidue linkages to phosphoramidates. The library therefore is composed of all possible sequences of the monomers, separated into subsets unique at a fixed position, linked together by a constant phosphoramidate linkage. It should be evident that the final properties of the library will be determined by the choice of amine used in the oxidation step. Thus, water solubility, pharmacokinetics and pharmacodynamics of the library components can be modulated by the choice of amine. It is also possible to prepare oligomer libraries with mixed linkages by having an intermediate oxidation step (see Gryaznov, S. M., Sokolova, N. I. *Tetrahedron Lett.* 1990, 31, 3205–3208; Gryaznov, S. M., Potapov, V. K. *Tetrahedron Lett.* 1991, 32, 3715–3718; Farooqui, F., Sarin, P. S., Sun, D., Letsinger, R. L. *Bioconjugate Chem.*, 1991, 2, 422–426; Iso, Y., Yoneda, F., Ikeda, H., Tanaka, K., Fuji, K. *Tetrahedron Lett.* 1992, 33, 503–506). Thus, a portion of the oligomer library is synthesized by H-phosphonate chemistry, which can be oxidized with ($R_2NH$, $CCl_4$/Py or $S_8$, $CS_2$/TEA or $H_2O$, $CCl_4$/Py), and a second portion of the library synthesized and oxidized with a second set of reagents. This creates a chimeric library, where a segment of the random oligomers in each subset has a different linkage than the rest of the molecule. By extension of this methodology, it is possible to incorporate a different linkage at each position of the oligomer library by having a different oxidation step after each monomer coupling. The linkage can be combinatorialized by performing a separate oxidation on a portion of the H-phosphonate diester-linked solid support, followed by pooling of the subsets in the same way that the monomer positions are randomized. Thus, each monomer and the linkage between them can be randomized by a split synthesis strategy.

Illustrative of the SURF strategy is a 2'-O-methyl oligonucleotide library (see, Ecker et. al., ibid.) shown in Table I, below. Table I describes the selection of a 2'-O-methyl oligonucleotide for binding to an RNA hairpin. The $K_D$'s, i.e., the binding constants, were determined by gel shift. "X" is used to indicate the position being varied and underlining is used to indicate positions that become fixed during successive iterations of the SURF strategy.

TABLE I

| Subsets | $K_D$ (mM) | | | |
|---|---|---|---|---|
| | X = A | X = C | X = G | X = T |
| Round 1 NNNNXNNNN | 22 | <u>10</u> | >100 | >100 |
| Round 2 NNNN<u>C</u>NXNN | >10 | <u>4</u> | >10 | >10 |
| Round 3 NNXN<u>C</u>N<u>C</u>NN | >10 | <u>0.5</u> | >10 | >10 |
| Round 4 NN<u>CX</u><u>C</u>N<u>C</u>NN | >10 | <u>0.15</u> | >10 | >10 |
| Round 5 NN<u>CCC</u>XCNN | <u>0.08</u> | >1 | 0.4 | >1 |
| Round 6 NN<u>CCCAC</u>XN | <u>0.05</u> | >0.5 | 0.08 | >0.5 |
| Round 7 NX<u>CCCACAN</u> | >0.1 | >0.1 | <u>0.03</u> | >0.1 |
| Round 8 NG<u>CCCACAX</u> | 0.05 | <u>0.02</u> | 0.05 | 0.04 |
| Round 9 XG<u>CCCACAC</u> | 0.03 | 0.05 | 0.02 | <u>0.01</u> |

This SURF strategy has not been used for libraries except those that employ naturally-occurring nucleotides as phosphodiesters or phosphorothioates as monomeric units. Other combinatorial strategies have only been used for libraries that employ amino acids as monomeric units.

One aspect of the present invention is the inclusion of monomeric compounds having structure I in the above-described SURF strategy. The functional groups appended to these monomeric compounds can be incorporated into the libraries while retaining the advantages of automated phosphoramidite oligomer synthesis. These functional groups can effect interactions of the following types: hydrogen-bond donor and acceptor, ionic, polar, hydrophobic, aromatic, and electron donors and acceptors. Preferred functional groups include aminoethyl, carboxyethyl, adenylmethyl, thyminylmethyl, imidazolylmethyl, benzyl, myristyl, isopropyl, and tetraethylene glycol groups.

One advantage of the present invention is that the simple design of monomeric compounds of the invention allows for combining rational drug design with screen mechanisms for thousands of compounds. This is achieved by using the compounds of the invention in a combinatorial technique such as the SURF strategies.

In one preferred embodiment, functional groups appended to the monomeric compounds of the invention are selected for their potential to interact with, and preferably inhibit, the enzyme $PLA_2$. Thus, the compounds of the invention can be used for topical and/or systematic treatment of inflammatory diseases including atopic dermatitis and inflammatory bowel disease. In selecting the functional groups, advantage can be taken of $PLA_2$'s preference for anionic vesicles over zwitterionic vesicles. In selecting the backbone that bears these functional groups, further advantage can be taken of fact that the natural substrate of $PLA_2$ contains a phosphate group. Therefore, phosphodiester or phosphorothioate and other phosphate linked oligomers preferably are selected, providing a negatively charged compound for binding with the positively charged interfacial binding site of $PLA_2$.

Certain compounds of the invention include aromatic functional groups to facilitate binding to the cleft of the $PLA_2$ enzyme. (see, Oinuma, et al.,*J. Med. Chem.* 1991, 34, 2260; Marki, et al., *Agents Actions* 1993, 38, 202; and Tanaka, et al., *J. Antibiotics* 1992, 45, 1071). Benzyl and 4-hexylbenzyl groups are preferred aromatic groups. The compounds of the invention can further include hydrophobic functional groups such as tetraethylene glycol groups. Since the PLA$_2$ enzyme has a hydrophobic channel, hydrophobicity is believed to be an important property of inhibitors of the enzyme.

In certain embodiments of the invention, phosphoramidite monomeric compounds having structure I are incorporated into libraries of oligomeric compounds and increasingly less complex subsets of oligomers are identified in combinatorial screening techniques such as the above-described SURF technique by successive rounds of screens. In one preferred embodiment, a library of oligomeric compounds functionalized with aminoethyl, carboxyethyl, adenylmethyl, thyminylmethyl, tetraethylene glycol, imidazolylmethyl, benzyl, isopropyl, myristyl or 4-hexylbenzyl groups are prepared and assayed for inhibition of PLA$_2$ activity. The PLA$_2$ assay can be effected using a combinatorial screening strategy such as the SURF strategy. For this assay, the oligomer libraries are screened for inhibition of human type II PLA$_2$ enzymatic activity. Typically, these libraries contain about 8000 different compounds. Successive iterations of the SURF technique is effected to select unique oligomers from the library. The libraries additionally can be screened in other in vitro assays to determine further mechanisms of inhibition.

Upon identification of oligomers in a first phase of screening, further modifications can be made to the contents of the oligomer libraries. For example, if a first iteration of screening results in an active compound that contains a benzyl group, then in subsequent iterations of the screen this aromatic residue can then be varied using substituted benzyl groups. In this way, structural activity is identified in a stepwise manner to define potent inhibitors of the enzymatic activity.

To maximize the identification of a tight binding oligomeric inhibitor of PLA$_2$ via a combinatorial approach, an array of functional groups typically are included in a randomized library. The oligomers are assembled in a manner analogous to oligonucleotide synthesis by the coupling of monomeric, phosphoramidate units wherein the normal nucleotide structure is replaced by more diverse chemical groups. In some of the monomeric units, the nucleobases of nucleotides have been retained. In other, the nucleobases are replaced with other functional groups selected to provide different ligand-ligand interactions than that provided by the nucleobases. The sugar moiety of a normal nucleotide is replaced by an alkylene glycol unit, e.g., an ethylene glycol unit, to form a unique backbone. This methodology provides for a convergent preparation of a large number of monomers bearing a wide variety of functional groups. Where necessary, functional groups are protected with base labile protecting groups to allow one-step deprotection of the oligomer upon completion of the synthesis.

As noted above, monomeric compounds having structure I can be linked with one another to form homopolymeric structures or they can be linked with nucleotides and/or other moieties to form heteropolymeric structures. For example, chimeric structures can be formed that include one or more regions or "stretches" of the monomeric units of invention joined to one or more regions or "stretches" of naturally occurring or synthetic oligonucleotides or to other synthetic or natural polymeric compounds such as peptides, peptoids, peptide nucleic acids, oligo and/or polysaccharides. Further, oligomeric compounds having structure II can be incorporated into chimeric structures along with the compounds disclosed in the patent application entitled "Oligonucleotide Mimics Having Nitrogen-Containing Linkages," bearing attorney docket ISIS-1014, and the patent application entitled "Pyrrolidine-Containing Monomer and Oligomers," bearing attorney docket ISIS-1237. The foregoing patent applications are filed concurrently with this application, are commonly assigned, and are incorporated herein by reference.

In the combinatorial synthesis of oligomeric compounds of the invention, the monomers are incorporated into libraries, including libraries suitable for screening for PLA$_2$ inhibition. The libraries are further useful for screening against other targets of interest. In non-combinatorial synthesis of oligomeric compounds of the invention, the monomeric units are combined in a predetermined sequences using the standard conditions normal used for oligonucleotide synthesis.

To detect an active sequence generated via a combinatorial technique, the concentration of the active molecule is selected to be of sufficiently great that the molecule can be detected within the sensitivity of the chosen assay. As will be recognized, the number of unique oligomer sequences within a subset produced via a combinatorial technique depends on the length of the oligomer and the number of different monomers employed. The number of sequences can be determined by raising the number of monomers to a power equal to the number of random positions. This is illustrated in Table II. Table II also indicates the concentration of each sequence when the subset concentration is 100 $\mu$M, a typical high-test concentration. We have found that the number of monomers and their length can be based upon an estimate of the expected IC$_{50}$ (i.e., a concentration at which 50% of enzyme activity is inhibited) that is desirable in a final oligomeric compound. For an expected IC$_{50}$ of 100 nM, the complexities shown in Table II are acceptable, that is, the libraries shown in Table II have complexities that would allow detection of a unique sequence with an IC$_{50}$ of about 100 nM or less.

TABLE II

Complexity of Libraries

| Length | Sequences Per Subset | nM Each Sequence At 100 $\mu$M Subset |
|---|---|---|
| 5 Monomers | | |
| 4-mer | 125 | 800 |
| 5-mer | 625 | 160 |
| 6 Monomers | | |
| 4-mer | 216 | 463 |
| 5-mer | 1,296 | 77 |
| 7 Monomers | 343 | 291 |
| 4-mer | | |
| 8 Monomers | 512 | 195 |
| 4-mer | | |
| 10 Monomers | 1,000 | 100 |
| 4-mer | | |

If five monomers are selected for a library, then the library will have a length of five monomer units, XNNNN, where N is an equal molar mixture of monomer units and X is a different monomer unit in each of the five subsets. For ease in synthesis, the fixed position can be selected as the right end of the molecule. After assay for inhibition of PLA$_2$ activity as described below, position X is fixed with the residue giving the greatest inhibition and the next subset is synthesized and screened. The fixed position then shifts towards the left end of the oligomer as unrandomization proceeds. Five rounds of synthesis and screening are required to determine a unique inhibitor.

The monomer units of the invention are linked to form oligomeric compounds using standard phosphoramidite chemistry that is used for standard synthesis of oligonucleotides. Since the coupling rates of functionalized alkylene glycol monomers may vary, the reactivity of the individual monomers can adjusted such that equal molar incorporation of each monomer at each randomized position is effected. Adjusting for the reactivity of the monomers can be effected as in the examples below. A further technique for effecting such adjustment is disclosed in the United States patent application entitled "Random Oligonucleotide Libraries And Methods Of Making The Same," bearing attorney docket ISIS-1009. The foregoing patent application is being filed concurrently with this application, is commonly assigned, and is incorporated herein by reference.

In a SURF screening strategy the amount of oligomer is selected such that the concentration of each subset in the initial round of screening is relatively high (about 100 $\mu$M). It is presently preferred to synthesize oligomers using a DNA synthesizer. On such synthesizers the oligomers are most conveniently synthesized on a 1 to 4 $\mu$mol scale. Given the concentration of a subset of libraries at about 100 $\mu$m, the assays preferably are performed in a small volume of less than about 200 $\mu$L.

Exemplary compounds of the invention are illustrated in the following examples, which are not intended to be limiting.

EXAMPLE 1

1-(1-Thymine)-2,3-propandiol

To a stirred solution of thymine (4.2 g, 33 mmol) in dry dimethylformamide (DMF, 30 ml) was added R-(+)-glycidol (2.2 g, 30 mmol), and potassium carbonate (50 mg, 0.36 mmol). The suspension was heated to 80° C. for five hours then evaporated. The products were diluted with methanol (25 ml) and filtered. The filtrate was evaporated and the residue purified by silica gel column chromatography. Elution with ethyl acetate:methanol (9:1, v/v), pooling of appropriate fractions, and evaporation furnished the N(1) substituted material free from N(1),N(3) disubstituted material to yield 3.08 g (60%). $^1$H NMR (DMSO-d$_6$): $\delta$, 1.8 (s, 3, CH$_3$); 3.35 (bm, 3, C$\underline{H}$OHC$\underline{H}_2$OH); 3.7 and 3.9 (2 m, 2, NCH$_2$); 4.7 (bs, 1, CH$_2$O$\underline{H}$, exchanges with D$_2$O); 5.0 (bs, 1, CHO $\underline{H}$, exchanges with D$_2$O); 7.4 (s, 1, H-6); 11.2 (bs, 1, NH, exchanges with D$_2$O). Anal. calcd. for C$_8$H$_{12}$N$_2$O$_4$ (200.193): 47.99% C, 6.04% H, 13.99% N; found: 47.35% C 6.10% H, 13.67% N.

EXAMPLE 2

1-(1-Thymine)-3-O-dimethoxytrityl-2-propanol

To a stirred solution of 1-(1-thymine)-2,3-propandiol (2.079 g, 12.4 mmol) in dry pyridine (30 ml) was added 4,4'-dimethoxytrityl chloride (4.4 g, 13 mmol). The suspension was stirred at room temperature for four hours. The reaction mixture was evaporated and the residue purified by silica gel column chromatography. Elution with ethyl acetate:hexane:triethylamine (3/2/1, v/v/%), pooling of appropriate fractions, and evaporation gave a yield of 3.39 g (54%). $^1$H NMR (DMSO-d$_6$): $\delta$, 1.8 (s, 3, CH$_3$); 2.9 (m, 2, CH$_2$ODMT); 3.8 (s, 6, OCH$_3$); 3.9 (m, 2, NCH$_2$); 5.3 (d, 1, OH, exchanges with D$_2$O); 6.9 (m, 4, trityl); 7.3 (m, 9, trityl); 11.2 (s, 1, NH, exchanges with D$_2$O).

EXAMPLE 3

1-(1-Thymine)-3-O-dimethoxytrityl-2-O-[(N,N-diisopropylamino)-2-cyanoethoxyphosphite]propane A stirred solution of 1-(1-thymine)-3-O-dimethoxytrityl-2-propanol (3.39 g, 6.7 mmol) and N,N-diisopropylethylamine (2.4 ml, 14 mmol) in dry THF (35 ml) was cooled to 10° C. in an ice bath. Chloro-β-cyanoethoxy-N,N-diisopropylaminophosphine (1.5 ml, 6.7 mmol) was added. After stirring at room temperature for four hours the reaction mixture was evaporated and the residue purified by silica gel column chromatography. Elution with ethyl acetate:hexane:triethylamine (1:1:1, v/v/%), pooling of appropriate fractions, and evaporation gave a yield of 2.78 g (61%). $^1$H NMR (CD$_3$CN): $\delta$, 1.2 (m, 12, 6 CH$_3$) 1.75 (d, 3, CH$_3$); 2.45 and 2.6 (2 t, 2, CH$_2$ODMT); 3.8 (d, 6, OCH$_3$); 6.9 and 7.3 (2 m, 14, trityl); 9.3 (bs, 1, NH, exchanges with D$_2$O). $^{31}$P NMR (CD$_3$CN); $\delta$, 150.19 and 150.66. Anal. calcd. for C$_{38}$H$_{47}$N$_4$O$_7$P (702.786): 64.94% C, 6.74% H, 7.97% N; found: 64.60% C, 6.91% H, 7.80% N.

EXAMPLE 4

1-(1-Imidazole)-2,3-propandiol

A rapidly stirred solution of imidazole (13.6 g, 0.2 mole) in DMF (250 mL) was treated with powdered potassium carbonate (12 g) and heated to 70° C. for 30 min. To this solution was added glycidol (14.8 g, 0.2 mole) in one portion and the mixture stirred at this temperature for 36 hr. The resulting yellow suspension was filtered and the filtrate was rotary evaporated to afford a clear red syrup. The syrup was coevaporated with acetonitrile (100 mL) and then flash-chromatographed on a 10.5×10 cm silica gel column. A step gradient elution of ethyl acetate-methanol (9:1, 2L then 4:1, 2L) gave the imidazole product as an amorphous solid, 16 g, (56%). $^1$H NMR (DMSO-d6): $\delta$, 7.55, 7.10 and 6.84 (3 s, 3, imidazole); 5.08 (d, 1, CHO$\underline{H}$, exchanges with D$_2$O); 4.85 (t, 1, CH$_2$O$\underline{H}$, exchanges with D$_2$O); 4.05 and 3.83 (2 dd, 2, CH$_2$); 3.55 (m, 1, methine) ; 3.30 and 3.18 (2 m, 2, C $\underline{H}_2$OH). Anal. calcd. for C$_6$H$_{10}$N$_2$O$_2$ (142.157): 50.69% C, 7.09% H, 19.71 % N; found: 50.59% C, 7.07% H, 19.59% N.

EXAMPLE 5

1-(1-Imidazole)-3-O-dimethoxytrityl-2-propanol

To a stirred solution of 1-(1-imidazole)-2,3-propandiol (1.0 g, 7.0 mmol) in dry pyridine (15 ml) and dry DMF (15 ml) was added 4,4'-dimethoxytrityl chloride (2.61 g, 7.7 mmol). The suspension was stirred at room temperature for four hours. An additional equivalent of the trityl compound was added (2.61 g, 7.7 mmol). Stirring was continued for an additional 23 hours and the mixture was evaporated. The residue was purified by silica gel column chromatography. Elution with methanol:ethyl acetate:triethylamine (1/19/1, v/v/%), pooling of appropriate fractions, and evaporation gave a yield of 432 mg (14%). $^1$H NMR (DMSO-d$_6$): $\delta$, 2.78, 2.95 (2 m, 1, CH$_2$ODMT); 3.7 (s, 6, 2 OCH$_3$); 3.85 (bm, 1, C$\underline{H}$OH); 3.95 and 4.1 (2 m, 2, NCH$_2$); 5.25 (d, 1, OH, exchanges with D$_2$O); 6.7 to 7.5 (m, 13/3, DMT/imidazole).

EXAMPLE 6

1-(1-Imidazole)-3-O-dimethoxytrityl-2-O-[(N,N-diisopropylamino)-2-cyanoethoxyphosphite]propane A solution of 1-(1-imidazole)-3-O-dimethoxytrityl-2-propanol (432 mg, 0.97 mmol) and N-N-diisopropylethylamine (252 mg, 3.5 mmol) in dry DMF (35 ml) was cooled to 5° C. in an ice bath. Chloro-β-cyanoethoxy-N,N-diisopropylaminophosphine (233 mg, 1.1 mmol) was added and the reaction mixture was stirred at room temperature for one half hour. The reaction mixture was evaporated and the residue purified by silica gel column chromatography. Elution with ethyl acetate:hexane:triethylamine (7/3/1, v/v/t), pooling of appropriate fractions, and evaporation gave a yield of 498 mg (80%). 1H NMR (CD$_3$CN); δ, 0.9 to 1.2 (m, 12, CH$_3$); 3.8 (d, 6, OCH$_3$); 6.75 to 7.5 (M, 13/3, ODMT/imidazole). $^{31}$P NMR (CD$_3$CN) ; δ, 149.83 and 150.68.

EXAMPLE 7

1-(1-Carbazole)-2,3-propandiol

A rapidly stirred solution of carbazole (14 g, 83 mmole) and R-(+)-glycidol (6.20 g/83 mmol) in anhydrous DMF (300 mL) was treated with powdered potassium carbonate (2.3 g) and the mixture heated to 70° C. for 18 hr. The resulting yellow suspension was filtered and then rotary evaporated to afford a yellow syrup. The syrup was coevaporated with acetonitrile (100 mL) and then flash-chromatographed on a 10.5×10 cm silica gel column. Elution with ethyl acetate gave the carbazole product as an amorphous solid, 8.25 g, (41%). $^1$H NMR (DMSO-d$_6$): δ, 8.13, 7.60, 7.23 and 7.10 (4 m, 8, carbazole); 5.03 and 4.90 (2 s, 2, hydroxyls, exchange with D$_2$O); 4.47 and 4.27 (2 dd, 2, CH$_2$); 3.90 (m, 1, methine); 3.40 (m, 2, CH$_2$OH) . Anal. calcd. for C$_{15}$H$_{15}$NO$_2$ (241.289): 74.66% C, 6.27% H, 5.80% N; found: 74.32% C, 6.25% H, 5.76% N.

EXAMPLE 8

1-(1-Carbazole)-3-O-dimethoxytrityl-2-propanol

To a solution of 1-(1-carbazole)-2,3-propandiol (1.1 g, 4.5 mmol) in dry pyridine (40 ml) was added 4,4'-dimethoxytrityl chloride (1.54 g, 4.5 mmol). The reaction mixture was stirred at room temperature for three hours and evaporated. The residue was purified by silica gel column chromatography. Elution with ethyl acetate:hexane:triethylamine (1/9/1, v/v/%), pooling of appropriate fractions, and evaporation gave a yield of 976 mg (39%). $^1$H NMR (DMSO-d$_6$); δ, 2.9 to 3.1 (2 m, 2, CH$_2$ODMT); 3.7 (s, 6, 2 OCH$_3$); 4.1 (m, 1, CHOH); 4.3 to 4.5 (2 m, 2, NCH$_2$); 5.2 (d, 1, OH, exchanges with D$_2$O); 6.8 to 8.2 (m, 21, carbazole and trityl) . Anal. calcd. for C$_{36}$H$_{33}$NO$_4$ (543.661): 79.53% C, 6.12% H, 2.58% N; found: 79.28% C, 6.34% H, 2.70% N.

EXAMPLE 9

1-(1-Carbazole)-3-O-dimethoxytrityl-2-O-[(N,N-diisopropylamino)-2-cyanoethoxyphosphite]propane Chloro-β-cyanoethoxy-N,N-diisopropylaminophosphine (403 mg, 1.7 mmol) was added to a solution of 1-(1-carbazole)-3-O-dimethoxytrityl-2-propanol (916 mg, 1.7 mmol) and N,N-diisopropylethylamine (445 mg, 3.4 mmol) in dry THF (40 ml) at 5° C. At four hours the reaction mixture was evaporated and the residue was purified by silica gel column chromatography. Elution with ethyl acetate:hexane:triethylamine (1/19/1, v/v/%), pooling of appropriate fractions, and evaporation gave a yield of 850 mg (68%). $^1$H NMR (CD$_3$CN); δ, 0.7 to 1.05 (3 d, 12, CH$_3$); 3.75 (d, 6, OCH$_3$); 6.7 to 8.1 (m, 21, carbazole and trityl). $^{31}$P NMR (CD$_3$CN); δ, 149.1 and 149.5. Anal. calcd. for C$_{45}$H$_{50}$N$_3$O$_5$P (743.881): 72.66% C, 6.77% H, 5.65% N; found: 72.62% C, 6.76% H, 5.61% N.

EXAMPLE 10

1-(1-Uracil)-2,3-propandiol

Uracil (21.56 g, 192 mmol) is dissolved in dry DMF (500 ml) with heating and R-(+)-glycidol (15.1 g, 203 mmol) is added. The suspension is heated to 70° C. At four hours the reaction is evaporated and the residue purified by silica gel column chromatography. Elution with ethyl acetate:methanol (19/1, v/v), pooling of appropriate fractions and evaporation gave a yield of 15.62 g (44%). $^1$H NMR (DMSO-d$_6$); δ, 3.35 (m, 3, CHOHCH$_2$OH); 3.7 and 3.9 (2 m, 2, NCH$_2$); 5.5 (m, 1, H-5); 7.5 (d, 1, H-6); 11.2 (bs, 1, NH).

EXAMPLE 11

1-(1-Uracil)-3-O-dimethoxytrityl-2-propanol

Dimethoxytritylchloride (29.8 g, 88 mmol) is added to a solution of 1-(1-uracil)-2,3-propandiol (15.62 g, 84 mmol) in dry pyridine (150 ml). The reaction mixture is stirred at room temperature for twenty two hours and evaporated. The residue was purified by silica gel column chromatography. Elution with ethyl acetate:hexane:triethylamine (3/2/1, v/v/%), pooling of appropriate fractions, and evaporation gave a yield of 1.1 g (4%). $^1$H NMR (DMSO-d$_6$); δ, 2.8 to 3.0 (2 m, 2, CH$_2$ODMT); 3.7 (s, 6, 2 OCH$_3$); 3.85 (m, 1, C HOH); 3.95 (m, 2, NCH$_2$); 5.3 (d, 1, CHOH, exchanges with D$_2$O); 5.41 (d, 1, H-5); 6.85 (d, 4, trityl); 7.3 and 7.4 (2 m, 10, H-6 and trityl); 11.2 (s, 1, NH, exchanges with D20).

EXAMPLE 12

1-(1-Uracil)-3-O-dimethoxytrityl-2-O-[(N,N-diisopropylamino)-2-cyanoethoxyphosphite]propane A stirred solution of 1-(1-uracil)-3-O-dimethoxytrityl-2-propanol (598 mg, 1.2 mmol) and N,N-diisopropylethylamine (158 mg, 1.2 mmol) in dry THF (35 ml) was cooled to 10° C. in an ice bath. Chloro-β-cyanoethoxy-N,N-diisopropylaminophosphine (286 mg, 1.2 mmol) was added. After stirring at room temperature for four hours the reaction mixture is evaporated and the residue purified by silica gel column chromatography. Elution with ethyl acetate:hexane:triethylamine (1:1:1, v/v/%), pooling of appropriate fractions, and evaporation gave a yield of 368 mg (42%) . $^1$H NMR (CD$_3$CN); δ, 1.2 (m, 12, CH$_3$); 2.45 and 2.6 (2 t, 2, CH$_2$ODMT); 3.8 (d, 6, OCH$_3$); 6.9 and 7.3 (2 m, 15, trityl and H-6); 9.3 (bs, 1, NH, exchanges with D$_2$O). $^{31}$P NMR (CD$_3$CN); δ, 154.88 and 155.2.

EXAMPLE 13

1-[9-(N6-Benzoyl)adenine]-2,3-propandiol

To a stirred solution of adenine (30.0 g, 0.22 mol) in dry DMF (500 ml) was added R-(+)-glycidol (22.0 ml, 0.33 mol), and potassium carbonate (7.6 g, 55 mmol). The suspension was heated to 85° C. for 20 hours then concentrated. The residue was purified by crystallization from methanol to yield 18.1 g (39%) of the intermediate 1-(9-adenine)-2,3-propandiol. $^1$H NMR (DMSO-d$_6$); δ, 3.3 to 3.4 (m, 2, CH$_2$OH) ; 3.8 to 3.9 (m, 1, CHOH) ; 3.9 to 4.1 and 4.3 to 4.4 (2m, 2, NCH$_2$) ; 4.8 to 4.9 (t, 1, CH$_2$OH, exchanges with D$_2$O); 5.1 to 5.2 (d, 1, CHOH, exchanges with D$_2$O); 7.3 (s, 2, NH$_2$, exchanges with D$_2$O); 8.0 and 8.1 (2s, 2, C(2)-H, C(8)-H). Anal. calcd. for C$_8$H$_{11}$N$_5$O$_2$ (209.207): 45.93% C, 5.30% H, 33.48% N; found: 45.81% C, 5.42% H, 32.93% N.

To a suspension of 1-(9-adenine)-2,3-propandiol (18.0 g, 86.0 mmol) at 0° C. was added chlorotrimethylsilane (32.7 ml, 257 mmol) . After 15 minutes benzoyl chloride (30.0 ml, 259 mmol) was added and the mixture was stirred at room temperature for 3 hours. The mixture was cooled to 0° C. and 100 ml cold water was added. After 15 minutes 100 ml cold concentrated ammonium hydroxide was added. After stirring at room temperature for one hour the mixture was evaporated and the residue purified by silica gel column chromatography. Elution with methanol:ethyl acetate (1/10, v/v), pooling of appropriate fractions, and evaporation gave a yield of 4.1 g (14.8%). $^1$H NMR (DMSO-d$_6$): δ, 3.3 to 3.5 (m, 2, C$\underline{H}_2$OH); 3.8 TO 4.0 (m, 1, C$\underline{H}$OH); 4.1 to 4.2 and 4.4 to 4.5 (2m, 2, NCH$_2$); 4.9 to 5.0 (t, 1, CH$_2$O$\underline{H}$, exchanges with D$_2$O); 5.2 to 5.3 (d, 1, CHO$\underline{H}$, exchanges with D$_2$O); 7.4 to 8.2 (2m, 5, benzoyl); 8.4 to 8.8 (2s, 2, C(2)-H, C(8)-H); 11.2 (bs, 1, NH, exchanges with D$_2$O). Anal. Calc. for C$_{15}$H$_{15}$N$_5$O$_3$ (313.315): 57.50% C, 4.82% H, 22.35% N; found: 57.24% C, 4.81% H, 21.97% N.

EXAMPLE 14

1-[9-(N6-Benzoyl)adenine]-3-O-dimethoxytrityl-2-propanol

To a solution of 1-[9-(N6-benzoyl)adenine]-2,3-propandiol (4.0 g, 13 mmol) in anhydrous pyridine (50 ml) was added 4,4'-dimethoxytrityl chloride (4.7 g, 14 mmol). The mixture was stirred at room temperature for 4 hours. Methanol was added (5 ml) and the mixture was evaporated. The residue was purified by silica gel column chromatography. Elution with hexane/ethyl acetate/triethylamine (2/8/.1, v/v/v), pooling of appropriate fractions and evaporation yielded 4.2 g (53%). $^1$H NMR (DMSO-d6): δ, 2.9 to 3.1 (2m, 2, CH$_2$ODMT); 3.7 to 3.8 (s, 6, OCH$_3$); 4.1 to 4.6 (m, 3, NCH$_2$CHOH); 5.4 to 5.5 (d, 1, CHOH, exchanges with D$_2$O); 6.8 to 8.2 (4m, 18, trityl, benzoyl); 8.3 to 8.8 (2s, 2, C(2)—H, C(8)—H) ; 11.2 (bs, 1, NH, exchanges with D$_2$O).

EXAMPLE 15

1-[9-(N6-Benzoyl)adenine]-3-O-dimethoxytrityl-2-O-[(N,N-diisopropylamino)-2-cyanoethoxyphosphite]propane To a solution of 1-[9-(N6-benzoyl)adenine]-3-O-dimethoxytrityl-2-propanol (4.2 g, 6.8 mmol) in anhydrous THF (50 ml) was added diisopropylethylamine (2.9 ml) and chloro-β-cyanoethoxy-N,N-diisopropylaminophosphine (1.5 ml, 6.7 mmol). The mixture was stirred at room temperature for 20 hours. The residue was evaporated and purified by silica gel column chromatography. Elution with hexane/ethyl acetate/triethylamine (2/8/.1, v/v/v), pooling of appropriate fractions, and evaporation gave a yield of 4.54 g (82%). $^1$H NMR (CD$_3$CN); δ, 0.9–1.1 (m, 12, CH3); 2.4 to 2.6 (m, 2, CH$_2$CN); 3 to 3.2 (m, 2, CH$_2$ODMT); 3.4 to 3.7 (m, 3, O$\underline{C}$H$_2$CH$_2$CN, (CH$_3$)$_2$C$\underline{H}$); 3.7 to 3.8 (d, 6, OCH3); 4.3 to 4.6 (m, 3, NC$\underline{H}_2$C$\underline{H}$OH); 6.8 to 7.7 (3m, 18, trityl, benzoyl); 7.9 to 8.8 (2d, 2, C(2)-H, C(8)-H). $^{31}$P NMR (CD$_3$CN); δ, 149.80 and 150.75.

EXAMPLE 16

1-[9-(2-Amino-6-chloro)purine]-2,3-propandiol

To a solution of 2-amino-6-chloropurine (21.3 g, 125 mmol) in 200 ml anhydrous THF was added R-(+)-glycidol (14.0 g, 187 mmol) and potassium carbonate (3.5 g, 25 mmol). The reaction was stirred at 85° C. for 3 hours. The reaction mixture was filtered. The filtrate was evaporated and the residue purified by silica gel column chromatography. Elution with ethyl acetate/methanol (9/1, v/v) pooling of appropriate fractions and evaporation yielded 11.74 g (38%). $^1$H NMR (DMSO-d$_6$); δ, 3.2 to 3.5 (m, 2, C$\underline{H}_2$OH) ; 3.7 to 5.3 (2m, 3, NC$\underline{H}_2$C$\underline{H}$OH); 4.8 to 4.9 (t, 1, CH$_2$O$\underline{H}$, exchanges with D20); 5.2 to 5.3 (d, 1, CHO$\underline{H}$, exchanges with D20); 6.8 to 6.9 (s, 2, NH$_2$, exchanges with D$_2$O); 8.0 (s, 1, C(8)H) . Anal. calcd. for C$_8$H$_{10}$N$_5$O$_2$Cl (243.652): 39.44% C, 4.14% H, 28.74% N; found: 39.41% C, 4.12% H, 28.45% N.

EXAMPLE 17

1-(9-Guanine)-2,3-propandiol

1-[9-(2-Amino-6-chloro)purine]-2,3-propandiol (2.62 g, 11 mmol) is stirred in 1N HCl (aq, 100 ml) at 85° C. for 3 hours. The reaction mixture was cooled in an ice bath and rendered basic with concentrated ammonium hydroxide to pH 10. The product was filtered off as a crystalline solid. Yield was 2.04 g (84%). $^1$H NMR (DMSO-d$_6$); δ, 3.2 to 3.4 (m, 2, C$\underline{H}_2$OH); 3.7 TO 4.2 (M, 3, NC$\underline{H}_2$C$\underline{H}$OH); 4.7 to 4.9 (t, 1, CH$_2$O$\underline{H}$, exchanges with D$_2$O); 5.1 to 5.2 (d, 1, CHO $\underline{H}$, exchanges with D$_2$O); 6.6 (s, 2, NH$_2$, exchanges with D$_2$O); 7.7 (s, 1, C(8)-H); 10.7 (s, 1, NH, exchanges with D$_2$O). Anal. calcd. for C$_8$H$_{11}$N$_5$O$_3$ (225.207): 42.67% C, 4.92% H, 31.10% N; found: 42.28% C, 4.88% H, 30.85% N.

EXAMPLE 18

1-[9-(N2-Isobutyryl)guanine]-2,3-propandiol

To a solution of 1-(9-guanine)-2,3-propandiol (17.0 g, 75.5 mmol) in pyridine (400 ml) at 0° C. was added chlorotrimethylsilane (28.6 ml, 225 mmol). The reaction mixture was stirred for 15 minutes at 0° C. then for 30 minutes at room temperature. The mixture was recooled to 0° C. and isobutyryl chloride (23.7 ml, 226 mmol) was added. The mixture was stirred for 2 hours at room temperature. The reaction was cooled to 0° C. and 100 ml ice cold water was added followed in 15 minutes by 100 ml ice cold ammonium hydroxide. The reaction was stirred at room temperature for 30 minutes, evaporated to near dryness, methanol added to precipitate unwanted byproducts and filtered. The filtrate was evaporated and the residue purified by silica gel column chromatography. Elution with ethyl acetate/methanol (9/1, v/v), pooling of appropriate fractions, and evaporation gave a yield of 13.8 g (62%). $^1$H NMR (DMSO-d$_6$); δ, 1 to 1.2 (d, 6, CH$_3$); 2.7 to 2.9 (m, 1, COCH); 3.3 to 3.5 (m, 2, C$\underline{H}_2$OH); 3.8 to 3.9 (m, 1, C$\underline{H}$OH); 3.9 to 4.3 (2m, 2, NCH$_2$); 4.8 TO 4.9 (t, 1, CH2OH, exchanges with D$_2$O); 5.1 to 5.2 (d, 1, CHO$\underline{H}$, exchanges with D$_2$O); 7.9 (s, 1, C(8)-H); 11.6 to 12.2 (2s, 2, NH, CONH, both exchange with D2O) . Anal. calcd. for C$_{12}$H$_{17}$N$_5$O$_4$ (295.297): 48.81% C, 5.80% H, 23.72% N; found: 48.36% C, 5.62% H, 23.10% N.

EXAMPLE 19

1-[9-(N2-Isobutyryl)guanine-3-O-dimethoxytrityl-2-propanol

To a suspension of 1-[9-(N2-isobutyryl)guanine]-2,3-propandiol (5.3 g, 18 mmol) in pyridine (100 ml) was added 4,4'-dimethoxytritylchloride (6.69 g, 20 mmol). The reaction mixture was allowed to stir for 4 hours at room temperature. After quenching with methanol the mixture was evaporated. The residue was purified by silica gel column chromatography. Elution with methanol:ethyl acetate:triethylamine (5/95/1, %/%/%), pooling of appropriate fractions, and evaporation gave a yield of 4.9 g (45%). $^1$H NMR (DMSO d$_6$); δ, 1.1 to 1.2 (d, 6, CH$_3$); 2.7 to 3.1 (m, 3, CH$_2$ODMT, COCH); 3.7 to 3.9 (s, 6, OCH$_3$); 4.1 to 4.3 (m, 3, NC$\underline{H}_2$C$\underline{H}$OH); 5.4 TO 5.5 (d, 1, CHO$\underline{H}$, exchanges with D$_2$O);

6.7 to 8.0 (m, 14, trityl, C(8)-H); 11.5 to 12 (2bs, 2, NH, CONH, both exchange with D2O).

EXAMPLE 20

1-[9-(N-Isobutyryl)guanine]-3-O-dimethoxytrityl-2-O-[(N,N-diisopropylamino)-2-cyanoethoxyphosphite]propane To a solution of 1-[9-(N2-isobutyryl)guanine]-3-O-dimethoxytrityl-2-propanol (13.12 g, 22 mmol) and diisopropylethylamine (10 ml) in THF (200 ml), at 0° C., was added chloro-β-cyanoethoxy-N,N-diisopropylaminophosphine (5.6 ml, 25 mmol). The reaction mixture was stirred at room temperature for 20 hours. The reaction was concentrated and the residue purified by silica gel column chromatography. Elution with ethyl acetate with 1% triethylamine, pooling of appropriate fractions and evaporation gave a yield of 8.62 g (49%). $^1$H NMR (CD$_3$CN); δ, 1.0 to 1.2 (m, 18, CH$_3$); 2.4 to 2.8 (m, 2, CH$_2$CN); 2.8 to 3.0 (m, 1, COCH); 3.1 to 3.3 (m, 2, CH$_2$ODMT); 3.4 to 3.8 (m, 9, OCH$_2$CH$_2$CN, (CH$_3$)$_2$CH, OCH$_3$); 4.2 to 4.4 (m, 3, NCH$_2$CHO); 6.7 to 7.7 (m, 14, trityl, C(8)-H); 12.3 (BS, 2, NH, CONH, both exchange with D2O). $^{31}$P NMR (CD$_3$CN); d, 150.15 and 150.48.

EXAMPLE 21

1-(1-Cytosine)-2,3-propandiol

A solution of cytosine (11.0 g, 99 mmol), R-(+)-glycidol (8.9 g, 120 mmol), and potassium carbonate (6.9 g, 50 mmol) was stirred in DMF (300 ml) at 85° C. for 22 hours. The crude reaction mixture was filtered and the filtrate evaporated. This residue was crystallized from methanol to give a yield of 10.5 g (57%). $^1$H NMR (DMSO d$_6$); δ, 3.2 to 3.5 (m, 3, CHOHCH$_2$OH); 3.6 to 3.7 (m, 1, NCH$_2$); 3.8 to 4.0 (dd, 1, NCH$_2$); 4.7 to 4.8 (t, 1, CH$_2$OH, exchanges with D$_2$O); 4.9 to 5.1 (d, 1, CHOH, exchanges with D$_2$O); 5.6 to 5.7 (d, 1, C(5)-H); 7.0 to 7.1 (bs, 2, NH$_2$, exchanges with D$_2$O); 7.4 to 7.5 (d, 1, C(6)-H).

EXAMPLE 22

1-[1-(N4-Benzoyl)cytosine]-2,3-propandiol

To an ice cold suspension of 1-(1-cytosine)-2,3-propandiol (11.11 g, 60 mmol) in pyridine (400 ml) was added chlorotrimethylsilane. This mixture was stirred for 30 minutes at ice bath temperature. Benzoyl chloride was added and the mixture was stirred at room temperature for 2 hours. The mixture was cooled to 0° C. and ice cold water (100 ml) was added. After stirring for 15 minutes ice cold ammonium hydroxide (φml) was added. The reaction mixture was stirred for 15 minutes and concentrate. Water (400 ml) was added and the mixture was heated to almost boiling. The desired product was filtered as a solid. After drying the yield was 15.31 g (88%). $^1$H NMR (DMSO d6); δ, 3.3 to 3.6 (m, 3, CHOHCH$_2$OH); 3.7 to 3.9 (bs, 1, NCH$_2$); 4.1 to 4.3 (d, 1, NCH$_2$); 4.7 to 4.9 (t, 1, CH$_2$OH, exchanges with D$_2$O); 5.1 (d, 1, CHOH, exchanges with D$_2$O); 7.2 to 7.3 (d, 1, C(5)-H); 7.5 to 7.7 (m, 3, benzoyl); 8.0 to 8.1 (d, 3, C(6)-H, benzoyl); 10.5 to 11 (bs, 1, NH, exchanges with D$_2$O).

EXAMPLE 23

1-[1-(N4-Benzoyl)cytosine]-3-O-dimethoxytrityl-2-propanol

A solution of 1-[1(N4-benzoyl)cytosine]-2,3-propandiol (7.0 g, 24 mmol) and 4,4'-dimethoxytrityl chloride (9.84, 29 mmol) in pyridine (100 ml) was stirred at room temperature for 24 hours. The reaction mixture was filtered and the filtrate is evaporated. The residue was purified by silica gel column chromatography. Elution with ethyl acetate:hexane:triethyl amine (6/4/1, v/v/%), pooling of appropriate fractions and evaporation gave a yield of (52%). $^1$H NMR (DMSO d$_6$); δ, 2.9 to 3.1 (m, 2, CH$_2$ODMT); 3.6 to 3.9 (m, 7, OCH$_3$, CHOH); 4 to 4.3 (2m, 2, NCH$_2$); 5.3 to 5.4 (d, 1, OH, exchanges with D$_2$O); 6.8 to 8.2 (3m, 20, trityl, benzoyl, C(5)-H, C(6)-H); 11.2 (s, 1, NH, exchanges with D$_2$O).

EXAMPLE 24

1-[1-(N4-Benzoyl)cytosine]-3-O-dimethoxytrityl-2-O-[(N,N-diisopropylamino)-2-cyanoethoxyphosphite]propane To a solution of 1-[1-(N4-benzoyl)cytosine]-3-O-dimethoxytrityl-2-propanol (7.48 g, 13 mmol) and diisopropylethylamine (5.5 ml) in THF (50 ml) was added chloro-β-cyanoethoxy-N-N-diisopropylaminophosphine (3.2 ml, 14 mmol). The mixture was stirred at room temperature for 2 hours. The mixture was filtered and the filtrate was purified by silica gel column chromatography. Elution with ethyl acetate:hexane:triethylamine (1/1/1, v/v/%), pooling of appropriate fractions and evaporation gave a yield of 5.7 g (57%). $^1$H NMR (CD$_3$CN); δ, 1 to 1.2 (m, 12, CH$_3$); 2.4 to 2.7 (2t, 2, CH$_2$CN); 3.1 TO 3.3 (m, 2, CH$_2$ODMT); 3.5 to 4.0 (m, 11, OCH$_2$CH$_2$CN, CH(CH$_3$)$_2$, OCH$_3$, NCH$_2$CH); 4.1 to 4.4 (m, 2, NCH$_2$); 6.6 to 8.0 (m, 20, trityl, benzoyl, C(5)-H, C(6)-H). $^{31}$P NMR (CD$_3$CN); δ, 154.5 and 155.1.

EXAMPLE 25

1-O-Dimethoxytritylglycidol

Glycidol (4.4 ml, 67 mmol) and triethylamine (19 ml, 136 mmol) was stirred in 120 ml anhydrous dichloromethane. Dimethoxytritylchloride (22.7 g, 67 mmol) was added and the mixture was stirred at room temperature for 8 hours. The mixture was filtered and the filtrate evaporated. The residue was dissolved in dichloromethane and washed with water and then brine. Coarse silica gel was added and the material was evaporated. This material was purified by silica gel column chromatography. Elution with hexane:ethyl acetate:triethylamine (19/1/1, v/v/%), pooling of appropriate fractions, and evaporation gave a yield of 16.6 g (65%). $^1$H NMR (DMSO d$_6$); δ, 2.6 to 2.9 (2t, 2, ring CH$_2$); 3.1 to 3.2 (m, 1, CH); 3.2 to 3.4 (2m, 2, CH$_2$); 3.7 (s, 1, OCH$_3$); 6.8 TO 7.4 (3m, 13, trityl).

EXAMPLE 26

1-O-Dimethoxytrityl-4-phenyl-2-butanol

Benzylmagnesiumchloride (55 ml, 2M solution, 110 mmol) was cooled to −78° C. and added to a solution of dilithiumtetrachlorocuprate (11 ml, 0.1M solution, 12 mmol) in THF (200 ml) at −78° C. To this mixture was added 1-O-dimethoxytrityl glycidol (8.28 g, 22 mmol) in THF (20 ml) at −78° C. The mixture was stirred at room temperature for 18 hours. The mixture was cooled to 0° C. and concentrated ammonium chloride (10 ml) was added slowly. The mixture was diluted with water and extracted with ethyl acetate. The ethyl acetate extracts were dried over magnesium sulfate, filtered, and concentrated. The residue was purified by silica gel column chromatography. Elution with ethyl acetate:hexane (1:9, v/v), pooling of appropriate fractions, and concentration gave a yield of 1.37 g (17%). $^1$H NMR (CDCL$_3$); δ, 1.6 to 1.8 (m, 2, C$_6$H$_5$CH$_2$); 2.3 to 2.4 (d, 1, OH, exchanges with D$_2$O); 2.5 to 2.8 (m, 2, CH$_2$CHOH); 3.0 to 3.2 (m, 2, CH$_2$ODMT); 3.8 (S, 6, OCH$_3$); 6.8 TO 7.5 (m, 18, trityl and phenyl).

EXAMPLE 27

1-O-Dimethoxytrityl-2-O-[(N,N-diisopropylamino)-2-cyanoethoxyphosphite]-4-phenylbutane 1-O-Dimethoxytrityl-4-phenyl-2-butanol (1.37 g, 2.9 mmol) and diisopropylethylamine (1.5 ml, 8.6 mmol) were stirred in THF (35 ml) and chloro-β-cyanoethoxy-N,N-diisopropylaminophosphine (0.65 ml, 2.9 mmol) was added. The mixture was stirred at room temperature for 10 hours and filtered. The material was concentrated onto silica coarse gel and dried. The material was purified by silica gel column chromatography. Elution with ethyl acetate:hexane:triethylamine (1:9:1, v/v/%), pooling of appropriate fractions, and evaporation gave a yield of 0.94 g (49%). $^1$H NMR (CDCL$_3$); δ, 1.0 to 1.3 (m, 12, CH$_3$); 1.8 to 2.1 (m, 2, C$_6$H$_5$CH$_2$); 2.3 to 2.8 (2m, 4, CH$_2$CN, C$_6$H$_5$CH$_2$CH$_2$); 3.0 to 3.3 (2m, 2, CH$_2$ODMT); 3.5 to 3.9 (m, 10, CH(CH$_3$)$_2$, POCH$_2$, OCH$_3$); 3.9 to 4.2 (m, 1, CH$_2$CH); 6.8 to 7.5 (3m, 18, phenyl and trityl). $^{31}$P NMR (CDCL$_3$); δ, 148.48 and 148.69.

EXAMPLE 28

1-Dimethoxytrityl-2-undecanol

Octylmagnesium chloride (9.4 ml, 2M solution, 18.8 mmol), was added to a solution of dilithium tetrachlorocuprate (1.9 ml, 0.1M solution, 0.11 mmol) in anhydrous THF (15 ml) at −78° C. 1-O-Dimethoxytrityl glycidol was added and the mixture was allowed to warm to room temperature and stir for 2 hours. The mixture was cooled to 0° C. and saturated ammonium chloride was added. Water was added and the mixture was extracted with ethyl acetate. The ethyl acetate extracts were combined and dried over magnesium sulfate. This material was filtered and concentrated. The residue was purified by silica gel column chromatography. Elution with ethyl acetate/hexane/triethylamine (5/95/1, v/v/%), pooling of appropriate fractions, and evaporation gave a yield of 1.1 g (60%). $^1$H NMR (CDCL$_3$); δ, 0.8 to 0.9 (t, 3, CH$_3$); 1.2 to 1.4 (m, 16, (CH$_2$)$_7$CH$_2$); 2.3 TO 2.4 (d, 1, OH, exchanges with D$_2$O); 3.0 to 3.2 (m, 2, CH$_2$ODMT); 3.7 to 3.9 (s, 7, OCH$_3$, CHOH); 6.8 to 7.5 (m, 14, DMT).

EXAMPLE 29

1-Dimethoxytrityl-2-O-[(N,N-diisopropylamino)-2-cyanoethoxyphosphite]undecane A mixture of HPLC purified 1-dimethoxytrityl-2-undecanol (1.06 g, 2.2 mmol), chloro-β-cyanoethoxy-N,N-diisopropylaminophosphine (0.5 ml, 2.2 mmol), and triethylamine (1.0 ml, 5.7 mmol) in THF (50 ml) was stirred for 20 hours at room temperature. The mixture was concentrated and purified by silica gel column chromatography. Elution with ethyl acetate/hexane/triethylamine (1/9/1, v/v/%), pooling of appropriate fractions, and evaporation gives the title compound.

EXAMPLE 30

Fluorenyl succinic acid half ester

To a solution of 9-fluorenylmethanol (3.92 g, 20 mmol), succinic anhydride (2.20 g, 22 mmol), and 4-dimethylaminopyridine (0.25 g, 2 mmol) in dichloromethane (25 ml) was added triethylamine (3 ml). The mixture was stirred at room temperature for four hours. The reaction was diluted with dichloromethane (50 ml) and extracted with saturated sodium bicarbonate (3×50 ml). The combined extracts were back extracted with ethyl acetate. The resulting sodium bicarbonate solution was acidified with 3N HCl and refrigerated. A precipitate fell out of the solution which yielded 3.05 g (56%) of the title compound after drying.

EXAMPLE 31

Fluorenyl-[N-(amino-2,3-propandiol)]succinimide half ester

To a suspension of fluorenyl succinic acid half ester (3.05 g, 11.24 mmol) in DMF (50 ml) was added 1-hydroxybenzotriazole (2.28 g, 16.86 mmol) and 1-(3-dimethylaminopropyl)-3-ethylcarbodiimide-HCl (3.23 g, 16.84 mmol) sequentially. The mixture was stirred at room temperature for two hours and transferred via cannula to a flask containing 1-amino-2,3-propanediol (1.02 g, 11.24 mmol). The reaction was stirred for three hours at room temperature. The mixture was concentrated and partitioned between ethyl acetate (100 ml) and water (50 ml). The layers were separated and the aqueous layer was extracted with ethyl acetate (3×50 ml). The ethyl acetate extracts were combined, dried over sodium sulfate, filtered, and concentrated. $^1$H NMR: (CDCl$_3$, 200 MHz) δ 7.8–7.26 (8H, m, ArH), 4.43 (2H, d, J=6.5 Hz, CHCH$_2$OCO), 4.23 (1H, t, J=6.5 Hz, CHCH$_2$OCO), 2.70 (4H, S, OCOCH$_2$CH$_2$COO).

EXAMPLE 32

Fluorenyl-[N-(1-amino-3-O-dimethoxytrityl-2-propanol)succinimide] half ester A solution of fluorenyl-[N-(2,3-propandiol)]succinimide half ester (0.74 g, 2.0 mmol) in pyridine (20 ml) was treated with 4,4'-dimethoxytritylchloride (0.68 g, 2.0 mmol). The mixture was stirred overnight at room temperature. Thin layer chromatography (TLC) analysis of the product shows complete conversion to a higher migrating spot, which gives the characteristic red color when sprayed with 10% sulfuric acid in methanol and heated.

EXAMPLE 33

Fluorenyl-N-{3-O-dimethoxytrityl-2-O-[(N,N-diisopropylamino)-2-cyanoethoxyphosphite]propane} succinimide ester The title phosphoramidite is prepared from fluorenyl-[N-(3-O-dimethoxytrityl-2-propanol)] succinimide half ester utilizing the procedure of example 27.

EXAMPLE 34

1-[(N-Benzoyl)amino]-2,3-propandiol

R-(+)-glycidol (10 ml, 0.15 mol) and isopropyl alcohol saturated with ammonia (70 ml) were sealed in a bomb and stirred at room temperature for 5 days. The bomb was cooled and opened. The solution was evaporated and the residue dissolved in pyridine (100 ml). This solution was treated with benzoyl chloride (47 ml, 0.4 mol) for 30 minutes and filtered. The filtrate was evaporated and dissolved in methanol (400 ml) then treated with ammonium hydroxide (100 ml). The mixture was stirred for 4 hours and evaporated. The residue was purified by silica gel column chromatography. Elution with ethyl acetate:methanol (19/1, v/v), pooling of appropriate fractions and evaporation gave a yield of 9.9 g (34%) $^1$H NMR (DMSO d$_6$); δ, 3.1 to 3.5 (m, 4, CH$_2$CHOHCH$_2$OH); 3.6 to 3.7 (m, 1, CHOH); 4.6 to 4.7 (t, 1, CH$_2$OH, exchanges with D$_2$O); 4.8 to 4.9 (d, 1, CHOH, exchanges with D$_2$O); 7.4 TO 7.6 and 7.8 to 7.9 (m, 5, benzoyl); 8.4 to 8.5 (t, 1, NH).

EXAMPLE 35

1-[(N-Benzoyl)amino]-3-O-dimethoxytrityl-2-O-[(N,N-diisopropylamino)-2-cyanoethoxyphosphite]propane 1-[(N-Benzoyl)amino]-2,3-propandiol is treated as per the procedure of Example 5 with dimethoxytrityl chloride in pryidine to give 1-[(N-benzoyl)amino]-3-O-dimethoxytrityl-2-propanol. The resulting 1-[(N-benzoyl)amino]-3-O-dimethoxytrityl-2-propanol is further phosphitylated with chloro-β-cyanoethoxy-N,N-diisopropylaminophosphine as per Example 6 to give the title compound.

EXAMPLE 36

1-(1-Pyrrole)-3-O-dimethoxytrityl-2-O-[(N,N-diisopropylamino)-2-cyanoethoxyphosphite]propane Pyrrole is treated as per the procedure of Example 4 with glycidol in the presence of potassium carbonate to give 1-(1H-pyrrole)-2,3-propandiol. The resulting 1-(1-pyrrole)-2,3-propandiol is further treated as per the procedure of Example 5 with dimethoxytrityl chloride in pryidine to give 1-(1-pyrrole)-3-O-dimethoxytrityl-2-propanol. The resulting 1-(1-pyrrole)-3-O-dimethoxytrityl-2-propanol is further phosphitylated with chloro-β-cyanoethoxy-N,N-diisopropylaminophosphine as per Example 6 to give the title compound.

EXAMPLE 37

1-(10-Phenoxazine)-3-O-dimethoxytrityl-2-O-(N,N-diisopropylamino)-2-cyanoethoxyphosphite]propane Phenoxazine is treated as per the procedure of Example 4 with glycidol in the presence of potassium carbonate to give 1-(1-phenoxazine)-2,3-propandiol. The resulting 1-(1-phenoxazine)-2,3-propandiol is treated as per the procedure of Example 5 with dimethoxytrityl chloride in pryidine to give 1-(1-phenoxazine)-3-O-dimethoxytrityl-2-propanol. The resulting 1-(1-phenoxazine)-3-O-dimethoxytrityl-2-propanol is phosphitylated with chloro-β-cyanoethoxy-N,N-diisopropylaminophosphine as per Example 6 to give the title compound.

EXAMPLE 38

1-(1-Pyrazole)-3-O-dimethoxytrityl-2-O-[(N,N-diisopropylamino)-2-cyanoethoxyphosphite]propane Pyrazole is treated as per the procedure of Example 4 with glycidol in the presence of potassium carbonate to give 1-(1-pyrazole)-2,3-propandiol. The resulting 1-(1-pyrazole)-2,3-propandiol is treated as per the procedure of Example 5 with dimethoxytrityl chloride in pryidine to give 1-(1-pyrazole)-3-O-dimethoxytrityl-2-propanol. The resulting 1-(1-pyrazole)-3-O-dimethoxytrityl-2-propanol is phosphitylated with chloro-β-cyanoethoxy-N,N-diisopropylaminophosphine as per Example 6 to give the title compound.

EXAMPLE 39

1-(1-Indole)-3-O-dimethoxytrityl-2-O-[(N,N-diisopropylamino)-2-cyanoethoxyphosphite]propane Indole is treated as per the procedure of Example 4 with glycidol in the presence of potassium carbonate to give 1-(1-indole)-2,3-propandiol. The resulting 1-(1-indole)-2,3-propandiol is treated as per the procedure of Example 5 with dimethoxytrityl chloride in pryidine to give 1-(1-indole)-3-O-dimethoxytrityl-2-propanol. The resulting 1-(1-indole)-3-O-dimethoxytrityl-2-propanol is phosphitylated with chloro-β-cyanoethoxy-N,N-diisopropylaminophosphine as per Example 6 to give the title compound.

EXAMPLE 40

1-(1-Indazole)-3-O-dimethoxytrityl-2-O-[(N,N-diisopropylamino)-2-cyanoethoxyphosphite]propane 1H-Indazole is treated as per the procedure of example 4 with glycidol in the presence of potassium carbonate to give 1-(1H-indazole)-2,3-propandiol. The resulting 1-(1H-indazole)-2,3-propandiol is treated as per the procedure of Example 5 with dimethoxytrityl chloride in pryidine to give 1-(1-indazole)-3-O-dimethoxytrityl-2-propanol. The resulting 1-(1-indazole)-3-O-dimethoxytrityl-2-propanol is phosphitylated with chloro-β-cyanoethoxy-N,N-diisopropylaminophosphine as per Example 6 to give the title compound.

EXAMPLE 41

1-(9-Purine)-3-O-dimethoxytrityl-2-O-[(N,N-diisopropylamino)-2-cyanoethoxyphosphite]propane Purine is treated as per the procedure of example 4 with glycidol in the presence of potassium carbonate to give 1-(9-purine)-2,3-propandiol. The resulting 1-(9-purine)-2,3-propandiol is treated as per the procedure of example 5 with dimethoxytrityl chloride in pryidine to give 1-(9-purine)-3-O-dimethoxytrityl-2-propanol. The resulting 1-(9-purine)-3-O-dimethoxytrityl-2-propanol is phosphitylated with chloro-β-cyanoethoxy-N,N-diisopropylaminophosphine as per Example 6 to give the title compound.

EXAMPLE 42

1-(10-Phenothiazine)-3-O-dimethoxytrityl-2-O-[(N,N-diisopropylamino)-2-cyanoethoxyphosphite]propane Phenothiazine is treated as per the procedure of Example 4 with glycidol in the presence of potassium carbonate to give 1-(10-phenothiazine)-2,3-propandiol. The resulting 1-(10-phenothiazine)-2,3-propandiol is treated as per the procedure of example 5 with dimethoxytrityl chloride in pryidine to give 1-(10-phenothiazine)-3-O-dimethoxytrityl-2-propanol. The resulting 1-(10-phenothiazine)-3-O-dimethoxytrityl-2-propanol is phosphitylated with chloro-β-cyanoethoxy-N,N-diisopropylaminophosphine as per Example 6 to give the title compound.

EXAMPLE 43

1-(9-β-Carboline)-3-O-dimethoxytrityl-2-O-[(N,N-diisopropylamino)-2-cyanoethoxyphosphite]propane β-Carboline is treated as per the procedure of Example 4 with glycidol in the presence of potassium carbonate to give 1-(9-β-carboline)-2,3-propandiol. The resulting 1-(9-β- carboline)-2,3-propandiol is treated as per the procedure of Example 5 with dimethoxytrityl chloride in pryidine to give 1-(9-β-carboline)-3-O-dimethoxytrityl-2-propanol. The resulting 1-(9-β-carboline)-3-O-dimethoxytrityl-2-propanol is phosphitylated with chloro-β-cyanoethoxy-N,N-diisopropylaminophosphine as per Example 6 to give the title compound.

EXAMPLE 44

1-(10-Phenothiazine)-3-O-dimethoxytrityl-2-O-[(N, N-diisopropylamino)-2-cyanoethoxyphosphite] propane Phenothiazine is treated as per the procedure of Example 4 with glycidol in the presence of potassium carbonate to give 1-(10-phenothiazine)-2,3-propandiol. The resulting 1-(10-phenothiazine)-2,3-propandiol is treated as per the procedure of Example 5 with dimethoxytrityl chloride in pryidine to give 1-(10-phenothiazine)-3-O-dimethoxytrityl-2-propanol. The resulting 1-(10-phenothiazine)-3-O-dimethoxytrityl-2-propanol is phosphitylated with chloro-β-cyanoethoxy-N,N-diisopropylaminophosphine as per Example 6 to give the title compound.

EXAMPLE 45

1-[1-(5-Propynyl)uracil]-3-O-dimethoxytrityl-2-O-[ (N,N-diisopropylamino)-2-cyanoethoxyphosphite] propane 5-Propynyl)uracil is treated as in the procedure of Example 9 with glycidol in the presence of potassium carbonate to give 1-[1-(5-propynyl)uracil]-2,3-propandiol. The resulting 1-[1-(5-propynyl)uracil]-2,3-propandiol is treated with dimethoxytrityl chloride in pyridine as in Example 10 to give 1-[1-(5-propynyl)uracil]-3-O-dimethoxytrityl-2-propanol. The resulting 1-[1-(5-propynyl) uracil]-3-O-dimethoxytrityl-2-propanol is phosphitylated with chloro-β-cyanoethoxy-N,N-diisopropylaminophosphine as per Example 11 to give the title compound.

EXAMPLE 46

1-[1-(6-Aza)thymine]-3-O-dimethoxytrityl-2-O-[(N, N-diisopropylamino)-2-cyanoethoxyphosphite] propane 6-Azathymine is treated as in the procedure of Example 1 with glycidol in the presence of potassium carbonate to give 1-[1-(6-aza)thymine]-2,3-propandiol. The resulting 1-[1-(6-aza)thymine]-2,3-propandiol is treated with dimethoxytrityl chloride in pyridine as in Example 2 to give 1-[1-(6-aza)-thymine]-3-O-dimethoxytrityl-2-propanol. The resulting 1-[1-(6-aza)thymine]-3-O-dimethoxytrityl-2-propanol is phosphitylated with chloro-β-cyanoethoxy-N,N-diisopropylaminophosphine as per Example 3 to give the title compound.

EXAMPLE 47

1-(9-Hypoxanthine)-3-O-dimethoxytrityl-2-O-[(N, N-diisopropylamino)-2-cyanoethoxyphosphite] propane Hypoxanthine is treated as in the procedure of Example 1 with glycidol in the presence of potassium carbonate to give 1-(hypoxanthine-9-yl)-2,3-propandiol. The resulting 1-(9-hypoxanthine)-2,3-propandiol is treated with dimethoxytri- tyl chloride in pyridine as in Example 2 to give 1-(9-hypoxanthine)-3-O-dimethoxytrityl-2-propanol. The resulting 1-(9-hypoxanthine)-3-O-dimethoxytrityl-2-propanol is phosphitylated with chloro-β-cyanoethoxy-N,N-diisopropylaminophosphine as per Example 3 to give the title compound.

EXAMPLE 48

1-[9-(2,6-Diamino)purine]-3-O-dimethoxytrityl-2-O-[(N,N-diisopropylamino)-2-cyanoethoxyphosphite] propane 2,6-Diaminopurine is treated as in the procedure of Example 16 with glycidol in the presence of potassium carbonate to give 1-[9-(2,6-diamino)purine]-2,3-propandiol. The resulting 1-[9-(2,6-diamino)purine]-2,3-propandiol is protected as in Example 18 by treatment with chlorotrimethylsilane and isobutyryl chloride to give 1-[9-(N2,N6-diisobutyryl-2,6-diamino)purine]-2,3-propandiol. The resulting 1-[9-(N2,N6-diisobutyryl-2,6-diamino)purine]-2,3-propandiol is treated with dimethoxytrityl chloride in pyridine as in Example 19 to give 1-[9-(N2,N6-diisobutyryl-2,6-diamino)-purine[ ]-3-O-dimethoxytrityl-2-propanol. The resulting 1-[9-(N2,N6-diisobutyryl-2,6-diamino)purine]-3-O-dimethoxytrityl-2-propanol is then phosphitylated with chloro-β-cyanoethoxy-N,N-diisopropylaminophosphine as per Example 24 to give the title compound.

EXAMPLE 49

1-[9-(7-Methylguanine)]-3-O-dimethoxytrityl-2-O-[ (N,N-diisopropylamino)-2-cyanoethoxyphosphite] propane 7-Methylguanine is treated as in the procedure of Example 16 with glycidol in the presence of potassium carbonate to give 1-[9-(7-methylguanine)]-2,3-propandiol. The resulting 1-[9-(7-methylguanine)]-2,3-propandiol is protected as in Example 18 by treatment with chlorotrimethylsilane and isobutyryl chloride to give 1-[9-(N2-isobutyryl)-(7-methylguanine)]-2,3-propandiol. The resulting 1-[9-(N2-isobutyryl)-(7-methylguanine)]-2,3-propandiol is treated with dimethoxytrityl chloride in pyridine as in Example 19 to give 1-[9-(N2-isobutyryl)-(7-methylguanine)]-3-O-dimethoxytrityl-2-propanol. The resulting 1-[9-(N2-isobutyryl)-(7-methylguanine)]-3-O-dimethoxytrityl-2-propanol is then phosphitylated with chloro-β-cyanoethoxy-N,N-diisopropylaminophosphine as per Example 20 to give the title compound.

EXAMPLE 50

N-(α-Fmoc)-N'-(amino-2,3-propandiol)glycinamide

A solution of N-α-Fmoc-glycine-pentafluorophenyl ester (4.0 g, 8.6 mmole) in dry dimethylformamide was treated with 1-amino-2,3-propandiol (0.78 g, 8.6 mmole) under an atmosphere of argon. The mixture was stirred at room temperature for 6 hr and the solvent evaporated under reduced pressure. The syrup which resulted was kept under vacuum overnight and then dissolved in 40 ml hot ethyl acetate. The hot solution was filtered, the filtrate cooled to −20° C. and kept in ice overnight. The material which had crystallized was filtered, washed with cold ethyl acetate and the filtrate evaporated to a minimum volume. A second incubation at this temperature yielded a second crop of crystals. Yield of white crystals is 2.2 g (69%). $^1$H nmr (dimethylsulfoxide-d$_6$): 8.0-7.2 (m, 8, aromatic); 5.0-4.5 (m, 4, N—H and OH, exchangeable with $D_2O$); 4.3 (m, 3, Fmoc); 3.7 (m, 2, glycine); 3.5-3.0 (m, 5, 20 propane).

EXAMPLE 51

N-(α-Fmoc)-N'-{3-O-dimethoxytrityl-2-O-[(N,N-diisopropylamino)-2-cyanoethoxyphosphite]aminopropane}glycinamide A solution of N-(α-Fmoc)-N'-(amino-2,3-propandiol)-glycinamide (2.0 mmol) in pyridine (20 ml) is treated with 4,4'-dimethoxytritylchloride (0.68 g, 2.0 mmol) as per the procedure of Example 32. The mixture is stirred overnight at room temperature to give N-(α-Fmoc)-N'-(1-amino-3-O-dimethoxytrityl-2-propanol)glycinamide that is isolated by silica gel chromatography. The resulting N-(α-Fmoc)-N'-(1-amino-3-O-dimethoxytrityl-2-propanol)glycinamide is treated as per the procedure of Example 27 to give the title compound.

EXAMPLE 52

1-Dimethoxytrityl-2-O-[(N,N-diisopropylamino)-2-cyanoethoxyphosphite]heptadecane Dodecylbromide is reacted with metallic magnesium in ethyl ether to yield dodecylomagnesium bromide. The dodecylmagnesium bromide is reacted with 1-O-dimethoxytritylglycidol (see Example 25) in THF in the presence of dilithiumtetrachlorocuprate to give 1-dimethoxytrityl-2-heptadecanol. The resulting 1-dimethoxytrityl-2-heptadecanol is reacted with chloro-β-cyanoethoxy-N,N-diisopropylaminophosphine in the presence of diisopropylethylamine in THF to give the title compound.

EXAMPLE 53

1-Amino-3-O-dimethoxytrityl-2-propanol

1-O-Dimethoxytritylglycidol (from Example 25, 10 ml, 0.15 mol) and isopropyl alcohol saturated with ammonia (70 ml) are sealed in a bomb and stirred at room temperature for 5 days. The bomb is cooled, opened and the solution evaporated to give the crude product.

EXAMPLE 54

1-[(N-Palmitoyl)amino]-3-O-dimethoxytritylmethyl-2-O-[(N,N-diisopropylamino)-2-cyanoethoxyphosphite]propane 1-Amino-3-O-dimethoxytrityl-2-propanol (from Example 53) is dissolved in 5 ml dry pyridine and chlorotrimethylsilane (0.227 ml, 194 mg, 1.79 mmol), is added with stirring for 1 hour. Palmitic acid (359 mg, 1.40 mmol), hydroxybenzotriazole (209 mg, 1.55 mmol) and dimethylaminopropylethylcarbodiimide (EDC) (281 mg, 1.80 mmol) are dissolved in 5 ml DMF (if necessary, 5 ml $CH_2Cl_2$ co-solvent is added) and stirred for 1 hour. This solution is then added to the pyridine solution of the crude 1-amino-3-O-dimethoxytrityl-2-propanol, and the solution stirred until complete disappearance of the starting material. The reaction is stopped by addition of 5 ml saturated $NaHCO_3$ and after 15 min. the solution is diluted with water (100 ml), extracted with ethyl acetate (2×75 ml), washed with $NaHCO_3$, brine, dried and evaporated. The residue is purified by silica gel chromatography to give 1-[($N^1$-palmitoyl)amino]-3-O-dimethoxytritylmethyl-2-propandiol. The resulting 1-[($N^1$-palmitoyl)amino]-3-O-dimethoxytritylmethyl-2-propandiol is phosphitylated with chloro-β-cyanoethoxy-N,N-diisopropylaminophosphine as per Example 20 to give the title compound.

EXAMPLE 55

1-[(N-Isobutyroyl)amino]-3-O-dimethoxytritylmethyl-2-O-[(N,N-diisopropyl-amino)-2-cyanoethoxyphosphite]propane The title compound is prepared as per the procedure of Example 54 by the use of isobutyric acid as the carboxylic acid component.

EXAMPLE 56

1-[(N-Phenylacetyl)amino]-3-O-dimethoxytritylmethyl-2-O-[(N,N-diisopropylamino)-2-cyanoethoxyphosphite]propane The title compound is prepared as per the procedure of Example 54 by the use of phenylacetic acid as the carboxylic acid component.

EXAMPLE 57

Glutaric acid monofluorenylmethyl ester.

Fluorenylmethanol (0.90 g, 4.5 mmol) and dimethylaminopyridine (50 mg) are dissolved in 10 ml dry pyridine. Glutaric anhydride (5.0 mmol) is added and the solution stirred overnight. The solvent is removed under reduced pressure, sodium bicarbonate added (50 ml), the solution extracted with ethyl acetate (50 ml), and the organic layer discarded. The aqueous layer is acidified to pH 2, extracted with ethyl acetate (2×100 ml), washed with brine, and the solvent removed under reduced pressure. The residue is purified by flash chromatography to give the product.

EXAMPLE 58

1-[(N-(Fluorenylmethylglutaroyl)amino]-3-O-dimethoxytritylmethyl-2-O-[(N,N-diisopropylamino)-2-cyanoethoxyphosphite]-propane The title compound is prepared as per the procedure of Example 54 using glutaric acid monofluorenylmethyl ester (Example 57) as the carboxylic acid component.

EXAMPLE 59

2-(1-Thymine)acetic acid

Methyl bromoacetate (25.5 g, 15.2 ml, 160 mmol) was added to a suspension of $K_2CO_3$ (44.2 g, 320 mmol) and thymidine (20.2 g, 160 mmol) in 500 ml dry DMF with stirring overnight. The suspension was filtered and the solvent removed under reduced pressure. The residue was suspended in 120 ml $H_2O$ and 30 ml 4N HCl, stirred for 30 min and filtered again. The solid was suspended in 250 ml $H_2O$, to which was added 100 ml 2.5M NaOH. The solution was heated to boiling, cooled and acidified to pH 1 with concentrated HCl. The precipitate was dried in vacuo to give 13.6 g (73.6 mmol, 46%) pure product. $^1$H NMR: (DMSO-d6, 200 MHz) δ 7.48 (s, 1H, H6), 4.37 (s, 2H, $CH_2$), 1.76 (s, 3H, $CH_3$)

EXAMPLE 60

1-{N-[2-(1-Thymidine)acetyl]amino}-3-O-dimethoxytritylmethyl-2-O-[(N,N-diisopropylamino)-2-cyanoethoxyphosphite]propane The title compound is prepared as per the procedure of Example 54 using thymidine-2-acetic acid as the carboxylic acid component.

EXAMPLE 61

N-Fmoc-3-Aminopropionic Acid.

Sodium bicarbonate (2.52 g, 30 mmol) and 3-aminopropionic acid (1.00 g, 11.2 mmol) were dissolved in 50 ml water and 50 ml dioxane was added. A solution of fluorenylmethyl chloroformate (3.10 g, 12.0 mmol) in 50 ml dioxane was added dropwise with stirring. After 6 hours the solution was diluted with water (100 ml) and saturated bicarbonate solution (50 ml), extracted once with diethyl ether, and the aqueous layer acidified to pH 2 with concentrated HCl. The cloudy solution was extracted with ethyl acetate (2×100 ml), washed with brine and dried with $MgSO_4$. After evaporation a mixture of the title product and the peptide dimer was obtained. The pure product was obtained by flash chromatography. $^1H$ NMR: ($CDCl_3$, 200 MHz) δ 7.95-7.26 (8H, m, ArH), 7.40-7.15 (3H, m, $CHCH_2O$), 3.20 (2H, t, J=8 Hz, $CH_2N$), 2.40 (2H, t, J=8 Hz, $HOOCCH_2$)

EXAMPLE 62

1-[N-(N-Fmoc-3-aminopropionoyl)amino]-3-O-dimethoxytritylmethyl-2-O-[(N,N-diisopropylamino)-2-cyanoethoxyphosphite]-propane The title compound is prepared as per the procedure of Example 54 using N-Fmoc-3-aminopropionic acid as the carboxylic acid component.

EXAMPLE 63

2-(N-Imidazolyl)acetic acid

Imidazole (3.7 g, 54 mmol) was added to a suspension of sodium hydride (2.6 g of a 60% dispersion in oil, 60 mmol) in 50 ml dry THF. Bromoacetic acid (3.4 g, 24 mmol) was then added and the mixture stirred overnight. Water (1 ml) was then added and the solvent removed under reduced pressure. The residue was taken up in water (50 ml, pH>10), extracted with ether and the organic layer discarded. The aqueous layer was acidified to pH 1 with concentrated HCl and extracted again with ether. The aqueous layer was evaporated to dryness. The oily residue was dissolved in absolute ethanol (EtOH) to precipitate NaCl, and recrystallized from acetone/methanol to give 1.22 g (7.5 mmol, 30%) pure product as the hydrochloride. $^1H$ NMR: ( DMSO-d6, 200 MHz) δ 9.20 (s, H2), 7.76 (d, J=1.5 Hz), 7.69 (d, J=1.5 Hz), 5.20 (s, $CH_2$).0

EXAMPLE 64

1-{N-[2-(N-Imidazolyl)acetyl]amino}-3-O-dimethoxytritylmethyl-2-O-[(N,N-diisopropylamino)-2-cyanoethoxyphosphite]propane The title compound is prepared as per the procedure of Example 54 using N-imidazolyl-2-acetic acid as the carboxylic acid component.

EXAMPLE 65

2-(9-Adenine)acetic acid ethyl ester

Sodium hydride (8.20 g 60% in oil, 205 mmol) was added to a suspension of adenine (25.0 g, 185 mmol) in 500 ml DMF. After 2 hours vigorous mechanical stirring $H_2$ evolution stopped and a thick slurry was obtained. Ethyl bromoacetate (55.6 g, 36.9 ml, 333 mmol) was added dropwise over 3 hours, and stirring continued for a further hour. Water (10 ml) and $H_2SO_4$ were added to pH 4. The solvent was evaporated and the residue suspended in 500 ml $H_2O$, filtered and washed with water. The residue was recrystallized from 400 ml ethanol to give 23.8 g (108 mmol, 58%) pure product.

EXAMPLE 66

2-[9-(N2-Benzoyl)adenine)acetic acid

To a suspension of 2-(9-adenine)acetic acid ethyl ester (6.06 g, 27.4 mmol) in 250 ml dry pyridine was added benzoyl chloride (9.60 ml, 11.6 g, 82 mmol), and the solution stirred for 4 hours at room temperature. Methanol (25 ml) was added and the solvents evaporated. The residue was dissolved in ethyl acetate (2×250 ml), washed with 0.1N HCl, $H_2O$, $NaHCO_3$ saturated, brine, and dried with $Na_2SO_4$. The organic extracts were evaporated and the solid residue was redissolved in 250 ml THF at 0° C., to which was added 100 ml 1M NaOH. The solution was stirred at 0° C. for 1 hour and acidified to pH 1 with concentrated HCl, and the aqueous portion extracted once with ether. The product, which began to crystallize almost immediately, was collected by filtration to yield 4.96 g (61%). $^1H$ NMR: (DMSO-d6, 200 MHz) δ 8.86, 8.84 (d, H2, H8), 8.1 (d, 2H, J=7.0 Hz, ArH), 7.69-7.58 (m, 3H, Ar—H), 5.22 (s, 2H, $CH_2$)

EXAMPLE 67

1-{{N-{2-[9-(N2-Benzoyl)adenine]acetyl}amino}}-3-O-dimethoxytritylmethyl-2-O-[(N,N-diisopropylamino)-2-cyanoethoxyphosphite]propane The title compound is prepared as per the procedure of Example 54 using 2-[9-(N2-benzoyl)adenine]acetic acid as the carboxylic acid component.

EXAMPLE 68

2-[1-(N4-Benzoyl)cytosine]acetic acid

Cytosine hemihydrate (12.0 g, 100 mmol) was dried by coevaporation with pyridine, redissolved in dry pyridine (250 ml), and benzoyl chloride added dropwise (70.3 g, 500 mmol) with cooling. The solution was stirred overnight, water added and the solvent removed in vacuo. The residue was dissolved in 700 ml $H_2O$ containing 55 g NaOH. Once complete dissolution had occurred stirring was continued for one hour. The solution was then acidified to pH 4, and the white precipitate collected, boiled in 1 L ethanol and filtered again to give 16.1 g benzoylcytosine. Fifteen grams of this was suspended in 500 ml DMF with 9.7 g (70 mmol) $K_2CO_3$ and methyl bromoacetate (10.7 g, 70 mmol). The suspension was stirred for 3 days, filtered and the solvent removed. Water was added (100 ml) and 10 ml 4N HCl. The suspension was stirred 15 min and filtered. The solid was resuspended in 200 ml $H_2O$ containing 4.8 g NaOH. The suspension was stirred 45 min until all the solid had dissolved. The solution was then acidified to pH 2, the solid collected by filtration and dried to give 10.6 g product (43%). The product was identified by NMR.

EXAMPLE 69

1-{{N-{2-[1-(N4-Benzoyl)cytosine]acetyl}amino}}-3-O-dimethoxytritylmethyl-1-amino-2-O-[(N,N-diisopropylamino)-2-cyanoethoxyphosphite]propane The title compound is prepared via the procedure of Example 54 using 2-[1-(N4-benzoyl)cytosine]acetic acid as the carboxylic acid component.

EXAMPLE 70

2-[9-(N2-Isobutyroyl)guanine]acetic acid.

To a suspension of 2-amino-6-chloropurine (10 mmol) and $K_2CO_3$ (15 mmol) in DMF (25 ml) is added ethyl bromoacetate (10 mmol). The mixture is stirred vigorously for 24 hrs, filtered and the solvent evaporated. The residue is resuspended in 25 ml pyridine and isobutyroyl chloride added (20 mmol). After stirring for 18 hrs, water is added and the solvent removed. The residue is suspended in 1N HCl and heated to reflux for 1 hr. The suspension is then cooled to 0° C., NaOH added to pH 12, and the suspension stirred for 1 hr. The solution is acidified to pH 3, and the product is collected by filtration.

EXAMPLE 71

1-{{N-{2-[9-(N2-Isobutyroyl)guanine] acetyl}amino}}-3-O-dimethoxytritylmethyl-1-amino-2-O-[(N,N-diisopropylamino)-2-cyanoethoxyphosphite]propane The title compound is prepared via the procedure of Example 54 using 2-[9-(N2-isobutyroyl)guanine]acetic acid as the carboxylic acid component.

EXAMPLE 72

Benzyl 3,6,9,12-tetraoxatridecanoate

Triethyleneglycol monomethyl ether (10 mmol) and benzyl bromoacetate (11 mmol) are added to a suspension of anhydrous $K_2CO_3$ (15 mmol) in 50 ml anhydrous DMF. The suspension is stirred at room temperature overnight. Water is added and the emulsion is extracted with ethyl acetate (3×200 ml), washed with water, brine, and dried with $MgSO_4$. The solvent is evaporated and the residual oil purified by flash chromatography to give the title compound.

EXAMPLE 73

3,6,9,12-Tetraoxatridecanoic acid

Benzyl 3,6,9,12-tetraoxatridecanoate (5 mmol) is dissolved in methanol (50 ml) and 10% palladium on carbon is added (100 mg catalyst/mmol). The suspension is shaken under 30 psi $H_2$ until the starting material is consumed. The suspension is filtered through a short pad of Celite, washed thoroughly with methanol, and the solvent evaporated. The product is used directly without purification.

EXAMPLE 74

1-[N-(3,6,9,12-Tetraoxatridecanoyl)amino]-3-O-dimethoxytritylmethyl-2-O-[(N,N-diisopropylamino) -2-cyanoethoxyphosphite]propane The title compound is prepared via the procedure of Example 54 using 3,6,9,12-tetraoxatridecanoic acid as the carboxylic acid component.

EXAMPLE 75

Benzyl bis-[(2-pyridyl)-2-ethyl]aminoacetate

To a suspension of $K_2CO_3$ (15 mmol) in 25 ml DMF was added 2,2'-bis(2-pyridylethyl)-amine (10 mmol) followed by benzyl bromoacetate (12 mmol). The suspension was stirred for 4 hours at room temperature. Water was then added, and the suspension extracted with ethyl acetate (2×100 ml), washed with 5% $Na_2CO_3$, water, brine, dried with $MgSO_4$ and the solvents removed. The product was obtained as an oil in quantitative yield. Product was identified by NMR.

EXAMPLE 76

Bis(2-(2-pyridyl)ethyl)aminoacetic acid

Benzyl bis-[(2-pyridyl)-2-ethyl]aminoacetate (5 mmol) is dissolved in methanol (50 ml) and 10% Palladium on carbon is added (100 mg catalyst/mmol). The suspension is shaken under 30 psi $H_2$ until the starting material is consumed. The suspension is filtered through a short pad of Celite, washed thoroughly with methanol, and the solvent evaporated. The product is used directly without purification.

EXAMPLE 77

1-{{N-{Bis [2-(2-pyridyl)ethyl] aminoacetyl}amino}}-3-O-dimethoxytritylmethyl-2-O-[(N,N-diisopropylamino)-2-cyanoethoxyphosphite]propane This compound is prepared via the procedure of Example 54 using bis(2-(2-pyridyl)ethyl)-aminoacetic acid as the carboxylic acid component.

EXAMPLE 78

1-[N-(Toluenesulfonyl)amino]-3-O-dimethoxytritylmethyl-2-O-[(N,N-diisopropylamino) -2-cyanoethoxyphosphite]propane Chlorotrimethylsilane (6.0 mmol) is added dropwise to a solution of 1-amino-3-O-dimethoxytrityl-2-propanol (5.0 mmol) in 25 ml dry pyridine. After stirring one hour, toluenesulfonyl chloride (6.0 mmol) is added in portions, and stirring continued for two hours. The reaction is quenched with saturated aqueous $NaHCO_3$, and the mixture stirred until the silyl ethers were hydrolyzed. The solvent is removed in vacuo, and the residue partitioned between water and ethyl acetate. The organic layer is washed with $NaHCO_3$, water, brine and dried with $Na_2SO_4$. The solvent is removed and the resulting oil purified by flash chromatography, using a gradient of methanol in $CHCl_3$. The resulting 1-[N-(toluenesulfonyl)amino]-3-O-dimethoxytritylmethyl-2-propanol is phosphitylated with chloro-β-cyanoethoxy-N,N-diisopropylaminophosphine as per Example 20 to give the title compound.

EXAMPLE 79

1-[N-(Trifluoromethanesulfonyl)amino]-3-O-dimethoxytritylmethyl-2-O-[(N,N-diisopropylamino) -2-cyanoethoxyphosphite]propane Chlorotrimethylsilane (6.0 mmol) is added dropwise to a solution of 1-amino-3-O-dimethoxytrityl-2-propanol (5.0 mmol) and triethylamine (15 mmol) in 50 ml dry $CH_2Cl_2$. After 1 hour the solution is cooled to −78° C., and trifluoromethanesulfonic anhydride (5.5 mmol) is added dropwise. The cooling bath is removed and the mixture allowed to warm to room temperature. The crude product is dissolved in pyridine and $NaHCO_3$ solution is added to hydrolyze the TMS ether. The solvent is evaporated, the residue partitioned between ethyl acetate and water, washed with $NaHCO_3$, brine and dried with $MgSO_4$. The residue is purified by flash chromatography using a gradient of methanol in $CHCl_3$. The resulting 1-[N-(trifluoromethanesulfonyl)

amino]-3-O-dimethoxytritylmethyl-1-amino-2-propanol is phosphitylated with chloro-β-cyanoethoxy-N,N-diisopropylaminophosphine as per Example 20 to give the title compound.

EXAMPLE 80

1-[N-(Benzyl)amino]-3-O-dimethoxytritylmethyl-2-O-[(N,N-diisopropylamino)-2-cyanoethoxyphosphite]propane Chlorotrimethylsilane (6.0 mmol) is added dropwise to a solution of 1-amino-3-O-dimethoxytrityl-2-propanol (5.0 mmol), imidazole (5 mmol) and triethylamine (15 mmol) in 25 ml dry DMF. After stirring one hour the solvent is removed in vacuo, and the residue redissolved in acetonitrile (25 ml) and triethylamine (10 mmol). Benzyl bromide (6.0 mmol) is added, and stirring continued overnight. The reaction is quenched with saturated aqueous $NaHCO_3$, and the mixture stirred until the silyl ethers were hydrolyzed. The solvent is removed in vacuo, and the residue partitioned between water and ethyl acetate. The organic layer is washed with $NaHCO_3$, water, brine and dried with $Na_2SO_4$. The solvent is removed and the resulting oil purified by flash chromatography, using a gradient of methanol in $CHCl_3$. The resulting 1-[N-(benzyl)amino]-3-O-dimethoxytritylmethyl-1-amino-2-propanol is phosphitylated with chloro-β-cyanoethoxy-N,N-diisopropylaminophosphine as per Example 20 to give the title compound.

EXAMPLE 81

1-[N-(Aminocarbonyl)amino]-3-O-dimethoxytritylmethyl-2-O-[(N,N-diisopropyl-amino)-2-cyanoethoxyphosphite]propane Chlorotrimethylsilane (6.0 mmol) is added dropwise to a solution of 1-amino-3-O-dimethoxytrityl-2-propanol (5.0 mmol) and triethylamine (15 mmol) in 50 ml dry $CH_2Cl_2$. After one hour, dimethylaminopyridine (1 mmol) is added followed by trimethylsilyl isocyanate (5.5 mmol). The solution is stirred until the starting material is consumed. The solvent is removed in vacuo and the crude product redissolved in pyridine and $NaHCO_3$ solution to hydrolyze the TMS ethers. The solvent is evaporated, the residue partitioned between ethyl acetate and water, washed with $NaHCO_3$, brine and dried with $MgSO_4$. The residue is purified by flash chromatography using a gradient of methanol in $CHCl_3$. The resulting 1-[N-(aminocarbonyl)amino]-3-O-dimethoxytritylmethyl-2-propanolisphosphitylated with chloro-β-cyanoethoxy-N,N-diisopropylaminophosphine as per Example 20 to give the title compound.

EXAMPLE 82

1-[N-(Methylaminothiocarbonyl)amino]-3-O-dimethoxytritylmethyl-2-O-[(N,N-diisopropyl-amino)-2-cyanoethoxyphosphite]-propane Chlorotrimethylsilane (6.0 mmol) is added dropwise to a solution of 1-amino-3-O-dimethoxytrityl-2-propanol (5.0 mmol) and triethylamine (15 mmol) in 50 ml dry $CH_2Cl_2$. After one hour, dimethylaminopyridine (1 mmol) is added followed by methylisothiocyanate (5.5 mmol). The solution is stirred until the starting material is consumed. The solvent is removed in vacuo and the crude product redissolved in pyridine and $NaHCO_3$ solution to hydrolyze the TMS ethers. The solvent is evaporated, the residue partitioned between ethyl acetate and water, washed with $NaHCO_3$, brine and dried with $MgSO_4$. The residue is purified by flash chromatography using a gradient of methanol in $CHCl_3$. The resulting 1-[N-(methylaminothiocarbonyl)amino]-3-O-dimethoxytritylmethyl-2-propanol is phosphitylated with chloro-β-cyanoethoxy-N,N-diisopropylaminophosphine as per Example 20 to give the title compound.

EXAMPLE 83

N-α-(FMOC)-glutamic acid γ-benzyl ester

To a solution of γ-benzyl glutamate (10 mmol) in 50 ml dioxane and 50 ml water is added triethylamine (25 mmol), followed by a solution of fluorenylmethyl chloroformate (11 mmol) in 50 ml dioxane. The mixture is vigorously stirred until the starting material is consumed. The solution is acidified to pH 2 with concentrated HCl, extracted with ethyl acetate (2×250 ml), washed with brine, dried with $MgSO_4$ and evaporated. The product is used without purification.

EXAMPLE 84

N-α-(FMOC)-γ-benzyl-L-glutamic acid fluorenylmethyl ester

N-α-(FMOC)-glutamic acid γ-benzyl ester (5 mmol), fluorenylmethanol (5.5 mmol) and dimethylaminopyridine (0.5 mmol) are dissolved in 50 ml $CH_2Cl_2$. Dimethylaminopropyl ethyl carbodiimide (EDC, 6.0 mmol) is added, and the solution stirred at room temperature. After complete consumption of the starting material the solution is diluted with $CH_2Cl_2$, washed with 1% HCl, water and brine, dried with $MgSO_4$ and evaporated. The residue is purified by flash chromatography using ethyl acetate and hexane as eluant.

EXAMPLE 85

N-α-(FMOC)-L-glutamic acid α-fluorenylmethyl ester

N-α-(FMOC)-γ-benzyl-L-glutamic acid fluorenylmethyl ester (5 mmol) is dissolved in methanol (50 ml) and 10% Palladium on carbon is added (100 mg catalyst/mmol). The suspension is shaken under 30 psi $H_2$ until the starting material is consumed. The suspension is filtered through a short pad of Celite, washed thoroughly with methanol, and the solvent evaporated. The product is used directly without purification.

EXAMPLE 86

1-[N-(N-α-Fmoc-α-fluorenylmethyl-γ-glutamyl)amino]-3-O-dimethoxytritylmethyl-2-O-[(N,N-diisopropylamino)-2-cyanoethoxyphosphite]propane The title compound is prepared by the procedure of Example 54 using N-α-(FMOC)-L-glutamic acid α-fluorenylmethyl ester as the carboxylic acid component.

EXAMPLE 87

2-(N-Carbazolyl)acetic acid

The title compound is prepared as per Example 63 using carbazole as the starting heterocycle.

EXAMPLE 88

1-{N-[2-(N-Carbazolyl)acetyl]amino}-3-O-dimethoxytritylmethyl2-O-[(N,N-diisopropylamino)-2-cyanoethoxyphosphite]propane The title compound is prepared as per the procedure of Example 54 using N-carbazolyl-2-acetic acid as the carboxylic acid component.

EXAMPLE 89

N-Pyrrolyl-2-Acetic acid

The title compound is prepared as per Example 63 using pyrrole as the starting heterocycle.

EXAMPLE 90

1-{N-[2-(N-Pyrrolyl)acetyl]amino}-3-)-dimethoxytritylmethyl-2-O-[(N,N-diisopropylamino)-2-cyanoethoxyphosphite]propane The compound is prepared as per the procedure of Example 54 using N-pyrrolyl-2-acetic acid as the carboxylic acid component.

EXAMPLE 91

1-(1-Imidazole)-5-dimethoxytrityl-2-pentanol

1-Buten-4-ol is treated as per the procedure of Klunder, et al., *J. Org. Chem.* 1986, 51, 3710 to yield 4,5-epoxy-1-pentanol. The glycol is not isolated but is treated in situ in dry DMF with powdered potassium carbonate and imidazole as per the procedure of Example 4 followed by treatment with dimethoxytrityl chloride as per Example 5 to give the title compound.

EXAMPLE 92

1-(-Imidazole)-5-O-dimethoxytrityl-2-O-(N,N-diisopropylamino)-2-cyanoethoxyphosphite]pentane 1-(1-Imidazole)-4-dimethoxytrityl-2-pentanol is treated as per the procedure of Example 6 to give the title compound.

EXAMPLE 93

1-(1-Carbazole)-8-dimethoxytrityl-2-octanol

1-Octen-8-ol is treated as per the procedure of Klunder, et. al., *J. Org. Chem.* 1986, 51, 3710 to yield 4,5-epoxy-1-octanol. The glycol is not isolated but is treated in situ in dry DMF with powdered potassium carbonate and imidazole as per the procedure of Example 4 followed by treatment with dimethoxytrityl chloride as per Example 5 to give the title compound.

EXAMPLE 94

1-(-Carbazole)-8-O-dimethoxytrityl-2-O-[(N,N-diisopropylamino)-2-cyanoethoxyphosphite]octane 1-(1-Carbazole)-4-dimethoxytrityl-2-pentanol is treated as per the procedure of Example 6 to give the title compound.

EXAMPLE 95

1-(N-Morpholino)-2,3-propandiol

A rapidly stirred solution of redistilled morpholine (4.3 g, 50 mmole) and R-(+)-glycidol (3.7 g, 50 mmole) in anhydrous methyl alcohol (50 mL) was heated at reflux for 18 hr. The resulting solution was cooled and rotary evaporated to yield a light yellow syrup. This syrup was kept under vacuum for 3 hr to afford a quantitative yield of the propandiol (8.0 g) $^1$H-nmr (dmso-d$_6$): d, 4.5 (m, 2, hydroxyls); 3.5-3.3 (m, 7 ); 2.4-2.1 (m, 6).

EXAMPLE 96

1-(N-Morpholino)-3-O-dimethoxytrityl-2,3-propandiol

To an ice cold solution of 1-(N-morpholino)-2,3-propandiol (8.0 g, 50 mmole) in anhydrous pyridine (150 mL) and triethylamine (10 mL) was added powdered dimethoxytrityl chloride (17 g, 50 mmole) over a period of five minutes. This mixture was stirred at room temperature overnight and while maintaining anhydrous conditions. The resulting solution was rotary evaporated and then chromatographed on a 7.5×5 cm column using ethyl acetate/methyl alcohol/triethylamine (90/9.5/0.5) as eluant Yield of amber solid foam is 16 g (69%) $^1$H-nmr (dmso-d6): d, 7.5-6.8 (m, 13, aromatic); 3.9 (s, 6, methoxy) 10.4 and 5.7 (2 m, 1, hydroxyl); 4.2-2.8 (3 m, 13, aliphatic).

EXAMPLE 97

1-(N-Morpholino-3-O-dimethoxytrityl-2-O-[(N,N-diisopropylamino)-2-cyanoethoxyphosphite]-2,3-propanediol Chloro-β-cyanoethoxy-N,N-diisoproylaminophosphine (2.4 g, 1 mmole) was added to an ice cold solution of 1-(N-morpholino-3-O-dimethoxytrityl-2,3-propandiol (4.3 g, 1 mmole) in anhydrous tetrahydrofuran (50 mL) and diisopropyl ethylamine (5 mL). The solution was stirred at room temperature for 3 hr and then rotary evaporated. The gum which resulted was chromatographed on a 5.5×10 cm silica gel column using ethyl acetate/methanol/triethylamine (95/4.5/0.5) as eluent. The appropriate fractions were evaporated to yield the amidite.

EXAMPLE 98

1-(N-Piperidine)-2,3-propandiol

A rapidly stirred solution of piperidine (4.3 g, 50 mmole) and R-(+)-glycidol in anhydrous methanol (50 mL) was heated to reflux for 18 hr. The mixture was rotary evaporated to yield a clear syrup which was kept under vacuum for 3 hr to afford a quantitative yield of the propandiol (8 g). $^1$H-nmr (dmso-d$_6$): d, 4.6 and 4.3 (2 m, 2, hydroxyls); 3.6 (m, 1, methine); 3.3 and 2.3 (2 m, 4, propane); 1.4 (m, 10, 10 piperidine).

EXAMPLE 99

1-(N-Piperidine)-3-O-dimethoxytrityl-2,3-propandiol

To an ice cold solution of 1-(N-piperidine)-2,3-propandiol (6.8 g, 43 mmole) in pyridine (75 mL) and triethylamine (15 mL) was added dimethoxytrityl chloride (14.4 g, 43 mmole) over a period of five minutes. This mixture was stirred at room temperature overnight and while maintaining anhydrous conditions. The resulting solution was rotary evaporated and then chromatographed on a 11.5×5 cm column using ethyl acetate and then ethyl acetate/methyl alcohol/triethylamine (90/9.5/0.5) as eluant. The yield of yellow solid foam is 11 g (56%) $^1$H-nmr (dmso-d$_6$): d, 7.4-6.8 (m, 13, aromatic); 4.5 (m, 1, hydroxyl); 3.8 (s, 6, methoxy); 2.9 (d, 1, hydroxyl); 2.2 and 1.4 (2 m, 14, propane and piperidine)

EXAMPLE 100

1-(N-Piperidine-3-O-dimethoxytrityl-2-O-[(N,N-diisopropylamino)-2-cyanoethoxyphosphite]-2,3-propanediol Chloro-β-cyanoethoxy-N,N-diisoproylaminophosphine (2.4 g, 1 mmole) was added to an ice cold solution of 1-(N-piperidine)-3-O-dimethoxytrityl-2,3-propandiol (4.6 g, 1 mmole) and diisopropyl-ethylamine (5 mL). The reaction mixture was stirred at room temperature for 3 hr and then rotary evaporated to afford a colorless syrup. This syrup was chromatographed on a 5.5×10 cm column using ethyl acetate/methanol/triethylamine (95/4.5/0.5) to afford the amidite.

EXAMPLE 101

1-O-Dimethoxytrityl-5-hexen-1,2-diol

To a solution of 3-O-dimethoxytrityl-R-(+)-glycidol (8.0 g, 21 mmole) in anhydrous tetrahydrofuran (80 mL) at room temperature was added lithium tetrachlorocuprate (50 mL, 0.1M solution in THF, Aldrich) followed immediately by allylmagnesium bromide (70 mL, 1M solution in THF, Aldrich). The mixture was allowed to stir under an atomosphere of argon gas overnight and then quenched with the slow addition of a saturated aqueous solution of ammonium chloride (approx. 20 mL) . The mixture was further stirred for 30 minutes and then filtered through Celite. The filter bed was washed with additional THF and the filtrates evaporated. The resulting dark oil was chromatographed on a 5.5×10 cm silica gel column using hexanes/ethyl acetate/triethylamine (90/9.5/0.5) and then (80/19.5/0.5) as eluent. Evaporation of the appropriate fractions afforded the diol as a colorless oil, 8.0 g (90%). $^1$H-nmr (dmso-d$_6$): d, 7.5-6.8 (m, 13, aromatic); 5.8 and 5.0 (2 m, 3, alkene); 4.7 (d, 1, hydroxyl); 3.7 (s, 6, methoxy); 3.6 (m, 1, methine); 2.9 (m, 2, allyl); 2.1 and 1.6 (2 m, 4, methylene).

EXAMPLE 102

1-O-Dimethoxytrityl-2-O-[(N,N-diisopropylamino)-2-cyanoethoxyphosphite]-5-hexen-1,2-diol Chloro-β-cyanoethoxy-N,N-diisoproylaminophosphine (2.4 g, 1 mmole) was added to an ice cold solution of 1-O-dimethoxytrityl-5-hexen-1,2-diol (4.2 g, 1 mmole) in tetrahydrofuran (80 mL) and diisopropyl-ethylamine (5 mL). The mixture was stirred at room temperature for 3 hr and then rotary evaporated. The resulting oil was chromatographed on a 5.5×10 cm silica gel column using hexanes/ethyl acetate/triethylamine as eluent. The appropriate fractions were evaporated to afford the amidite.

EXAMPLE 103

2-O-Benzyl-1-O-dimethoxytrityl-5-hexen-1,2-diol

To a solution of 1-O-dimethoxytrityl-5-hexen-1,2-diol (2.0 g, 4.8 mmole) in anhydrous dimethylformamide (15 mL) was added 60% sodium hydride (0.28 g, washed with hexanes), followed immediately with benzyl bromide (0.82 g, 4.8 mmole). The mixture was stirred under an atomosphere of argon and at room temperature for 1 hr and then rotary evaporated. The resulting oil was partitioned between dichloromethane (150 mL) and cold, saturated sodium bicarbonate solution (50 mL). The organic layer was further washed with water, brine and then dried over sodium sulfate, filtered and rotary evaporated to afford a clear yellow oil. This material was filtered through a short bed of silica gel on a sintered glass funnel using ethyl acetate/hexanes (4/1) to afford a colorless oil, 2.0 g (82%). $^1$H-nmr (dmso-d$_6$): d, 7.5-6.8 (m, 18, aromatic); 5.8 and 4.9 (2 m, 3, alkene); 4.6 (q, 2, benzyl); 3.8 (s, 6, methoxy); 3.5 (m, 1, methine); 3.1, 2.0 and 1.6 (3 m, 6, methylene).

EXAMPLE 104

2-O-Benzyl-1-O-dimethoxytrityl-hexan-1,2,6-triol

A solution of 2-O-benzyl-1-O-dimethoxytrityl-5-hexen-1,2-diol (1.6 g, 3.1 mmole) in anhydrous tetrahydrofuran (25 mL) was treated with a diborane/THF complex (6.3 mL of 1M solution in THF) at room temperature. After frothing subsided (10 minutes from the addition of diborane), the mixture was further stirred under argon for 15 minutes. The mixture was treated with methanol (10 mL), stirred for 30 minutes at room temperature and then treated with NaOH solution (10 mL, 1N) and stirred for an additional 30 minutes. The mixture was rotary evaporated to a minimal volume and the residue which resulted was redissolved in tetrahydrofuran (50 mL), then treated with 30% hydrogen peroxide solution (6 mL). After 30 minutes, the biphasic solution was diluted with dichloromethane (100 mL) and the organic layer washed with cold water, cold, saturated sodium bicarbonate solution and brine. The organic layer was dried over sodium sulfate, filtered and evaporated. This material was chromatographed on a 3.5×15 cm silica gel column using hexanes/ethyl acetate/triethylamine (60/39.5/0.5) as eluent. The appropriate fractions were rotary evaporated to yield a colorless oil, 0.7 g (42%). $^1$H-nmr (dmso-d$_6$): d, 7.5-6.8 (m, 18, aromatic); 4.6 (q, 2, benzyl); 4.3 (t, 1, hydroxyl); 3.8 (s, 6, methoxy); 3.5 (m, 1, methine); 3.3, 3.1 and 1.3 (3 m, 10, methylene).

EXAMPLE 105

6-O-Benzoyl-2-O-benzyl-1-O-dimethoxytrityl-1,2,6-hexantriol

A solution of 2-O-benzyl-1-O-dimethoxytrityl-1,2,6-hexantriol (0.60 g, 1.14 mmole) in anhydrous pyridine was treated with benzoyl chloride (0.24 g, 1.71 mmole) and the mixture allowed to stir overnight under an atmosphere of argon. The reaction mixture was treated with a few milliliters of methyl alcohol and rotary evaporated. The resulting oil was partitioned between dichloromethane (50 mL) and cold, saturated sodium bicarbonate solution (25 mL). The organic layer was further washed with cold water and brine, then dried over sodium sulfate, filtered and rotary evaporated. The resulting material was chromatographed on a 3.5×15 cm silica gel column using hexanes/ethyl acetate/triethylamine (80/19.5/0.5) as eluent. The appropriate fractions were evaporated to yield a colorless oil, 0.57 g (80%). $^1$H-nmr (CDCl$_3$): d, 8.1-6.7 (3 m, 23 H, aromatic); 4.6 (q, 2, benzyl); 4.3 (t, 2, methylene); 3.8 (s, 6, methoxy); 3.6 (m, 1, methine); 3.2 (m, 2, methylene); 1.7 (m, 6, methylene).

EXAMPLE 106

6-O-Benzoyl-1-O-dimethoxytrityl-1,2,6-hexantriol

A solution of 6-O-Benzoyl-2-O-benzyl-1-O-dimethoxytrityl-1,2,6-hexantriol (0.5 g, 0.8 mmole) in tetrahydrofuran was added a 10% Pd/C catalyst (0.15 g) and the mixture placed under a balloon of hydrogen gas (2–3 lbs/in$^2$ for three days. The baloon was refilled and an equivalent portion of catalyst was added at the end of the first and second days, to a total of approximately 0.5 g. The mixture was filtered through Celite, the bed was washed with additional THF and the filtrates were rotary evaporated. The residue which resulted was chromatographed on a 3.5×10 cm silica gel column using hexanes/ethyl acetate/triethylamine (80/19.5/0.5) as eluent. The appropriate fractions were evaporated to afford 0.4 g (32%) of the triol as a colorless glass. $^1$H-nmr (CDCl$_3$): d 8.1 (d, 2, aromatic); 7.6 to 6.2 (m, 12, aromatic); 6.8 (d, 4, aromatic); 4.3 (t, 2, bz-O—CH$_2$—); 3.8 (s, 6, methoxy); 3.2 (ddd, 2, C$\underline{H}_2$—O-DMT); 2.4 (d, 1, hydroxyl); 1.9 to 1.4 (m, 6, CH$_2$).

EXAMPLE 107

6-O-Benzoyl-1-O-dimethoxytrityl-1,2,6-hexantriol-2-O-[(N,N-diisopropylamino)-2-cyanoethoxyphosphite]-1,2,6-hexantriol Chloro-β-cyanoethoxy-N,N-diisoproylaminophosphine was added to an ice cold solution of 6-O-benzoyl-1-O- dimethoxytrityl-1,2,6-hexantriol in tetrahydrofuran and diisopropylethylamine. The mixture was stirred at room temperature for 3 hr and then rotary evaporated. The resulting oil was chromatographed on a 5.5×10 cm silica gel column using hexanes/ethyl acetate/ triethylamine as eluent. The appropriate fractions were evaporated to afford the amidite.

EXAMPLE 108

1-O-Dimethoxytrityl-4-methylpentan-1,2-diol

A mixture of isopropylmagnesium bromide (50 mL of 2M solution in THF, Aldrich) and dilithium tetrachlorocuprate (10 30 mL of 0.1M solution in THF, Aldrich) was cooled to −68° C. under an atmosphere of argon. The mixture was treated dropwise with a solution of 3-O-dimethoxytrityl-R-(+)-glycidol (7.3 g, 20 mmole, in 30 mL THF) so as to maintain this temperature. The amber solution was warmed to room temperature and then stirred overnight. The mixture was treated with cold saturated ammonium chloride solution (approx. 30 mL) and the filtered through Celite. The Celite bed was washed several times with additional tetrahydrofuran and the filtrates were rotary evaporated The resulting yellow syrup was chromatographed on a 5.5×15 cm silica gel column using hexanes/ethyl acetate/triethylamine as eluent. The appropriate fractions were evaporated to yield 5.2 g ( ) of the diol as a colorless gum. $^1$H-nmr (dmso-d$_6$): d, 7.5-6.8 (m, 13, aromatic); 4.6 (d, 1, hydroxyl); 3.7 (s, 6, methoxy); 3.7 (m, 1, C-2 methine); 2.9 (2 m, 2, methylene); 1.7 (m, 1, C-4 methine); 1.2 (t, 2, methylene); 1.9 (2 d, 6, methyls).

EXAMPLE 109

1-O-Dimethoxytrityl-2-O-[(N,N-diisopropylamino)-2-O-cyanoethoxy-phosphite]-4-methylpentan-1,2-diol The N,N,N',N'-tetraisopropyl-2-cyanoethyldiphosphoramidite (3.3 g, 10.8 mmole) was added to an ice cold solution of 1-O-dimethoxytrityl-4-methylpentan-1,2-diol (3.8 g, 9 mmole) and diisopropylammonium tetrazolide (1.2 g, 4.5 mmole) in anhydrous acetonitrile (40 mL). This mixture was stirred overnight at room temperature and under an atmosphere of argon. The reaction mixture was evaporated to a minimal volume and the residue partitioned between dichloromethane (100 mL) and cold, saturated sodium bicarbonate solution (50 mL). The organic layer was further washed with cold water and brine and then dried over sodium sulfate, filtered and rotary evaporated. The syrup which resulted was chromatographed on a 5.5×15 cm silica gel column using hexanes/ethyl acetate/ triethylamine (80/19.5/0.5) as eluent. The appropriate fractions were rotary evaporated to afford 5.4 g (80%) of the amidite as a colorless glass. $^{31}$P-nmr (CD$_3$OD): 153.3, 152.9 ppm.

EXAMPLE 110

1-(N,N-Bis-cyanoethylamino)-2,3-propandiol

A solution of R-(+)-glycidol (0.5 g, 6.7 mmole) in anhydrous acetonitrile (30 mL) and triethylamine (0.5 mL) was treated with 3,3'-iminodipropionitrile (0.825 g, 6.7 mmole) The mixture was heated to 50° C. and stirred under an atmosphere of argon for 18 hr. The mixture was rotary evaporated under vacuum pump to afford 1.0 g (76%) of a light colorless oil. $^1$H-nmr (dmso-d$_6$): d, 4.9 (t, 1, 1° hydroxyl); 4.7 (d, 1, 20 hydroxyl); 3.7-3.2 (m, 5, propane); 2.7 and 2.6 (2 t, 8, ethylene).

EXAMPLE 111

1-([N,N-Bis-cyanoethyl]amino)-3-O-dimethoxytrityl-propan-2,3-diol

A solution of 1-([N,N-bis-cyanoethyl]amino)-2,3-propandiol in anhydrous pyridine was treated with dimethoxytrityl chloride and the mixture stirred under anhydrous conditions for 18 hr. The mixture was treated with a few milliliters of anhydrous methanol and then rotary evaporated. The resulting oil was coevaporated with toluene and then chromatographed on a silica gel column to afford the tritylated compound.

EXAMPLE 112

1-([N,N-Bis-cyanoethyl]amino)-3-O-dimethoxytrityl-2-O-[(N,N-diisopropylamino)-2-O-cyanoethoxyphosphite]-propan-2,3-diol Chloro-β-cyanoethoxy-N,N-diisoproylaminophosphine was added to an ice cold solution of 1-([N,N-biscyanotheyl]amino)-3-O-dimethoxytrityl-propan-2,3-diol and diisopropylethylamine in anhydrous tetrahydrofuran. The mixture was stirred at room temperature and under an atmosphere of argon for 3 hr, then rotary evaporated. The resulting mixture was chromatographed on a silica gel column and the appropriate fractions collected and rotary evaporated to afford the phosphoramidite.

EXAMPLE 113

1-(N,N'-Bis-carboxamidoethylamino)-3-O-dimethoxytrityl-propan-2,3-diol

A solution of 1-([N,N-bis-cyanoethyl]amino)-3-O-dimethoxytrityl-propan-2,3-diol in tetrahydrofuran was treated with aqueous 1M sodium hydroxide solution at room temperature. To the biphasic mixture solution at room temperature. To the biphasic mixture was added 30% hydrogen peroxide and then stirred at room temperature overnight. The resulting mixture was diluted with dichloromethane and the organic layer was further washed with cold, saturated sodium bicarbonate solution, water and brine. The organic layer was rotary evaporated and the resulting oil was filtered through a short bed of silica gel on a sintered glass funnel to afford the bis-carboxamide.

EXAMPLE 114

1-([N,N'-Bis-carboxamidoethyl]amino)-3-O-dimethoxytrityl-2O-[(N,N-diisopropylamino)-2-O-cyanoethoxyphosphite]-propan-2,3-diol Chloro-β-cyanoethoxy-N,N-diisopropylaminophosphine was added to an ice cold solution of 1-([N,N'-bis-carboxamidoethyl]amino)-3-O-dimethoxytrityl-propan-2,3-diol in anhydrous tetrahydrofuran and diisopropylethylamine. The resulting mixture was stirred at room temperature and under an atmosphere of argon for 3 hr, then rotary evaporated. The resulting mixture was chromatographed on a silica gel column and the appropriate fractions were collected and rotary evaporated to afford the phosphoramidite.

EXAMPLE 115

Standard Oligomer Coupling Cycle Using Standard DNA Synthesis Protocols

The oligomeric macromolecules of the invention are synthesized on an automated DNA synthesizer (Applied Bio-systems model 380B) as is done with standard oligonucleotides using standard phosphoramidate chemistry with oxidation by iodine (see *oligonucleotide synthesis, a practical approach,* M. J. Gait. Ed., Oxford University Press, New York, N.Y., 1990). For phosphorothioate oligomers, the standard oxidation bottle is replaced by 0.2M solution of 3H-1,2-benzodithiole-3-one 1,1-dioxide in acetonitrile for the step wise thiation of the phosphite linkages. The thiation wait step is increased to 68 sec and is followed by the capping step. After cleavage from the CPG column and deblocking in concentrated ammonium hydroxide at 55° C. (18 hr), the oligomers are purified by precipitation twice out of 0.5M NaCl solution with 2.5 volumes ethanol. Analytical gel electrophoresis is effected in 20% acrylamide, 8M urea, 454 mM Tris-borate buffer, pH=7.0. Phosphodiester and phosphorothioate oligomers are judged from polyacrylamide gel electrophoresis as to material length.

EXAMPLE 116

Synthesis of Sequence Specific Ethylene Glycol Oligomer Having Phosphodiester Linkages "Aforvirsen" is an anti-papilloma agent having the nucleobase sequence:

TTG CTT CCA TCT TCC TCG TC. SEQ ID NO:1

An ethylene glycol phosphodiester linked oligomer of this preselected sequence is prepared using the T, A, C and G reagents from Examples 3, 15, 24 and 20, respectively, as per the procedure of Example 115 using iodine as the oxidation reagent to give the phosphodiester linked oligomeric compound having the "Aforvirsen" sequence.

EXAMPLE 117

Synthesis of Sequence Specific Ethylene Glycol Oligomer Having Phosphorothioate Linkages "Aforvirsen" is an anti-papilloma agent having the nucleobase sequence:

TTG CTT CCA TCT TCC TCG TC. SEQ ID NO:1

An ethylene glycol phosphorothioate linked oligomer of this 35 preselected sequence is prepared using the T, A, C and G reagents from Examples 3, 15, 24 and 20, respectively, as per the procedure of Example 115 using 3H-1,2-benzodithiole-3-one 1,1-dioxide as the oxidation reagent to give the phosphorothioate linked oligomeric compound.

EXAMPLE 118

Hydrogen phosphonate Coupling: General Procedure.[1]

[1] Froehler, B. C. In *Methods in Molecular Biology,* vol 20: *Protocols for Oligonucleotides and Analogs.* Agrawal, S. Ed.; Humana Press: Totowa, 1993, 63–80.

A portion of solid support (CPG or other polymeric support e. g. TentaGel) derivatized with a DMT protected alcohol linked via a succinate linker (1 μmol) was loaded into a DNA synthesis column, and attached to an automated DNA synthesizer programmed to perform the following functions.

1) Wash with dichloromethane
2) DMT group was removed with 3% trichloroacetic acid in dichloromethane.
3) Wash with dichloromethane and CH$_3$CN/Pyridine (1:1).
4) Coupling: addition of alternating portions of 0.2M Adamantoyl chloride or Pivaloyl chloride in CH$_3$CN/Py (1:1) and 0.05M H-phosphonate monomer in CH$_3$CN/Py (1:1) for 1 min.
5) Wash with CH$_3$CN/Pyridine (1:1).
6) Repeat steps 1 through 5 until the full sequence is completed.

The product of this sequence of reactions is an H-phosphonate diester which is oxidized by one of several methods including those described below.

Oxidation procedure 1: Phosphodiester

The solid support-bound H-phosphonate diester is treated (manually or automatically) with equal volumes of solution A (0.2M I$_2$ in THF) and solution B (N-methylmorpholine/H$_2$O/THF 1:1:8) for 5 min, followed by equal volumes of solution A and solution C (TEA/H$_2$O/THF 1:1:8) for 5 min, followed by washing with CH$_3$CN/Py (1:1).

Oxidation procedure 2: Phosphorothioate

The solid support-bound H-phosphonate diester is treated (manually or automatically) with a solution of S$_8$ in CS$_2$/Lutidine for 30 min. The solid support is then washed with CH$_3$CN/Py (1:1).

Oxidation procedure 3: Phosphoramidate

The solid support-bound H-phosphonate diester is treated (manually or automatically) with a solution of the required amine (10% V/V) in CCl$_4$/Pyridine 1:1 for 15–30 min. The solid support is then washed with CH$_3$CN/Py (1:1).

Synthesis of Phosphoramidate Library with Uniform PN-Substitution, $X_{PN}(N_{PN})_n N$ The library is synthesized on Ethylene glycol CPG or on Universal Support CPG (Zeneca, Cambridge, UK) using an automated DNA synthesizer. The solid support is separated into a number of portions equal to the number of monomers used. Each monomer is coupled to the support using the H-phosphonate coupling general procedure. The portions are mixed and redivided for the next coupling. In this way, the random oligomers are synthesized until the fixed position is reached. The support is again split into portions and each monomer coupled. Additional monomers can be added after the fixed position by performing the couplings to the individual pools. Additional random positions can be added to the oligomer by further splitting each of the pools and recombining after coupling, taking care not to mix pools with different fixed positions. Once the oligomer assembly is complete, the H-phosphonate linkages in the individual subsets need to be oxidized, following general procedure 3. This has the result of producing the same phosphoramidate linkage between each residue in the library. By following oxidation general procedure 1 or 2 instead, an all phosphodiester or all phosphorothioate library is produced. The library pools are then cleaved from the solid support, purified and assayed for activity as described previously.

Synthesis of Phosphoramidate Library with fixed PN-Substitution, $X_{PN1}$-$N_{PN2}(N_{PNn})_m$-N Synthesis of a phosphoramidate library using 2-substituted-DMT-ethylene glycol-H-phosphonate monomers (P-Amidate: EGP, Variable amines, $X_{PN1}$-$N_{PN2}$-$(N_{PNn})_m$-N). The library is synthesized on Ethylene glycol CPG or on Universal Support CPG (Zeneca, Cambridge, UK) using an automated DNA synthesizer. The solid support is separated into a number of portions equal to the number of monomers used (X). Each monomer is coupled to the support using the H-phosphonate coupling general procedure. The portions are recombined, and the H-phosphonate diester linkage is converted to a phosphoramidate using Oxidation procedure 3. These steps are repeated (split, couple, combine), followed by Oxidation procedure 3 using a different amine for each randomized position in the oligomer. At the fixed position, the support is split, the monomers are coupled, but the subsets are kept separate for the oxidation step. After cleavage and workup, one obtains a library with randomized monomers and a different substituent at each phosphoramidate linkage. It is also possible to introduce phosphodiester and phosphorothioate linkages at any position in the oligomer library by substituting the appropriate oxidation procedure.

Synthesis of Phosphoramidate Library with Variable PN-Substitution, $X_{PNn}$-$(N_{PNn})_m$-N The library is synthesized on Ethylene glycol CPG or on Universal Support CPG (Zeneca, Cambridge, UK) using an automated DNA synthesizer. The solid support is separated into a number of portions equal to the number of monomers used. Each monomer is coupled to the support using the H-phosphonate coupling general procedure. The portions are recombined, mixed and separated into portions. Each portion is oxidized with a different amine following oxidation procedure 3, followed by combining and mixing of the supports. These steps (split, couple, mix, split, oxidize, mix) are repeated until the fixed position. The support is then split into portions, the monomer coupled, and the resin portions split again for oxidation following procedure 3. After workup, each subset has a unique monomer residue and phosphoramidate linkage, and an equimolar amount of each monomer and amine in the randomized portion. It is also possible to incorporate phosphodiester and phosphoramidate linkages randomly into the oligomers by oxidizing a portion of each H-phosphonate diester by following procedure 1 or 2.

EXAMPLE 119

Preparation of 3-Octyl-propan-1,2-diol-phosphodiester-thymidine-phosphodiester-thymidine Trimer A controlled pore glass resin derivatized with a 3'-5'phosphodiester linked dimer of thymidine [5'-Dmt-o-T-o-p(=o)-o-T-CPG] was synthesized in a standard manner. The resin (25.6 mg, 47.5 mmole/g resin) was detritylated using 3% trichloroacetic acid in dichloromethane and then sequentially washed with anhydrous acetonitrile and pyridine. The resin was vigorously agitated with a solution of the 3-octyl-1-O-dimethoxytritylpropandiol-2-H-phosphonate (25 mM) in adamantoyl chloride (50 mM) and pyridine for five minutes. The resin was then washed repeatedly with anhydrous pyridine and blown dry with argon gas. 1 mL of iodine/pyridine/water (2/90/8) solution was added to the column and the column was agitated vigorously. The column was subsequently washed with pyridine and acetonitrile and then blown dry with argon gas. Products were cleaved from the CPG by treatment with 1 mL concentrated ammonium hydroxide for 30 minutes. The ammonia solution was evaporated to dryness and then treated with 80% acetic acid in water for 30 minutes to remove the trityl group. An aliquot of the solution exhibited a single peak at 26.3 min by an HPLC analysis (Vyadec C-18 column, monitor at 260 nm, linear gradient of ammonium acetate buffer (pH 7)-acetonitrile, 0–75% acetonitrile in 52 minutes) corresponding to the phosphodiester trimer.

EXAMPLE 120

Preparation of 3-Octyl-propan-1,2-diol-morpholinophosphoramidate-thymidine-phosphodiester-thymidine Trimer A 1-O-dimethoxytrityl-3-octyl-propandiol-2-O-P(H)-O-T-O-P(=O)-O-T-CPG resin prepared as described in Examples 118 and 119 is vigorously shaken with 1 mL of a solution of morpholine/carbon tetrachloride/pyridine (1/5/5) for 30 minutes. The resin is sequentially washed with pyridine and then acetonitrile and then blown dry with argon gas. Products are cleaved from the CPG by treatment with 1 mL concentrated ammonium hydroxide for 30 minutes. The ammonia solution is evaporated to dryness and then treated with 80% acetic acid in water for 30 minutes to remove the trityl group. An aliquot of this solution is used for HPLC analysis of the resulting morpholinophosphoramidate trimer.

EXAMPLE 121

Preparation of 3-(N-Piperidine)-propan-1,2-diol-phosphodiester-thymidine-phosphodiester-thymidine Trimer A controlled pore glass resin derivatized with a 3'-5'phosphodiester linked dimer of thymidine [5'-Dmt-o-T-o-p(=o)-o-T-CPG] was synthesized in a standard manner. The resin (24.6 mg, 47.5 mmole/g resin) was detritylated using 3% trichloroacetic acid in dichloromethane and then sequentially washed with anhydrous acetonitrile and pyridine. The resin was vigorously agitated with a 1 mL solution of the 1-(N-piperidine)-3-O-dimethoxytritylpropandiol-2-H-phosphonate(25 mM) in adamantoyl chloride (50 mM) and pyridine for five minutes. The resin was then washed repeatedly with anhydrous pyridine and blown dry with argon gas. The column was added 1 mL of iodine/pyridine/water (2/90/8) solution and agitated vigorously. The column was subsequently washed with pyridine and acetonitrile and then blown dry with argon gas. Products were cleaved from the CPG by treatment with 1 mL concentrated ammonium hydroxide for 30 minutes. The ammonia solution was evaporated to dryness and the residue treated with 80% acetic acid in water for 30 minutes to remove the trityl group An aliquot of the solution exhibited a single peak at 12.4 min by an HPLC analysis under the conditions described before.

EXAMPLE 122

Preparation of 1-N-Piperidine-3-O-dimethoxytrityl-propandiol-2-morpholinophosphoranidate-thymidine-phosphodiester-thymidine Trimer A 3-O-dimethoxytrityl-1-N-piperidine-propandiol-2-O-(H)-O-T-O-P(=O)-O-T-CPG resin prepared as described in Examples 118 and 119 is vigorously shaken with 1 mL of a solution of morpholine/carbon tetrachloride/pyridine (1/5/5) for 30 minutes. The resin is sequentially washed with pyridine and then acetonitrile and then blown dry with argon gas. Products are cleaved from the CPG by treatment with 1 mL concentrated ammonium hydroxide for 30 minutes. The ammonia solution is evaporated to dryness and then treated with 80% acetic acid in water for 30 minutes to remove the trityl group. An aliquot of this solution is used for HPLC analysis of the resulting morpholinophosphoramidate trimer.

EXAMPLE 123

Incorporation Of Monomeric Units Into Oligomeric Structure Using Combinatorial Technique—General Procedure A solid support (universal support from Cambridge Research Biochemicals) is separated into portions of equal weight. The number of portions equals the number of monomers in the combinatorial library. Each portion is reacted with one of the desired amidites using tetrazole as catalyst, followed by oxidation of the phosphite triester to the phosphate as per the standard coupling cycle of Example 115. The DMT ether is cleaved using trichloroacetic acid in $CH_2Cl_2$ to regenerate the hydroxyl group at the end of the extended oligomer. The extent of the coupling reaction is optimized to be $\geq 90\%$ completed by varying the amidite concentration and total equivalents and the coupling time. After a coupling, the supports from individual coupling reactions are mixed thoroughly, then divided equally and amidites are again reacted individually to a portion of the support. This cycle is repeated for each random position until the 'fixed' position is reached.

At the 'fixed' position of the oligomer, each amidite is reacted individually to a portion of the support, but the portions are not mixed. Instead each subset is further divided into the number of portions corresponding to the number of monomers. Each portion of support is then reacted with a different amidite, followed by mixing as above. Repeating this cycle for each of the different subsets of supports results in randomization in positions following the fixed position in the sequence. The resulting subsets are unique only in the fixed position.

At completion of the oligomer synthesis, the oligomers are cleaved from the solid support and phosphate protecting groups removed by incubation for 1–2 hours at room temperature in concentrated ammonia. The supernatant containing the oligomer is then removed from the silica and incubated at 55° C. for 6–16 hours to cleave the protecting groups from the residues. The oligomer is desalted and protecting groups are removed by HPLC size exclusion chromatography.

EXAMPLE 124

Evaluation Of Coupling Efficiency Of Phosphoramidite Monomers

The following method is used to evaluate the ethylene glycol phosphoramidites or other phosphoramidites for suitability of use in a random sequence solid state oligomer synthesis. A solid-phase synthesis support containing an internal reference is used to determine coupling efficiency, estimate the extinction coefficient, and evaluate coupling-product quality of the test phosphoramidite monomers as follows:

A test monomer-support is selected as is an internal standard. Using dT as a symbol of thymidine, dC as a symbol for deoxy cytidine and other abbreviations as note in the text below, in an illustrative test system, thymidine bound to CPG, identified as dT-CPG, is used for the test monomer-support and 5'-O-acetyl capped cytosine bound to CPG, identified as 5'-Ac-dC-CPG, is used for the internal standard.

Reactive dT-CPG is mixed with a lesser molar equivalent of unreactive 5'-Ac-dC-CPG. The unreactive 5'-Ac-dC-CPG internal standard allows for accurate determination of unreacted dT present before and after a coupling reaction.

The peak area of dT can be identified as $A_T$ and the peak area of dC identified as $A_C$. The initial ratio of peak areas for dT and dC, i.e., $(A_T/A_C)_0$, is determined by cleavage, deprotection, and HPLC analysis of an aliquot of the CPG mixture. Measurements are taken at a wavelength of 260 nm. Relative moles of dC can be identified as C, and relative moles of dT can be identified as T. These are calculated from peak areas, $A_C$ and $A_T$, respectively, using known extinction coefficients: $C=A_C/\epsilon_C$ and $T=A_T/\epsilon_T$. Thus the relative peak area or molar amount of dT initially present can always be calculated from the peak area of dC:

$$\begin{aligned} A_{T0} &= (A_C)[(A_T/A_C)_0] \\ T_0 &= (C)[(T/C)_0] \end{aligned}$$

also, $$\begin{aligned} (C)(T/C) &= (A_C/\epsilon_C)[(A_T/\epsilon_T)/(A_C/\epsilon_C)] \\ &= (A_C/\epsilon_C)(A_T/A_C))(\epsilon_C/\epsilon_T) \end{aligned}$$

thus, $$\begin{aligned} (C)[(T/C)_0] &= (A_C/\epsilon_C))[(A_T/A_C)_0](\epsilon_C, \epsilon_T) \\ &= (A_C/\epsilon_T)[(A_T/A_C)_0] \end{aligned}$$

An amidite monomer of interest, identified as X, is reacted with an aliquot of the CPG mixture. Reacted CPG is cleaved and deprotected with ammonia, then analyzed by HPLC to determine: the area under the peak for dC, i.e., $A_C$; the area under the peak for unreacted dT, i.e., $A_{Tur}$; and the area under the peak for X-T dimer, i.e., $A_{XT}$. These values are used to calculate coupling efficiency, C.E., and X-T dimer extinction coefficient $\epsilon_{XT}$.

The coupling efficiency, C.E., is defined by the ratio of reacted dT, i.e., $T_r$, to total dT, i.e., $T_0$. Thus C.E.$=T_r/T_0$. Coupling efficiency can be determined from the relative moles of unreacted dT present before, i.e., $T_0$, and after, i.e., $T_{ur}$, coupling with X; all three are related by the equation:

$$T_0 = T_r + T_{ur}.$$

Since C.E. is a unit-less value, HPLC peak areas can be used instead of relative molar quantities to perform the calculation:

$$\begin{aligned} C.E. &= (T_r/T_0) \\ &= (T_0/T_0) - (T_{ur}/T_0) \\ &= 1 - (T_{ur}/T_0) \\ &= 1 - (A_{Tur}/\epsilon_T)/(A_{T0}/\epsilon_T) \\ &= 1 - (A_{Tur}/A_{T0}) \\ &= 1 - (A_{Tur})/[(A_C)[(A_T/A_C)_0]] \end{aligned}$$

The foregoing are all measurable quantities.

The extinction coefficient $\epsilon$ for X, i.e., $\epsilon_{X-T}$, in the given HPLC solvent system is determined from the C.E. for X and the relative areas of the HPLC peaks. The amount of X-T is equal to the amount of T that has reacted. $\epsilon$ for dimer X-T is defined as the peak area $A_{XT}$ divided by the moles of X-T dimer present XT, and is calculated as follows:

$$\begin{aligned} XT &= T_r \\ &= (C.E.) - (T_0) \\ \epsilon_{XT} &= (A_{XT}/XT) \\ &= (A_{XT})/(C.E.)(T_0) \\ &= (A_{XT})/(C.E.)(C)[(T/C)_0] \\ &= (A_{XT})/(C.E.)(A_C/\epsilon_T)[(A_T/A_C)_0] \end{aligned}$$

The foregoing are all measurable quantities.

Finally, the quality of the coupling-product X-T can be evaluated from the appearance of the HPLC chromatogram. Significant peaks (those summing >10% of product-peak area) other than those expected might also be addressed.

Often they are the desired X-T dimer that retains protective groups. Disappearance of these peaks with extended ammonia treatment will confirm that the monomer requires extended ammonia deprotection beyond the standard time. In other cases the extra peaks can be identified as undesirable side-products or in some case they cannot be identified. Generally, coupling efficiency of less than about 90%, a required ammonia deprotection time of greater than a few days, or the occurrence of side-products amounting to greater that 10% (by UV absorbance) can be selected as initial guidelines to judge the possibility of excluding an amidite from consideration for use in a particular set of amidites used in generating random oligomeric compounds.

EXAMPLE 125

Evaluation Of Coupling Efficiency Of Illustrative Ethylene glycol Phosphoramidite Monomer Ethylene glycol phosphoramidites are coupled to a dT-CPG solid-phase synthesis support forming dimers and trimers. Coupling is effected as per the general procedure of Example 124 Synthesis of the dimers and trimers is performed with an ABI 394 DNA synthesizer (Applied Biosystems, Foster City, Calif.) using standard DNA synthesis reagents and synthesis protocols, with the exception of an extended (5 minute) coupling time added to the synthesis cycle. The oligomers are cleaved from solid support by treatment with concentrated ammonia for 3 days at 4° C. The supernatant is removed from the support and heated in a sealed vial at 55° C. for eight hours. This solution is cooled, and the ammonia removed by evaporation. The oligomers are analyzed directly on reversed-phase HPLC column (Waters Nova-Pak Phenyl, cat. #10656; Millipore Corp., Milford, Mass.) using a gradient of 1% to 75% acetonitrile in 0.1M ammonium acetate, pH 7, over 50 minutes. The HPLC system is a Waters with a 991 detector, 625 LC pump, and 714 WISP autoinjector. Calculations are performed using data collected at a wavelength of 260 nm.

EXAMPLE 126

Synthesis of Ethylene Glycol Phosphate Oligomeric Library

Ethylene glycol phosphate oligomers (EGP) were synthesized using standard DNA phosphoramidite chemistry. The following six EGP phosphoramidites were incorporated into oligomeric library: adenine, guanine, cytosine, thymine, carbazole and imidazole. EGP phosphoramidites were dissolved in anhydrous acetonitrile ($CH_3CN$) to 0.2M, with the exception of EGP guanine ("egG") which was first dissolved in anhydrous dimethylformamide (DMF) to 2M and then further diluted to 0.2M with $CH_3CN$. EGP phosphoramidites were coupled to a 1–2 μmol controlled pore glass (CPG) support on an ABI 394 DNA synthesizer using the standard ABI cycle for a 1 μmol scale cyanoethyl phosphoramidite synthesis with the coupling wait time increased to 5 minutes. By substituting a 0.1M solution of 3H-1,2-benzodithiol-3-one 1,1-dioxide (Beaucage) in acetonitrile for the iodine oxidizing solution, phosphorothioate oligomers were also synthesized. The 5' dimethoxytrityl group (DMT) of an oligomer terminating in a 5' EGP residue was not removed prior to cleaving the oligomer from the CPG support. Detritylating the 5' hydroxyl before cleavage in ammonium hydroxide ($NH_4CH$) results in the hydrolysis of the 5'EGP residue as a cyclic phosphate.

EGP oligomers were cleaved from CPG in 1 ml 30% $NH_4OH$ for 1 hour at room temperature. Cleaved oligomer was deprotected in $NH_4OH$ at 55° C. overnight (typically 12–18 hours). $NH_4OH$ was then removed from oligomer by evaporation in the Savant speedvac. The 5' hydroxyl was deprotected by cleaving the DMT from the oligomer in 1 ml 80% acetic acid (HOAc) for 1 hour. HOAc was then removed from oligomer by evaporation in the speedvac.

The oligomers were resuspended in $H_2O$ and further purified by one or more of three methods of Example 127.

EXAMPLE 127

General Oligomer Purification Procedures

Procedure A—reverse phase HPLC chromatography

To desalt oligomers by reverse phase chromatography, the oligomer was loaded onto a reverse phase column in approx. 100 mM ammonium acetate ($NH_4oAc$) or sodium acetate (NaOAc). The column was washed with several column volumes (10–20) of $H_2O$ to desalt. The oligomer was eluted in a gradient of 0% to 100% methanol.

Procedure B—size exclusion chromatography

To desalt by size exclusion, the oligomer was loaded onto a size exclusion column, typically Sephadex G10 or G25 1.6×50 cm, that is connected to the HPLC and eluted in $H_2O$ at a flow rate of 0.5 ml/min. The oligomers elute from the column in approximately 2–3 hours followed by salts and protecting groups.

Procedure C—ethyl acetate extraction

The oligomers may also be purified from the protecting groups by ethyl acetate extraction; however, this method does not desalt the oligomer. After DMT cleavage with HOAc, the dried oligomer was resuspended in 1–2 ml $H_2O$. Ethyl acetate (1 ml) was added to the oligomer and vortexed to mix layers. After the $H_2O$ and ethyl acetate layers separate, the top layer, which is the ethyl acetate layer containing DMT and benzamide protecting groups, was removed from the $H_2O$ layer which contains the oligomer. Three extractions with ethyl acetate are sufficient to remove the DMT and benzamide from the oligomer.

After purification by chromatography or extraction, the oligomer was dried by evaporation in the speedvac. The oligomer was resuspended in $H_2O$, typically at 0.5–2 mM, and stored at $\leq -20°$ C.

EXAMPLE 128

Synthesis of $(dG)_4(egCB)_4(dG)_4$ and $(dG)_4(egIM)_4$ $(dG)_4$ Phosphodiester Oligomers Two syntheses were performed incorporating EGP carbazole phosphoramidite (egCB) and EGP imidazole phosphoramidite (egIM) with deoxyguanosine (dG) phosphoramidite, ABI Cat# 400327. The oligomers $(dG)4$ $(egCB)_4(dG)_4$ and $(dG)_4(egIM)_4(dG)_4$ were synthesized on two 1 μmol 500 Å G-CPG synthesis columns from Cruchachem, Cat# 19-7821-80. Amidites were diluted to 0.2M with anhydrous acetonitrile, Aldrich Cat# 27,100-4. Amidites dG, egCB and egIM were placed on three of the amidite positions (positions 1–8) of ABI 394 DNA synthesizer. The synthesis cycle used was the ABI standard 1 μmol scale cycle modified to increase the coupling wait time to 5 minutes; the 5'DMT was removed after each synthesis round.

Oligomers were cleaved in 1 ml 30% $NH_4OH$ for 1 hour using a dual syringe method. For each column, 1 ml of 30% $NH_4OH$ was drawn into a 3 ml slip tip polypropylene syringe. Tip of the filled syringe was placed into one end of the synthesis column; a second empty syringe was placed on the other end. The NH$_4$OH was pushed through the column with the syringes and allowed to react for 1 hour. Cleaved oligomers in NH$_4$OH were removed from the column and placed in Wheaton 4 ml glass screwcap vials tightly capped with Wheaton teflon lined caps. Oligomers were placed in a VWR 55° C. heating block for 16 hours to remove protecting groups from bases. Vials were placed in an ice bath for approximately 15 minutes to cool. After the vials were carefully opened to vent the NH$_4$OH, the oligomers were transferred to 1.5 ml Biostor screwcap polypropylene microtubes. Vials were placed in the Savant speedvac and excess NH$_4$CH evaporated from oligomers.

Oligomers were resuspended in approx. 500 µl H$_2$O and vortexed. Each oligomer was purified and desalted separately on a Delta-Pak Cartridge 5 µm C18 300 Å 3.9–150 equally, a mixed CPG synthesis scheme was used. At each randomized position, each phosphoramidite was individually coupled to an equal portion of CPG and detritylated; CPG was then transferred from the columns to a 4 ml glass screwcap vial with a teflon lined cap, mixed by inversion for 15 minutes and redistributed among the six columns for the next coupling. Once the fixed position X was coupled, the six subsets of the library were kept separate. The synthesis cycle used was the ABI standard 1 mol scale cycle modified to increase the coupling wait time to 5 minutes; the 5'DMT was removed after each synthesis round.

SYNTHESIS SCHEME FOR G$_4$(egCB)XN$_2$G$_4$

| | Column 1 | Column 2 | Column 3 | Column 4 | Column 5 | Column 6 |
|---|---|---|---|---|---|---|
| ROUND 1 | AGGGG | CGGGG | GGGGG | TGGGG | (egCB)GGGG | (egIM)GGGG |
| | | | CPG mixed and divided among 6 columns | | | |
| ROUND 2 | ANG$_4$ | CNG$_4$ | GNG$_4$ | TNG$_4$ | (egCB)NG$_4$ | (egIM)NG$_4$ |
| | | | Mixed and divided among 6 columns | | | |
| ROUND 3 | G$_4$(egCB) | G$_4$(egCB) | G$_4$(egCB) | G$_4$(egCB) | G$_4$(egCB) | G$_4$(egCB) |
| | AN$_2$G$_4$ | CN$_2$G$_4$ | GN$_2$G$_4$ | TN$_2$G$_4$ | (egCB)N$_2$G$_4$ | (egIM)N$_2$G$_4$ |
| | | | Columns were kept separate from this point | | | | mm reverse phase column, Millipore Cat# 011793. Column was equilibrated for 20 minutes in 125 mM NH$_4$OAc at 1 ml/min. Oligomer was injected onto column; column was washed with 125 mM NH$_4$OAc for 5 minutes. Column was then washed with H$_2$O for 36 minutes to desalt oligomer and remove benzamide. Oligomer was eluted in 75% methanol for 6 minutes, followed by a 6 minute 100% methanol wash. Fractions eluting during the 75%–100% methanol wash were pooled in a polypropylene centrifuge tube. Excess solvent is evaporated from the oligomer in the speedvac. Oligomers are resuspended in H$_2$O to approximately 1 mM concentration and stored frozen at –20° C.

EXAMPLE 129

Synthesis of Phosphodiester Library G$_4$XN$_3$G$_4$

A library of oligomers was prepared incorporating two EGP phosphoramidites (carbazole (egCB) and imidazole (egIM)) with the four DNA (dA, dC, dG, and dT) phosphoramidites. The library consists of 6 subsets of the sequence G$_4$XN$_3$G$_4$. For each of the 6 subsets, position X is fixed as dA, dC, dG, dT, egCB, or egIM; N is a randomized position incorporating dA, dC, dG, dT, egCB, and egIM equally. This library was synthesized on a 2 µmol scale. Six empty 1 µmol scale Snap synthesis columns from ABI were filled with 2 µmol of dG-CPG, CPG Inc. Cat# DG200503 (2 µmol=45 mg of 44.5 µmol/g G-cpg). Amidites were diluted to 0.2M with anhydrous acetonitrile, Aldrich Cat# 27,100-4. Amidites dA, dG, dC, dT, egCB and egIM were placed on bottle positions 1–6, respectively, of the ABI 394 DNA synthesizer.

Coupling rates of the different amidites varied. To ensure each randomized position N incorporated all six residues Oligomers were cleaved in 1 ml 30% NH$_4$OH for 1 hour using a dual syringe method. Oligomers were placed at 55° C. for 16 hours to deprotect bases. Oligomers were then placed in the Savant speedvac and excess NH$_4$OH was evaporated.

Oligomers were resuspended in approximately 500 µl H$_2$O and vortexed. Each oligomers was purified and desalted separately on a Radial-Pak™ Cartridge 8×100 mm Delta-Pak™ C18 300 Å 15 µm reverse phase column, Waters Cat# WAT025845. Column was equilibrated for 20 minutes in 125 mM NH$_4$OAc at 3 ml/min. Oligomer was injected onto column; column was washed with 125 mM NH$_4$OAc for 5 minutes. Column was then washed with H$_2$O for 35 minutes to desalt oligomer and remove benzamide. Oligomer was eluted in 75% methanol for 10 minutes, followed by a 10 minute 100% methanol wash. Fractions eluting during the 75% methanol wash were pooled in a polypropylene centrifuge tube and excess solvent evaporated from the oligomer in the speedvac. Oligomers were resuspended in 1 ml H$_2$O, transferred to 1.5 ml Biostor screwcap microtubes and dried by evaporation in the speedvac. Oligomers were resuspended in H$_2$O to approx 2 mM concentration and stored frozen at –20° C.

The library was screened at Southern Research Institute (SRI) in an acute HIV assay. The oligomer subset in which X was fixed at egCB (i.e., G$_4$(egCB)N$_3$G$_4$) was the most active of the 6 subsets with an I.C.$_{50}$ of 3 µM.

The next round of syntheses (G$_4$(egCB)XN$_2$G$_4$) for this library was synthesized on a 2 µmol scale by the mixed CPG method described previously. The synthesis cycle used was the ABI standard 1 µmol scale cycle modified to increase the coupling wait time to 5 minutes; the 5'DMT was removed after each synthesis round.

|         | Column 1 | Column 2 | Column 3 | Column 4 | Column 5 | Column 6 |
|---------|----------|----------|----------|----------|----------|----------|
| ROUND 1 | AGGGG    | CGGGG    | GGGGG    | TGGGG    | (egCB)GGGG | (egIM)GGGG |
|         |          | CPG mixed and divided among 6 columns | | | | |
| ROUND 2 | $ANG_4$  | $CNG_4$  | $GNG_4$  | $TNG_4$  | $(egCB)NG_4$ | $(egIM)NG_4$ |
|         |          | Mixed and divided among 6 columns | | | | |
| ROUND 3 | $AN_2G_4$ | $CN_2G_4$ | $GN_2G_4$ | $TN_2G_4$ | $(egCB)N_2G_4$ | $(egIM)N_2G_4$ |
|         |          | Mixed and divided among 6 columns | | | | |
| ROUND 4 | $G_4AN_3G_4$ | $G_4CN_3G_4$ | $G_4N_3G_4$ | $G_4TN_3G_3$ | $G_4(egCB)N_3G_4$ | $G_4egIM)N_3G_4$ |
|         |          | Columns were kept separate from this point | | | | |

Oligomers were cleaved in 1 ml 30% $NH_4OH$ for 1 hr using a dual syringe method and heated at 55° C. for 16 hours to remove protecting groups from bases. Oligomers were placed in the Savant speedvac and excess $NH_4OH$ evaporated from oligomers.

Oligomers were resuspended in approximately 500 μl $H_2O$ and vortexed. Each oligomer was purified and desalted separately on a Pharmacia 16/50 HR column, Cat# 18-1460-01, packed with Sephadex G25 resin, Cat# 17-0572-01. Column was packed and equilibrated in $H_2O$ at 1–2 ml/min. Oligomer was injected onto column and flow rate was reduced to 0.5 ml/min. Oligomer eluted from column in 2 hours. Flow rate was then increased to 1–2 ml/min to quickly elute the salts and protecting groups and re-equilibrate the column. Fractions containing the oligomer were pooled in a polypropylene centrifuge tube and excess $H_2O$ was evaporated from the oligomer in the speedvac. Oligomers were resuspended in 1 ml $H_2O$, transferred to 1.5 ml Biostor screwcap microtubes and dried by evaporation in the speedvac. Oligomers were resuspended in $H_2O$ to approximately 1–2 mM concentration and stored frozen at −20° C.

EXAMPLE 130

Synthesis of $G_4XN_3G_4$ Phosphorothioate Library

A phosphorothioate version of the same library $G_4XN_3G_4$ was synthesized on a 2 μmol scale using the mixed mode method and synthesis scheme described previously; the 5'-DMT was removed after each synthesis round. The synthesis cycle used was the ABI standard 1 μmol scale cycle modified to increase the coupling wait time to 5 minutes. Additionally, the oxidation step using a solution of iodine and $H_2O$ was replaced with a sulfurization section. A 0.1M Beaucage solution in acetonitrile was placed on the synthesizer at position #10. The cycle was modified to deliver Beaucage solution to the column after the coupling step. After a 30 second wait step, the column is rinsed with acetonitrile followed by a capping procedure.

Oligomers were cleaved in 1 ml 30% $NH_4OH$ for 1 hour using a dual syringe method and heated at 55° C. for 16 hours to remove protecting groups from bases. Oligomers were desalted by G-25 size exclusion chromatography as described previously and stored frozen at 1 1mM in $H_2O$.

EXAMPLE 131

Synthesis of $XN_5T$ Phosphodiester Library

A library of oligomers was prepared incorporating six EGP phosphoramidites: adenine (egA), guanine (egG), cytosine (egC), thymine (egT), carbazole (egCB) and imidazole (egIM) phosphoramidites. The library consists of 6 subsets of the sequence $XN_5T$. For each of the 6 subsets, position X is fixed at egA, egC, egG, egT, egCB, or egIM; N is a randomized position incorporating egA, egC, egG, egT, egCB and egIM equally. This library was synthesized on a 2 μmol scale. Six empty 1 μmol scale Snap synthesis columns from ABI were filled with 2 μmol of dT-CPG, CPG Inc. Cat# DT06H012 (2 μmol=51 mg of 39.2 μmol/g dT-CPG). Amidites were diluted to 0.2M with anhydrous acetonitrile, Aldrich Cat# 27,100-4, with the exception of egG which was first dissolved in anhydrous DMF to 2 μM and then further diluted to 0.2 μM with $CH_3CN$. Amidites egA, egG, egC, egT, egCB and egIM were placed on bottle positions 1–6, respectively, of the ABI 394 DNA synthesizer. This library was synthesized by the mixed CPG method described previously using the ABI standard 1 μmol scale cycle modified to increase the coupling wait time to 5 minutes. The 5'-DMT was removed after synthesis segments 1–5; the 5'-DMT was not removed after synthesis segment 6 as this would allow the 5'-EGP residue to hydrolyze during cleavage in $NH_4OH$.

| SYNTHESIS SCHEME FOR $XN_5T$ | | | | | |
|---|---|---|---|---|---|
| Column 1 | Column 2 | Column 3 | Column 4 | Column 5 | Column 6 |
| ROUND 1  AT | CT | GT | TT | (egCB)T | (egIM)T |
|  | Mixed and divided among 6 columns | | | | |
| ROUND 2  ANT | CNT | GNT | TNT | (egCB)NT | (egIM)NT |
|  | Mixed and divided among 6 columns | | | | |
| ROUND 3  $AN_2T$ | $CN_2T$ | $GN_2T$ | $TN_2T$ | $(egCB)N_2T$ | $(egIM)N_2T$ |
|  | Mixed and divided among 6 columns | | | | |
| ROUND 4  $AN_3T$ | $CN_3T$ | $GN_3T$ | $TN_3T$ | $(egCB)N_3T$ | $(egIM)N_3T$ |
|  | Mixed and divided among 6 columns | | | | |
| ROUND 5  $AN_4T$ | $CN_4T$ | $GN_4T$ | $TN_4T$ | $(egCB)N_4T$ | $(egIM)N_4T$ |
|  | Mixed and divided among 6 columns | | | | |
| ROUND 6  $AN_5T$ | $CN_5T$ | $GN_5T$ | $TN_5T$ | $(egCB)N_5T$ | $(egIM)N_5T$ |
|  | Columns were kept separate from this point | | | | |

Oligomers were cleaved in 1 ml 30% $NH_4OH$ for 1 hour using a dual syringe method and heated at 55° C. for 16 hours to remove protecting groups from bases. Oligomers were transferred to a 6 ml polypropylene test tube and placed in the Savant speedvac to evaporate excess $NH_4OH$ from oligomers. 800 µl of 80% HOAc was added to the dry oligomer for 1 hour to cleave the DMT protecting group from the 5'-hydroxyl. Acid was removed by evaporation in the speedvac.

Oligomers were vortexed in 1 ml $H_2O$ to resuspend and benzamide and DMT protecting groups were removed from crude syntheses by ethyl acetate extraction. One milliliter of ethyl acetate was pipetted into the crude oligomer. Test tube was vortexed to thoroughly mix the $H_2O$ and ethyl acetate. After the layers had settled, revealing a clear solvent front between them, the top ethyl acetate layer was removed with a polypropylene pipet. The $H_2O$ layer was extracted two additional times with 2×1 ml of ethyl acetate. The $H_2O$ layer, which contains the oligomer, was evaporated to dryness to remove residual ethyl acetate.

Oligomers are resuspended in $H_2O$ to approx. 1–2 mM concentration and stored frozen at −20° C.

EXAMPLE 132

PLA2 assay

Phospholipase A2 (PLA2) enzymes are responsible for the hydrolysis of the sn-2 linkage of membrane phospholipids. PLA2-catalyzed reaction is the rate-limiting step in the release of a number of pro-inflammatory mediators, and type II PLA2 is implicated in the pathogenesis of several human inflammatory diseases. Library subsets were screened for inhibition of the activity of type II PLA2 and a unique inhibitor was identified.

The oligomer libraries were screened for inhibition of $PLA_2$ in an assay using *E. coli* cells labeled with $^3H$-oleic acid as the substrate. Franson et al., *J. Lipid Res.* 1974, 15, 35 380; and Davidson et al., *J. Biol. Chem.* 1987, 262, 1698. Type II $PLA_2$ (originally isolated from synovial fluid), expressed in a baculovirus system and partially purified, serves as a source of the enzyme. A series of dilutions (in water) of each of the oligomeric pools was made: 10 µL of each oligomer was incubated for 5 minutes at room temperature with a mixture of 10 µL of $PLA_2$, 20 µL 5×$PLA_2$, buffer (500 mM Tris, pH 7.0–7.5, 5 mM CaCl2) and 50 µL water. Each of the oligomer samples was run in duplicate. At this point, 10 µL of $^3H$-labeled *E. coli* cells was added. This mixture was incubated at 37° C. for 15 minutes. The enzymatic reaction was halted with the addition of 50 µL of 2M HCl and 50 µL of fatty acid-free BSA (20 mg/mL PBS), vortexed for 5 seconds and centrifuged at high speed for 5 minutes. A 165 µL portion of each supernatant was then put into a scintillation vial containing 6 mL of scintillant (Scintiverse) and cpms were measured in a Beckman Liquid Scintillation Counter. As a control, a reaction without oligomer was run alongside the other reactions as well as a baseline reaction containing neither oligomer nor $PLA_2$ enzyme. Cpms were corrected for by subtracting the baseline from each reaction data point. The results are shown in Tables III, IV, and V.

TABLE III

| Round | Sequence* | Most Active X = | $IC_{50}$ (µM) |
|---|---|---|---|
| 1 | $G_4$XNNN$G_4$ | egCB | 25 |
| 2 | $G_4$(egCB)XNN$G_4$ | egCB | 12 |

*N represents an equimolar mixture of dA, dG, dC, dT, egCB and egIM.

The first round identified $G_4$(egCB)NNN$G_4$ as the best oligomer with an $IC_{50}$ of 25 µM. The next position was also determined to be egCB, with a two-fold improvement in activity and an $IC_{50}$ of 12 µM. As a result, at the end of two rounds of selection, $G_4$(egCB)$_2$NN$G_4$ was identified to the best oligomer in the $PLA_2$ assay.

TABLE IV

| Round | Sequence* | Most Active X = | $IC_{50}$ (µM) |
|---|---|---|---|
| 1 | XNNNdT | noC | 30 |
| 2 | (noC)XNNdT | noC | 20 |
| 3 | (noC)(noC)XNdT | dG | 10 |
| 4 | (noC)(noC)dGXdT | dT | 2 |

The first two rounds were useful for the determination of the first two monomer units, i.e. noC, of the oligomer. The next two positions were determined to be dG and dT, in that order, and the unique oligomer with the greatest activity was identified to be (noC)(noC)(dG)(dT)(dT) with an $IC_{50}$ of 2 µM.

TABLE V

| Round | Sequence* | Most Active X = | $IC_{50}$ (µM) |
|---|---|---|---|
| 1 | XNNNNdT | egOC | 40 |
| 2 | (egOC)XNNNdT | egOC | 5 |
| 3 | (egOC)(egOC)XNNdT | egOC | 1.5 |

*N represents an equimolar mixture of egIM, egOC, egNH, hpPH, hpSU and hpNY.

The first round selected (egOC)NNNNdT as the most active subset with an $IC_{50}$ of 40 µM. The next round led to the determination of the monomer unit in the second position of the oligomer, i.e. egoC, with an eight-fold improvement in activity and an $IC_{50}$ of 5 µM. The third round of synthesis and selection led to the identification of (egOC)(egOC)—(egOC)NNdT as the most active subset with a still further improved $IC_{50}$ of 1.5 µM. Further rounds can be used to identify a unique oligomer with the greatest activity in the $PLA_2$ assay.

EXAMPLE 133

Verification Of Assay

The PLA2 test system of Example 132 was verified using phosphorothioate oligonucleotides with one or more strings of guanosine nucleotides (at least 3 per string). Libraries of these oligonucleotides were deconvoluted using the SURFs screening strategy and were shown to have an inhibitory effect on the $PLA_2$ enzyme. Knowing that phosphorothioate oligonucleotides inhibit $PLA_2$ with some sequence specificity, an eight nucleotide phosphorothioate library consisting of the four natural bases was used to test the assay system for suitability as a SURF screen. This library had been synthesized for use in another system and all subsets were not still available (indicated by dashes in Table III, below). Using the SURF method, it was confirmed that a stretch of guanosines were necessary for inhibition of $PLA_2$ activity by the phosphorothioate oligonucleotide (Table VI, below).

The assay was sensitive and accurate enough to discriminate between subsets of oligomers so that an inhibitory sequence could be selected. In each of the first three rounds of selection, the most active subset was readily determined. After 5 rounds, there was little difference in the activity of the subsets with at least 5 G's in a row, suggesting that the terminal positions are not critical for the inhibitory activity. The $IC_{50}$ of the "winner" improves (enzyme activity decreases) as more of the positions are fixed. As a test of the reproducibility of the assay, an eight nucleotide phosphorothioate oligonucleotide of a single sequence (TTGGGGTT) was assayed with each round of testing. This oligonucleotide acted as an internal control of the accuracy of the assay; the $IC_{50}$ was 8 µM in each assay.

TABLE VI

Inhibition of $PLA_2$ Activity by Library

| | Subsets $IC_{50}$ (mM) | | | |
|---|---|---|---|---|
| | X = A | X = G | X = C | X = T |
| Round 2 NNGNXNNN | >50 | 25 | >50 | >50 |
| Round 3 NNGXGNNN | — | 10 | >50 | — |
| Round 4 NNGGGXNN | 9 | 4 | 6 | 18 |
| Round 5 | | | | |
| NAGGGGXN | 4 | 2 | 4 | 4 |
| NGGGGGXN | 2.5 | 2 | 3 | 3 |
| NCGGGGXN | 5 | 4 | 5 | 5 |
| NTGGGGXN | 19 | 5 | 17 | 15 |

EXAMPLE 134

Assay of Library of Ethylene Glycol Oligomeric Compounds Against $PLA_2$

A library containing the ethylene glycol monomers is tested in the $PLA_2$ assay for identification of inhibitors of type II $PLA_2$. Confirmation of the "winner" is made to confirm that the oligomer binds to enzyme rather than substrate and that the inhibition of any oligomer selected is specific for type II $PLA_2$. An assay using $^{14}C$-phosphatidyl ethanolamine ($^{14}C$-PE) as substrate, rather than E. coli membrane, is used to insure enzyme rather than substrate specificity. Micelles of $^{14}C$-PE and deoxycholate are incubated with the enzyme and oligomer. $^{14}C$-labeled arachidonic acid released as a result of $PLA_2$-catalyzed hydrolysis is separated from substrate by thin layer chromatography and the radioactive product is quantitated. The "winner" is compared to phosphatidyl ethanolamine, the preferred substrate of human type II $PLA_2$, to confirm its activity. $PLA_2$ from other sources (snake venom, pancreatic, bee venom) and phospholipase C, phospholipase D and lysophospholipase can be used to further confirm that the inhibition is specific for human type II $PLA_2$.

Using a phosphodiester library of the composition:

GGGGXNNNGGGG SEQ ID NO:2 wherein each of X and N positions were ethylene glycol monomers as described above, the most potent compound is the compound wherein the X monomer has a carbazole functional group. This compound has an $IC_{50}$ of 25 µM. In the next most potent compound the X monomer has an adenine functional group.

Using a phosphorothioate library of the same composition, the most potent compound also is the compound where the X monomer has a carbazole functional group. However, in this library in the next most potent compound the X monomer has a cytosine functional group.

EXAMPLE 135

Preparation of Library of Mixed Ethylene glycol and Nucleotide Oligomeric Compounds Against $PLA_2$ A 5 mer phosphodiester library of the composition "NNNNT" was prepared wherein each N position was one of novel ethylene glycol monomers of the invention or nucleotides. A total of twelve monomers (all as a phosphoramidate suitable for oligomerization) and a null position were used in preparing the library. The monomeric units included the imidazole and carbazole ethylene glycol monomeric phosphoramidates of Examples 6 and 9 above, respectively, guanosine and cytidine deoxynucleotide phosphoramidates, 2'-O-methyl adenosine and uridine nucleotide phosphoramidates, 2'-O-nonyl cytidine nucleotide phosphoramidates, 2'-O-pentyl guanosine nucleotide phosphoramidate, N2,2'-O-dimethyl uridine nucleotide phosphoramidate, 1-amino-propane glycol phosphoramidate (the product from the 1-[N-benzoyl)amino]propane glycol phosphoramidate of Example 35 after deblocking of the amino group with base upon completion of oligomer synthesis) and a benzotriazole deoxynucleotide phosphoramidate).

EXAMPLE 136

Hybridization probe for the detection of specific mRNA in biological sample

For the reliable, rapid, simultaneous quantification of multiple varieties of mRNA in a biological sample without the need to purify the mRNA from other cellular components, a mRNA of interest from a suitable biological sample, i.e., mRNA of a blood borne virus, a bacterial pathogen product in stool, urine and other like biological samples, is identified using standard microbiological techniques. An oligomeric compound of the invention complementary to the nucleic acid sequence of this mRNA is prepared as per the above examples. The oligomeric compound is immobilized on insoluble CPG solid support utilizing the procedure of Pon, R. T., Protocols for Oligonucleotides and Analogs, Agrawal, S., Ed., Humana Press, Totowa, N.J., 1993, p 465–496. Using the method of PCT application WO 93/15221, a known aliquot of the biological sample under investigation is incubated with the insoluble CPG support having the oligomer thereon for a time sufficient to hybridize the mRNA to oligomer and thus to link the mRNA via the oligomer to the solid support. This immobilizes mRNA present in the sample to the CPG support. Other non-immobilized materials and components are then washed off the CPG with a wash media suitable for use with the biological sample. The mRNA on the support is labelled with ethidium bromide, biotin or a commercial radionucleotide and the amount of label immobilized on the CPG support is measured to indicate the amount of mRNA present in the biological sample.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

EXAMPLE 137

Leukotriene $B_4$ assay

Leukotriene $B_4$ ($LTB_4$) has been implicated in a variety of human inflammatory diseases, and its pharmacological effects are mediated via its interaction with specific surface cell receptors. Library subsets were screened for competitive inhibition of radiolabeled $LTB_4$ binding to a receptor preparation.

A Nenquest™ Drug Discovery System Kit (NEN Research Products, Boston, Mass.) was used to select an inhibitor of the interaction of Leukotriene $B_4$ ($LTB_4$) with receptors on a preparation of guinea pig spleen membrane. [$^3$H] Leukotriene $B_4$ reagent was prepared by adding 5 mL of ligand diluent (phosphate buffer containing NaCl, $MgCl_2$, EDTA and Bacitracin, pH 7.2) to 0.25 mL of the radioligand. The receptor preparation was made by thawing the concentrate, adding 35 mL of ligand diluent and swirling gently in order to resuspend the receptor homogenously. Reagents were kept on ice during the course of the experiment, and the remaining portions were stored at −20° C.

The library subsets were diluted to 5 $\mu$M, 50 $\mu$M and 500 $\mu$M in phosphate buffer (1×PBS, 0.1% azide and 0.1 BSA, pH 7.2), yielding final test concentrations of 0.5 $\mu$M, 5 $\mu$M and 50 $\mu$M, respectively. Samples were assayed in duplicate. [$^3$H] $LTB_4$ (25 $\mu$L) was added to 25 $\mu$L of either appropriately diluted standard (unlabeled $LTB_4$) or library subset. The receptor suspension (0.2 mL) was added to each tube. Samples were incubated at 4° C. for 2 hours. Controls included [$^3$H] $LTB_4$ without receptor suspension (total count vials), and sample of ligand and receptor without library molecules (standard).

After the incubation period, the samples were filtered through GF/B paper that had been previously rinsed with cold saline. The contents of each tube were aspirated onto the filter paper to remove unbound ligand from the membrane preparation, and the tubes washed (2×4 mL) with cold saline. The filter paper was removed from the filtration unit and the filter disks were placed in appropriate vials for scintillation counting. Fluor was added, and the vials shaken and allowed to stand at room temperature for 2 to 3 hours prior to counting. The counts/minute (cpm) obtained for each sample were subtracted from those obtained from the total count vials to determine the net cpm for each sample. The degree of inhibition of binding for each library subset was determined relative to the standard (sample of ligand and receptor without library molecules). The results are shown in Tables VII, VIII, and IX.

TABLE VII

| Round | Sequence* | Most Active X = | $IC_{50}$ ($\mu$M) |
|---|---|---|---|
| 1 | XNNNNNdT | egCB | 11 |
| 2 | (egCB)XNNNNdT | egCB | 2 |
| 3 | (egCB)(egCB)XNNNdT | egCB | 0.7 |

*N represents an equimolar mixture of egA, egG, egC, egT, egCB and egIM.

In the initial round of screening, the subset with egCB in the first position, i.e. (egCB)NNNNNdT, showed greatest activity. In the second round, subset (egCB) (egCB) NNNNdT was most active, and the activity increased from an $IC_{50}$ of 11 $\mu$M in round 1 to 2 $\mu$M in round 2, an approximately 6-fold increase in activity. Assay of round 3 subsets resulted in the identification of (egCB) (egCB) (egCB)NNNdT with improved activity and an $IC_{50}$ of 0.7 $\mu$M. Synthesizing and assaying further rounds of subsets leads to the identification of a unique oligomer demonstrating the best activity in the $LTB_4$ assay.

TABLE VIII

| Round | Sequence* | Most Active X = | $IC_{50}$ ($\mu$M) |
|---|---|---|---|
| 1 | XNNNdT | egCB | 40 |
| 2 | (egCB)XNNdT | egCB | 6 |
| 3 | (egCB)(egCB)XNdT | BT1 | 1.7 |
| 4 | (egCB)(egCB)(BT1)XdT | egCB | 0.7 |

*N represents an equimolar mixture of BT1, BT2, mA, mU, pG, nC, dG, dT, mmU, egNH, egCB and egIM, where BT1 is 1-(2'-deoxy-β-D-erythro-pentofuranosyl)-1H-benzotriazole, and BT2 is 2-(2'-deoxy-β-D-erythro-pentofuranosyl)-1H-benzotriazole.

In the initial round of screening, the subset with egCB in the first position, i.e. (egCB)NNNdT, showed greatest activty. In the second round, subset (egCB)(egCB)(NNdT was most active, and the activity increased from an $IC_{50}$ of 40 $\mu$M in round 1 to 6 $\mu$M in round 2, an approximately seven-fold improvement in activity. Assay of subsets from rounds 3 and 4 resulted in the identification of the most active oligomer, i.e. (egCB) (egCB) (BT1) (egCB)dT, with the lowest $IC_{50}$ of 0.7 $\mu$M.

TABLE IX

| Round | Sequence* | Most Active X = | $IC_{50}$ ($\mu$M) |
|---|---|---|---|
| 1 | XNNNNdT | egOC | 15 |
| 2 | (egOC)XNNNdT | egOC | 7 |
| 3 | (egOC)(egOC)XNNdT | egIM | 2 |

The first two rounds of synthesis and selection were useful in the determination of the first two monomer units of the oligomer, i.e. (egOC) (egOC)NNNdT, with an $IC_{50}$ of 7 $\mu$M. The next round led to the selection of an oligomer with an improved $IC_{50}$ of 2 $\mu$M. Further rounds can be performed for the identification of a unique oligomer with the best activity.

EXAMPLE 138

Assay for Detection of Inhibition of Human Immunodeficiency Virus

An in vitro HIV infection assay was used to select inhibitors of HIV replication from combinatorial libraries. Buckheit et al., Antiviral Res. 1993, 21, 247. Human T-lymphoblastoid CEM cell line was maintained in an exponential growth phase in RPMI 1640 with 10% fetal calf serum, glutamine, and antibiotics. On the day of the assay, the cells were washed and counted by trypan blue exclusion. These cells (CEM-IIIB) were seeded in each well of a 96-well microtiter plate at 5×10$^3$ cells per well. Following the addition of cells to each well, the library subsets were added at the indicated concentrations and serial half log dilutions. Infectious HIV-1$_{IIIB}$ was immediately added to each well at a multiplicity of infection determined to give complete cell killing at 6 days post-infection. Following 6 days of incubation at 37° C., an aliquot of supernatant was removed from each well prior to the addition of the tetrazolium dye XTT to each well. The XTT was metabolized to a formazan blue product by viable cells which was quantitatively measure spectrophotometrically with a Molecular Devices Vmax Plate Reader. The XTT assay measures protection from the HIV-induced cell killing as a result of the addition of test compounds. The supernatant aliquot was utilized to confirm the activities determined in the XTT assay. Reverse transcriptase assays and p24 ELISA were performed to measure the amount of HIV released from the infected cells. Protection from killing results in an increased optical density in the XTT assay and reduced levels of viral reverse transcriptase and p24 core protein. The results are shown in Table X.

TABLE X

| Round | Sequence* | Most Active X = | $IC_{50}$ ($\mu$M) |
|---|---|---|---|
| 1 | $G_4XNNNG_4$ | egCB | 4 |
| 2 | $G_4(egCB)XNNNG_4$ | egCB | 2 |

*N represents an equimolar mixture of dA, dT, dG, dC, egCB and egIM.

Two rounds of synthesis and selection led to the termination of the subset $G_4(egCB)$ (egCB)$NNG_4$ as the best subset with an $IC_{50}$ of 2 $\mu$M. Additional rounds can performed for the identification of a unique oligomer with further increase in activity.

$Y_0$ is H, or $[Q_2]jj-Z_2$;

$T_0$ is $[Q_1]kk-Z_1$, or together $Y_0$ and $T_0$ are joined in a nitrogen heterocycle;

$Q_1$ and $Q_2$ independently, are $C_2-C_{10}$ alkyl, $C_2-C_{10}$ alkenyl, $C_2-C_{10}$ alkynyl, $C_4-C_7$ carbocylo alkyl or alkenyl, a heterocycle, an ether having 2 to 10 carbon atoms and 1 to 4 oxygen or sulfur atoms, a polyalkyl glycol, or $C_7-C_{14}$ aralkyl;

jj and kk independently, are 0 or 1;

$Z_1$ and $Z_2$, independently, are H, $C_1-C_{20}$ alkyl, $C_2-C_{20}$ alkenyl, $C_2-C_{20}$ alkynyl, $C_6-C_{14}$ aryl, $C_7-C_{15}$ aralkyl, a halogen, CH=O, $OR_1$, $SR_2$, $NR_3R_4$, C(=NH)$NR_3R_4$, CH($NR_3R_4$), NHC(=NH)$NR_3R_4$, CH($NH_2$)C(=O)OH, C(=O)$NR_3R_4$, C(=O)$OR_5$, a metal coordination group, a reporter group, a nitrogen-containing heterocycle, a purine, a pyrimidine, a phosphate group, a polyether group, or a polyethylene glycol group;

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( x i ) SEQUENCE DESCRIPTION: SEQ ID NO:1:

T T G C T T C C A T  C T T C C T C G T C                 2 0

( 2 ) INFORMATION FOR SEQ ID NO:2:

( i ) SEQUENCE CHARACTERISTICS:
( A ) LENGTH: 12 bases
( B ) TYPE: nucleic acid
( C ) STRANDEDNESS: single
( D ) TOPOLOGY: linear ( x i ) SEQUENCE DESCRIPTION: SEQ ID NO:2:

G G G G N N N N G G  G G                                 1 2

We claim:

1. A compound having structure II:

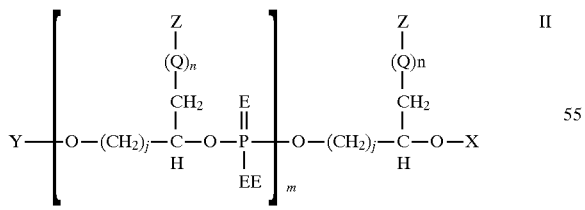

wherein:

X is H, a phosphate group, an activated phosphate group, an activated phosphite group, a solid support, a conjugate group, or an oligonucleotide;

Y is H, a hydroxyl protecting group, a conjugate group or an oligonucleotide;

E is O or S;

EE is $O^-$ or $N(Y_0)T_0$, provided that at least one EE is $N(Y_0)T_0$;

Z is $L_1$, $L_1-G_1$, $L_2$, $L_2-G_2$, $NR_3R_4$, a nitrogen-containing heterocycle, a purine, a pyrimidine, a phosphate group, a polyether group, or a polyethylene glycol group, provided that at least two of Z and $Z_m$ are different moieties, and wherein Z and each $Z_m$ are in a random sequence;

$L_1$ is alkyl having 1 to about 20 carbon atoms, alkenyl having 2 to about 20 carbon atoms, or alkynyl having 2 to about 20 carbon atoms;

$L_2$ is aryl having 6 to about 14 carbon atoms or aralkyl having 7 to about 15 carbon atoms;

$G_1$ is halogen, $OR_1$, $SR_2$, $NR_3R_4$, C(=NH)$NR_3R_4$, NHC(=NH)$NR_3R_4$, CH=O, C(=O)$OR_5$, CH($NR_3R_4$)(C(=O)$OR_5$) , C(=O)$NR_3R_4$, a metal coordination group, or a phosphate group;

$G_2$ is halogen, OH, SH, $SCH_3$, or $NR_3R_4$;

$R_1$ is H, alkyl having 1 to about 6 carbon atoms, or a hydroxyl protecting group;

$R_2$ is H, alkyl having 1 to about 6 carbon atoms, or a thiol protecting group;

R₃ and R₄ are, independently, H, alkyl having 1 to about 6 carbon atoms, or an amine protecting group;

R₅ is H, alkyl having 1 to about 6 carbon atoms, or an acid protecting group;

Q is L₁, G₃, L₁-G₃ or G₃-L₁-G₃;

G₃ is NR₃, C(=O), C(=S), C(O)—O, C(O)—NH, C(S)—O, C(S)—NH or S(O)₂, NR₃C(=O), NR₃C(=S), NR₃C(O)—O, NR₃C(O)—NH, NR₃C(S)—O, NR₃C(S)—NH or NR₃S(O)₂;

n is 0 or 1;

j is 1 to 6; and m is 1 to 50.

2. A compound having structure II:

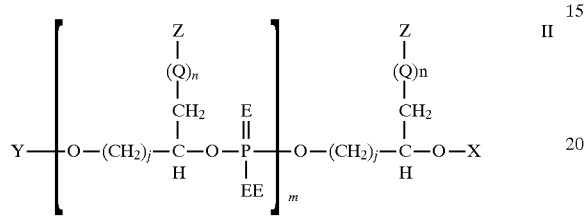

wherein:

X is H, a phosphate group, an activated phosphate group, an activated phosphite group, a solid support, a conjugate group, or an oligonucleotide;

Y is H, a hydroxyl protecting group, a conjugate group or an oligonucleotide;

E is O or S;

EE is O or N(Y₀)T₀, provided that at least one EE is N(Y₀)T₀;

Y₀ is H, or [Q₂]jj-Z₂;

To is [Q₁]kk-Z₁, or together Y₀ and T₀ are joined in a nitrogen heterocycle;

Q₁ and Q₂ independently, are C₂–C₁₀ alkyl, C₂–C₁₀ alkenyl, C₂–C₁₀ alkynyl, C₄–C₇ carbocylo alkyl or alkenyl, a heterocycle, an ether having 2 to 10 carbon atoms and 1 to 4 oxygen or sulfur atoms, a polyalkyl glycol, or C₇–C₁₄ aralkyl;

jj and kk independently, are 0 or 1;

Z₁, and Z₂, independently, are H, C₁–C₂₀ alkyl, C₂–C₂₀ alkenyl, C₂–C₂₀ alkynyl, C₆–C₁₄ aryl, C₇–C₁₄ aralkyl, a halogen, CH=O, OR₁, SR₂, NR₃R₄, C(=NH)NR₃R₄, CH(NR₃R₄), NHC(=NH)NR₃R₄, CH(NH₂)C(=O)OH, C(=O)NR₃R₄, C(=O)OR₅, a metal coordination group, a reporter group, a nitrogen-containing heterocycle, a purine, a pyrimidine, a phosphate group, a polyether group, or a polyethylene glycol group;

Z is L₁, L₁-G₁, L₂, L₂-G₂, NR₃R₄, a nitrogen-containing heterocycle, a purine, a pyrimidine, a phosphate group, a polyether group, or a polyethylene glycol group, provided that at least two of Z and Zₘ are different moieties;

L₁ is alkyl having 1 to about 20 carbon atoms, alkenyl having 2 to about 20 carbon atoms, or alkynyl having 2 to about 20 carbon atoms;

L₂ is aryl having 6 to about 14 carbon atoms or aralkyl having 7 to about 15 carbon atoms;

G₁ is halogen, OR₁, SR₂, NR₃R₄) C(=NH)NR₃R₄, NHC(=NH)NR₃R₄, CH=O, C(=O)OR₅, CH(NR₃R₄)(C(=O)OR₅), C(=O)NR₃R₄, a metal coordination group, or a phosphate group;

G₂ is halogen, OH, SH, SCH₃, or NR₃R₄;

R₁ is H, alkyl having 1 to about 6 carbon atoms, or a hydroxyl protecting group;

R₂ is H, alkyl having 1 to about 6 carbon atoms, or a thiol protecting group;

R₃ and R₄ are, independently, H, alkyl having 1 to about 6 carbon atoms, or an amine protecting group;

R₅ is H, alkyl having 1 to about 6 carbon atoms, or an acid protecting group;

Q is L₁, G₃, L₁-G₃ or G₃-L₁-G₃;

G₃ is NR₃, C(=O), C(=S), C(O)—O, C(O)—NH, C(S)—O, C(S)—NH or S(O)₂, NR₃C(=O), NR₃C(=S), NR₃C(O)—O, NR₃C(O)—NH, NR₃C(S)—O, NR₃C(S)—NH or NR₃S(O)₂;

N is 0 or 1;

j is 1 to 6; and m is 1 to 50.

3. The compound of claim 2 wherein Y is a hydroxyl protecting group.

4. The compound of claim 3 wherein Y is trityl, methoxytrityl, dimethoxytrityl or trimethoxytrityl.

5. The compound of claim 2 wherein X is H, an activated phosphite group, or a solid support.

6. The compound of claim 5 wherein X is a phosphoramidite.

7. The compound of claim 2 wherein n is 1 and Q and each Qₘ, independently, are carbonyl, thiocarbonyl, carboxy, acetyl, amido, succinyl, carbamoyl, thiocarbamoyl, ureido, thioureido, or sulfonamido acyl group.

8. The compound of claim 2 wherein Z and each Zₘ are nitrogen-containing heterocycles.

9. The compound of claim 8 wherein said nitrogen-containing heterocycle is imidazole, pyrrole or carbazole.

10. The compound of claim 9 wherein Z and each Zₘ, independently, are imidazole or carbazole.

11. The compound of claim 2 wherein Z and each Zₘ, independently, are purines or pyrimidines.

12. The compound of claim 11 wherein Z and each Zₘ, independently, are adenine, guanine, cytosine, uridine or thymine.

13. The compound of claim 12 wherein n is 0.

14. The compound of claim 2 wherein Z and each Zₘ, independently, are alkyl having 1 to about 20 carbon atoms.

15. The compound of claim 2 wherein Z and each Zₘ, independently, are C₁–C₆ alkyl-NH₂.

16. The compound of claim 2 wherein Z and each Zₘ, independently, are aryl having 6 to about 14 carbon atoms or aralkyl having 7 to about 15 carbon atoms.

17. The compound of claim 16 wherein Z and each Zₘ, independently, are carbazole, phenyl or benzyl.

18. The compound of claim 2 wherein Z and each Zₘ, independently, are glutamyl.

19. The compound of claim 2 wherein m is 1 to about 25.

20. The compound of claim 2 wherein E is O.

21. The compound of claim 2 wherein each Eₘ is S.

22. The compound of claim 2 wherein Z and each Zₘ of said compound are in a predetermined sequence.

* * * * *

UNITED STATES PATENT AND TRADEMARK OFFICE
CERTIFICATE OF CORRECTION

PATENT NO. : 5,886,177
DATED : March 23, 1999
INVENTOR(S) : Phillip Cook et al

It is certified that error appears in the above-indentified patent and that said Letters Patent is hereby corrected as shown below:

Col. 45, line 14, "(10 30 mL" should be --10mL--

Col. 46, line 1, after "29 and before "hydroxyl" insert a degree--°-.

Col. 67, line 34, "To" should be --$T_o$--

Signed and Sealed this

Tenth Day of April, 2001

Attest:

NICHOLAS P. GODICI

Attesting Officer    Acting Director of the United States Patent and Trademark Office